(12) United States Patent
Ramos et al.

(10) Patent No.: US 11,744,885 B2
(45) Date of Patent: Sep. 5, 2023

(54) VACCINES FOR RECURRENT RESPIRATORY PAPILLOMATOSIS AND METHODS OF USING THE SAME

(71) Applicant: Inovio Pharmaceuticals, Inc., Plymouth Meeting, PA (US)

(72) Inventors: Stephanie Ramos, Santee, CA (US); Jewell Walters, Poway, CA (US); Jian Yan, Wallingford, PA (US); Anna Slager, Lansdale, PA (US); Charles Reed, Souderton, PA (US); Kate Broderick, San Diego, CA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 179 days.

(21) Appl. No.: 17/320,944

(22) Filed: May 14, 2021

(65) Prior Publication Data

US 2021/0353736 A1    Nov. 18, 2021

Related U.S. Application Data

(60) Provisional application No. 63/024,912, filed on May 14, 2020.

(51) Int. Cl.
*A61K 39/12* (2006.01)
*C07K 14/025* (2006.01)
*A61K 39/00* (2006.01)

(52) U.S. Cl.
CPC ............ *A61K 39/12* (2013.01); *C07K 14/025* (2013.01); *A61K 2039/5254* (2013.01); *A61K 2039/54* (2013.01); *A61K 2039/55538* (2013.01)

(58) Field of Classification Search
None
See application file for complete search history.

(56) References Cited

U.S. PATENT DOCUMENTS

| | | |
|---|---|---|
| 3,805,783 A | 4/1974 | Ismach |
| 4,342,310 A | 8/1982 | Lindmayer et al. |
| 4,447,223 A | 5/1984 | Kaye et al. |
| 5,505,697 A | 4/1996 | McKinnon et al. |
| 5,580,859 A | 12/1996 | Felgner et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 6,009,347 A | 12/1999 | Hofmann |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,302,874 B1 | 10/2001 | Zhang et al. |
| 6,520,950 B1 | 2/2003 | Hofmann et al. |
| 6,763,264 B2 | 7/2004 | Hofmann |
| 7,171,264 B1 | 1/2007 | Hofmann et al. |
| 7,245,963 B2 | 7/2007 | Draghia-Akli et al. |
| 7,328,064 B2 | 2/2008 | Mathiesen et al. |
| 7,664,545 B2 | 2/2010 | Westersten et al. |
| 2004/0175727 A1 | 9/2004 | Draghia-Akli et al. |
| 2008/0234655 A1 | 9/2008 | Mathiesen et al. |
| 2017/0151320 A1* | 6/2017 | Weiner ............... A61K 39/145 |
| 2018/0179257 A1 | 6/2018 | Monath et al. |
| 2019/0062379 A1 | 2/2019 | Li et al. |
| 2019/0192650 A1 | 6/2019 | Weiner et al. |

FOREIGN PATENT DOCUMENTS

WO    2019/151760 A1    8/2019

OTHER PUBLICATIONS

GenBank: AAK84425.1. interleukin 12A (natural killer cell stimulatory factor 1, cytotoxic lymphocyte maturation factor 1, p35) [*Homo sapiens*]. Dated Aug. 9, 2001.*
GenBank: BAJ20855.1. interleukin 12B, partial [synthetic construct]. Dated Jul. 25, 2016.*
ISA/220—Notification of Transmittal or Search Report and Written Opinion of the ISA, or the Declaration dated Sep 16, 2021 for WO Application No. PCT/US21/032545.
"INO-3107 With Electroporation (EP) in Participants With HPV-6- and/or HPV-11-Associated Recurrent Respiratory Papillomatosis (RRP)"; https://clinicaltrials.gov/ct2/show/NCT04398433; accessed Jun. 3, 2021; 8 pages.
Bonagura et al.; "Recurrent respiratory papillomatosis: a complex defect in immune responsiveness to human papillomavirus-6 and -11"; Journal of Pathology, Microbiology and Immunology; vol. 118; 2010; p. 455-470.
Donnelly et al.; "DNA Vaccines"; Annual Review of Immunology; vol. 15; 1997; p. 617-648.
Gissmann et al.; "Human papillomavirus types 6 and 11 DNA sequences in genital and laryngeal papillomas and in some cervical cancers"; Proc. Natl. Acad. Sci.; vol. 80; Jan. 1983; p. 560-563.

(Continued)

*Primary Examiner* — Nianxiang Zou
(74) *Attorney, Agent, or Firm* — BakerHostetler

(57) ABSTRACT

Provided herein are nucleic acid molecules encoding an HPV antigen. Also provided are vaccines against human papillomavirus (HPV) comprising the nucleic acids, methods of inducing immune responses, and methods for prophylactically and/or therapeutically immunizing individuals against recurrent respiratory papillomatosis (RRP). Pharmaceutical compositions, recombinant vaccines comprising DNA plasmid and live attenuated vaccines are disclosed as well as methods of inducing an immune response to treat or prevent RRP are disclosed.

35 Claims, 14 Drawing Sheets

Specification includes a Sequence Listing.

(56) References Cited

OTHER PUBLICATIONS

Gradishar et al.; "Breast Cancer Version 3.2014"; Nat'l Comprehensive Cancer Network; vol. 12; Apr. 2014; p. 542-590.
Mounts et al.; "Viral etiology of juvenile- and adult-onset squamous papilloma of the larynx"; Proc. Natl. Acad. Sci.; vol. 79; Sep. 1982; p. 5425-5429.
Omland et al.; "Recurrent Respiratory Papillomatosis: HPV Genotypes and Risk of High-Grade Laryngeal Neoplasia" Plos ONE; vol. 9; Jun. 2014; e99114; 7 pages.
Schultheis et al.; "Optimized Interferon-gamma ELISpot Assay to Measure T Cell Responses in the Guinea Pig Model after Vaccination"; Journal of Visualized Experiments; vol. 143; Jan. 2019; 7 pages.
Winton et al.; "Vinorelbine plus Cisplatin vs. Observation in Resected Non-Small-Cell Lung Cancer"; The New England Journal of Medicine; vol. 352; 2005; p. 2589-2597.
IPEA/409—International Preliminary Report on Patentability dated Nov. 24, 2022 for WO Application No. PCT/US21/032545.

* cited by examiner

Plasmid map of pGX3024

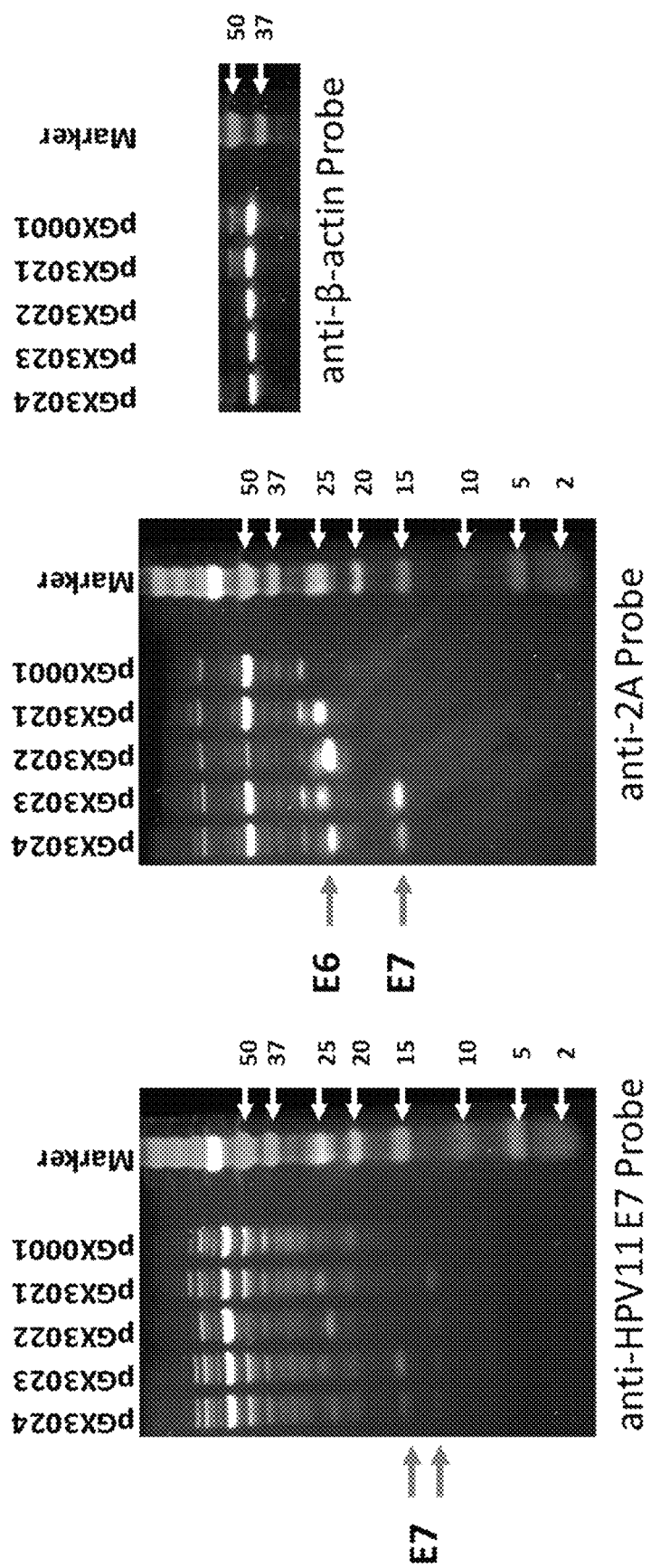

HPV6 and HPV11 specific cellular responses following pGX3024 immunization of C57BL/6 mice HPV6 and HPV11 humoral responses following pGX3024 immunization of C57BL/6 mice HPV6 and HPV11 specific cellular responses following pGX3024 immunization of BALB/c mice HPV6 and HPV11 humoral responses following pGX3024 immunization of BALB/c mice Timecourse of HPV6 and HPV11 specific cellular responses following INO-3107 immunization of NZW rabbits HPV6 and HPV11 specific cellular responses following INO-3107 immunization of NZW rabbits

Timecourse of HPV6 and HPV11 humoral responses following INO-3107 immunization of NZW rabbits

Body weights of INO-3107 immunized of NZW rabbits

HPV6 and HPV11 specific cellular responses following intradermal pGX3024 immunization of guinea pigs HPV6 and HPV11 humoral responses following intradermal pGX3024 immunization of guinea pigs Immune responses induced following intradermal delivery of INO-3107

SEQUENCE LISTING

<160> NUMBER OF SEQ ID NOS: 12

<210> SEQ ID NO 1
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ser Lys Asp Ala Ser Thr Ser Ala Thr Ser Ile Asp Gln Leu Cys
1               5                   10                  15

Lys Thr Phe Asn Leu Ser Leu His Thr Leu Gln Ile Gln Cys Val Phe
            20                  25                  30

```
Cys Arg Asn Ala Leu Thr Thr Ala Glu Ile Tyr Ala Tyr Ala Tyr Lys
        35                  40                  45

Asn Leu Lys Val Val Trp Arg Asp Asn Phe Pro Phe Ala Ala Cys Ala
 50                  55                  60

Cys Cys Leu Glu Leu Gln Gly Lys Ile Asn Gln Tyr Arg His Phe Asn
 65                  70                  75                  80

Tyr Ala Ala Tyr Ala Pro Thr Val Glu Glu Thr Asn Glu Asp Ile
                85                  90                  95

Leu Lys Val Leu Ile Arg Cys Tyr Leu Cys His Lys Pro Gln Cys Glu
                100                 105                 110

Ile Glu Lys Leu Lys His Ile Leu Gly Lys Ala Arg Phe Ile Lys Leu
                115                 120                 125

Asn Asn Gln Arg Lys Gly Arg Cys Leu His Cys Trp Thr Thr Cys Met
130                 135                 140

Glu Asp Leu Leu Pro Arg Gly Arg Lys Arg Ser Gly Ser Gly Ala
145                 150                 155                 160

Thr Asn Phe Ser Leu Leu Lys Gln Ala Gly Asp Val Glu Glu Asn Pro
                165                 170                 175

Gly Pro His Gly Arg Leu Val Thr Leu Lys Asp Ile Val Leu Asp Leu
                180                 185                 190

Gln Pro Pro Asp Pro Val Gly Leu His Ala Tyr Glu Gln Leu Glu Asp
                195                 200                 205

Ser Ser Glu Asp Glu Val Asp Lys Val Asp Lys Gln Asp Ser Gln Pro
210                 215                 220

Leu Thr Gln His Tyr Gln Ile Leu Thr Cys Cys Cys Gly Cys Asp Ser
225                 230                 235                 240

Asn Val Arg Leu Val Val Glu Cys Thr Asp Gly Asp Ile Arg Gln Leu
                245                 250                 255

Gln Asp Leu Leu Leu Gly Thr Leu Asn Ile Val Cys Pro Ile Cys Ala
                260                 265                 270

Pro Lys Pro Arg Gly Arg Lys Arg Ser Gly Ser Gly Ala Thr Asn
                275                 280                 285

Phe Ser Leu Leu Lys Gln Ala Gly Asp Val Glu Asn Pro Gly Pro
290                 295                 300

Glu Ser Ala Asn Ala Ser Thr Ser Ala Thr Thr Ile Asp Gln Leu Cys
305                 310                 315                 320

Lys Thr Phe Asn Leu Ser Met His Thr Leu Gln Ile Asn Cys Val Phe
                325                 330                 335

Cys Lys Asn Ala Leu Thr Thr Ala Glu Ile Tyr Ser Tyr Ala Tyr Lys
                340                 345                 350

Gln Leu Lys Val Leu Phe Arg Gly Gly Tyr Pro Tyr Ala Ala Cys Ala
                355                 360                 365

Cys Cys Leu Glu Phe His Gly Lys Ile Asn Gln Tyr Arg His Phe Asp
370                 375                 380

Tyr Ala Gly Tyr Ala Thr Thr Val Glu Glu Thr Lys Gln Asp Ile
385                 390                 395                 400

Leu Asp Val Leu Ile Arg Cys Tyr Leu Cys His Lys Pro Gln Cys Glu
                405                 410                 415

Val Glu Lys Val Lys His Ile Leu Thr Lys Ala Arg Phe Ile Lys Leu
                420                 425                 430

Asn Cys Thr Arg Lys Gly Arg Cys Leu His Cys Trp Thr Thr Cys Met
                435                 440                 445
```

Glu Asp Met Leu Pro Arg Gly Arg Lys Arg Arg Ser Gly Ser Gly Ala
450                 455                 460

Thr Asn Phe Ser Leu Leu Lys Gln Ala Gly Asp Val Glu Glu Asn Pro
465                 470                 475                 480

Gly Pro His Gly Arg His Val Thr Leu Lys Asp Ile Val Leu Asp Leu
            485                 490                 495

Gln Pro Pro Asp Pro Val Gly Leu His Ala Tyr Glu Gln Leu Val Asp
            500                 505                 510

Ser Ser Glu Asp Glu Val Asp Glu Val Asp Gly Gln Asp Ser Gln Pro
            515                 520                 525

Leu Lys Gln His Tyr Gln Ile Val Thr Cys Cys Cys Gly Cys Asp Ser
530                 535                 540

Asn Val Arg Leu Val Val Gln Cys Thr Glu Thr Asp Ile Arg Glu Val
545                 550                 555                 560

Gln Gln Leu Leu Leu Gly Thr Leu Asn Ile Val Cys Pro Ile Cys Ala
                565                 570                 575

Pro Lys Thr

<210> SEQ ID NO 2
<211> LENGTH: 1743
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gagagcaagg atgccagcac aagcgccacc agcatcgacc agctttgcaa gacctttaac      60
ctgagcctgc acacacttca gatccagtgt gtcttctgcc gaaatgctct gacaacagca     120
gaaatctacg cctacgccta caaaaacctg aaggtggtgt ggagagacaa ctttcctttc     180
gctgcctgcg cttgctgcct ggagctgcag ggcaagatca atcagtaccg cacttcaac      240 tacgctgcct acgccctac agtggaggag gaaacaaacg aagacatcct gaaggtgctg     300
atcagatgct acctctgcca aagccacag tgtgaaatcg agaagctgaa gcacattctg     360
ggcaaggcca gatttatcaa gctgaacaac agagaaaagg gaagatgtct gcactgttgg     420
acaacctgca tggaggacct gctgcccaga ggcagaaaga aagatctgg cagcggagct     480 accaacttct ctctgctgaa gcaggctgga gatgttgagg agaacccagg ccctcacggc     540
cggctggtca ccctgaagga tatcgtgctg atctgcagc cccctgatcc tgtgggcctt     600
cacgcctacg aacagctgga ggacagctct gaagacgaag tggacaaggt ggacaagcag     660
gactctcagc ctctgacaca gcactatcag atcctgacct gctgctgcgg ctgtgactct     720
aacgtgagac tggtggtgga gtgcaccgat ggagacatca gacagctgca ggacctgctg     780
ctgggtaccc tgaacattgt gtgtcctatc tgtgctccaa agccaagagg caggaaaaga     840
agatccggca gcggagccac caatttctcc ctgctgaagc aagctggaga tgtggaggag     900
aaccctggcc ctgagagcgc caacgccagc acatccgcca ccaccatcga ccagctgtgc     960
aagaccttca acctgagcat gcacacactg cagatcaact gtgtcttctg caagaatgcc    1020
ctgaccacag cagagatcta cagctacgcc tacaagcagc tgaaggtgct gttcagaggc    1080
ggctacccct tatgctgcctg tgcctgctgc ctggagttcc acggcaagat caaccagtac    1140
agacacttcg actacgctgg ctacgccacc acagtggaag aggaaacaaa gcaggacatc    1200
ctggacgtgc tgatccgatg ctacctgtgc cacaagcctc agtgtgaagt ggaaaaagtg    1260

| | |
|---|---:|
| aagcacatcc tgaccaaggc cagattcatc aagctgaact gcaccagaaa aggcagatgc | 1320 |
| ctgcactgct ggaccacctg catggaagac atgctgccta gaggcagaaa aagaagaagc | 1380 |
| ggctctggag ccaccaactt ttccctgctg aaacaagctg gagacgtgga ggaaaaccct | 1440 |
| ggccctcacg gcagacacgt gacactgaag gacatcgtgc tggacctgca gcctcctgac | 1500 |
| cctgtgggcc tgcacgccta cgagcagctg gtggacagca gcgaggacga agtggacgaa | 1560 |
| gtggatggcc aggacagcca gcctctgaag cagcactacc agatcgtcac ctgctgctgt | 1620 |
| ggctgtgata gcaatgtgag gctggtggtg cagtgcacag aaacagacat cagagaagtg | 1680 |
| cagcaactgc tgctgggcac cctgaacatc gtgtgtccca tctgtgctcc aagacatga | 1740 |
| taa | 1743 |

<210> SEQ ID NO 3
<211> LENGTH: 4751
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---:|
| gctgcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| gtatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca gctggctag cgtttaaact taagcttggt | 720 |
| accgagctcg gatccgccac catggattgg acctggattc tctttctcgt tgccgctgct | 780 |
| actcgcgttc atagtgagag caaggatgcc agcacaagcg ccaccagcat cgaccagctt | 840 |
| tgcaagacct ttaacctgag cctgcacaca cttcagatcc agtgtgtctt ctgccgaaat | 900 |
| gctctgacaa cagcagaaat ctacgcctac gcctacaaaa acctgaaggt ggtgtggaga | 960 |
| gacaactttc ctttcgctgc ctgcgcttgc tgcctggagc tgcagggcaa gatcaatcag | 1020 |
| taccggcact tcaactacgc tgcctacgcc cctacagtgg aggaggaaac aaacgaagac | 1080 |
| atcctgaagg tgctgatcag atgctacctc tgccacaagc acagtgtgaa atcgagaag | 1140 |
| ctgaagcaca ttctgggcaa ggccagattt atcaagctga caaccagag aaagggaaga | 1200 |
| tgtctgcact gttggacaac ctgcatggag gacctgctgc ccagaggcag aaagagaaga | 1260 |
| tctggcagcg gagctaccaa cttctctctg ctgaagcagg ctggagatgt tgaggagaac | 1320 |
| ccaggccctc acggccggct ggtcaccctg aaggatatcg tgctggatct gcagcccct | 1380 |
| gatcctgtgg gccttcacgc ctacgaacag ctggaggaca gctctgaaga cgaagtggac | 1440 |
| aaggtggaca agcaggactc tcagcctctg acacagcact atcagatcct gacctgctgc | 1500 |

-continued

```
tgcggctgtg actctaacgt gagactggtg gtggagtgca ccgatggaga catcagacag    1560
ctgcaggacc tgctgctggg taccctgaac attgtgtgtc ctatctgtgc tccaaagcca    1620
agaggcagga aaagaagatc cggcagcgga gccaccaatt tctccctgct gaagcaagct    1680
ggagatgtgg aggagaaccc tggccctgag agcgccaacg ccagcacatc cgccaccacc    1740
atcgaccagc tgtgcaagac cttcaacctg agcatgcaca cactgcagat caactgtgtc    1800
ttctgcaaga atgccctgac cacagcagag atctacagct acgcctacaa gcagctgaag    1860
gtgctgttca gaggcggcta cccttatgct gcctgtgcct gctgcctgga gttccacggc    1920
aagatcaacc agtacagaca cttcgactac gctggctacg ccaccacagt ggaagaggaa    1980
acaaagcagg acatcctgga cgtgctgatc cgatgctacc tgtgccacaa gcctcagtgt    2040
gaagtggaaa agtgaagca catcctgacc aaggccagat tcatcaagct gaactgcacc    2100
agaaaaggca gatgcctgca ctgctggacc acctgcatgg aagacatgct gcctagaggc    2160 agaaaagaa gaagcggctc tggagccacc aacttttccc tgctgaaaca agctggagac    2220
gtggaggaaa accctggccc tcacggcaga cacgtgacac tgaaggacat cgtgctggac    2280
ctgcagcctc ctgaccctgt gggcctgcac gcctacgagc agctggtgga cagcagcgag    2340
gacgaagtgg acgaagtgga tggccaggac agccagcctc tgaagcagca ctaccagatc    2400
gtcacctgct gctgtggctg tgatagcaat gtgaggctgg tggtgcagtg cacagaaaca    2460
gacatcagag aagtgcagca actgctgctg gcaccctga acatcgtgtg tcccatctgt    2520
gctcccaaga catgataact cgagtctaga gggcccgttt aaacccgctg atcagcctcg    2580
actgtgcctt ctagttgcca gccatctgtt gtttgcccct cccccgtgcc ttccttgacc    2640
ctggaaggtg ccactcccac tgtcctttcc taataaaatg aggaaattgc atcgcattgt    2700
ctgagtaggt gtcattctat tctgggggt ggggtggggc aggacagcaa ggggaggat    2760 tgggaagaca atagcaggca tgctggggat gcggtgggct ctatggcttc tactgggcgg    2820
ttttatggac agcaagcgaa ccggaattgc cagctgggc ccctctggt aaggttggga    2880 agccctgcaa agtaaactgg atggctttct gccgccaag gatctgatgg cgcaggggat    2940
caagctctga tcaagagaca ggatgaggat cgtttcgcat gattgaacaa gatggattgc    3000
acgcaggttc tccggccgct tgggtggaga ggctattcgg ctatgactgg gcacaacaga    3060
caatcggctg ctctgatgcc gccgtgttcc ggctgtcagc gcaggggcgc ccggttcttt    3120
ttgtcaagac cgacctgtcc ggtgccctga tgaactgca agacgaggca gcgcggctat    3180
cgtggctggc cacgacgggc gttccttgcg cagctgtgct cgacgttgtc actgaagcgg    3240
gaagggactg gctgctattg ggcgaagtgc cggggcagga tctcctgtca tctcaccttg    3300
ctcctgccga gaaagtatcc atcatggctg atgcaatgcg gcggctgcat acgcttgatc    3360
cggctacctg cccattcgac caccaagcga aacatcgcat cgagcgagca cgtactcgga    3420
tggaagccgg tcttgtcgat caggatgatc tggacgaaga gcatcagggg ctcgcgccag    3480
ccgaactgtt cgccaggctc aaggcgagca tgcccgacgg cgaggatctc gtcgtgaccc    3540
atggcgatgc ctgcttgccg aatatcatgg tggaaaatgg ccgcttttct ggattcatcg    3600
actgtggccg gctgggtgtg gcggaccgct atcaggacat agcgttggct acccgtgata    3660
ttgctgaaga gcttggcggc gaatgggctg accgcttcct cgtgctttac ggtatcgccg    3720
ctcccgattc gcagcgcatc gccttctatc gccttcttga cgagttcttc tgaattatta    3780
acgcttacaa tttcctgatg cggtatttc tccttacgca tctgtgcggt atttcacacc    3840
gcatcaggtg gcacttttcg gggaaatgtg cgcggaaccc ctatttgttt attttttctaa    3900
```

| | | |
|---|---|---|
| atacattcaa atatgtatcc gctcatgaga caataaccct gataaatgct tcaataatag | 3960 | |
| cacgtgctaa aacttcattt ttaatttaaa aggatctagg tgaagatcct ttttgataat | 4020 | |
| ctcatgacca aaatccctta acgtgagttt tcgttccact gagcgtcaga ccccgtagaa | 4080 | |
| aagatcaaag gatcttcttg agatcctttt tttctgcgcg taatctgctg cttgcaaaca | 4140 | |
| aaaaaaccac cgctaccagc ggtggtttgt ttgccggatc aagagctacc aactctttt | 4200 | |
| ccgaaggtaa ctggcttcag cagagcgcag ataccaaata tgttcttct agtgtagccg | 4260 | |
| tagttaggcc accacttcaa gaactctgta gcaccgccta catacctcgc tctgctaatc | 4320 | |
| ctgttaccag tggctgctgc cagtggcgat aagtcgtgtc ttaccgggtt ggactcaaga | 4380 | |
| cgatagttac cggataaggc gcagcggtcg ggctgaacgg ggggttcgtg cacacagccc | 4440 | |
| agcttggagc gaacgaccta caccgaactg agatacctac agcgtgagct atgagaaagc | 4500 | |
| gccacgcttc ccgaagggag aaaggcggac aggtatccgg taagcggcag gtcggaaca | 4560 | |
| ggagagcgca cgagggagct tccagggga aacgcctggt atctttatag tcctgtcggg | 4620 | |
| tttcgccacc tctgacttga gcgtcgattt ttgtgatgct cgtcaggggg cggagccta | 4680 | |
| tggaaaaacg ccagcaacgc ggccttttta cggttcctgg ccttttgctg gccttttgct | 4740 | |
| cacatgttct t | 4751 | |

<210> SEQ ID NO 4
<211> LENGTH: 6229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | | |
|---|---|---|
| aaatggggc gctgaggtct gcctcgtgaa gaaggtgttg ctgactcata ccaggcctga | 60 | |
| atcgccccat catccagcca gaaagtgagg gagccacggt tgatgagagc tttgttgtag | 120 | |
| gtggaccagt tggtgatttt gaacttttgc tttgccacgg aacggtctgc gttgtcggga | 180 | |
| agatgcgtga tctgatcctt caactcagca aaagttcgat ttattcaaca aagccgccgt | 240 | |
| cccgtcaagt cagcgtaatg ctctgccagt gttacaacca attaaccaat tctgcgttca | 300 | |
| aaatggtatg cgttttgaca catccactat atatccgtgt cgttctgtcc actcctgaat | 360 | |
| cccattccag aaattctcta gcgattccag aagtttctca gagtcggaaa gttgaccaga | 420 | |
| cattacgaac tggcacagat ggtcataacc tgaaggaaga tctgattgct taactgcttc | 480 | |
| agttaagacc gacgcgctcg tcgtataaca gatgcgatga tgcagaccaa tcaacatggc | 540 | |
| acctgccatt gctacctgta cagtcaagga tggtagaaat gttgtcggtc cttgcacacg | 600 | |
| aatattacgc catttgcctg catattcaaa cagctcttct acgataaggg cacaaatcgc | 660 | |
| atcgtggaac gtttgggctt ctaccgattt agcagtttga tacactttct ctaagtatcc | 720 | |
| acctgaatca taaatcggca aaatagaaa aaattgacca tgtgtaagcg gccaatctga | 780 | |
| ttccacctga gatgcataat ctagtagaat ctcttcgcta tcaaaattca cttccacctt | 840 | |
| ccactcaccg gttgtccatt catggctgaa ctctgcttcc tctgttgaca tgacacacat | 900 | |
| catctcaata tccgaatacg gaccatcagt ctgacgacca agagagccat aaacaccaat | 960 | |
| agccttaaca tcatccccat atttatccaa tattcgttcc ttaatttcat gaacaatctt | 1020 | |
| cattctttct tctctagtca ttattattgg tccgttcata acaccccttg tattactgtt | 1080 | |
| tatgtaagca gacagttta ttgttcatga tgatatattt ttatcttgtg caatgtaaca | 1140 | |

```
tcagagattt tgagacacaa cgtggctttc cccggcccat gaccaaaatc ccttaacgtg      1200
agttttcgtt ccactgagcg tcagaccccg tagaaaagat caaaggatct tcttgagatc      1260 cttttttttct gcgcgtaatc tgctgcttgc aaacaaaaaa accaccgcta ccagcggtgg     1320
tttgtttgcc ggatcaagag ctaccaactc tttttccgaa ggtaactggc ttcagcagag      1380
cgcagatacc aaatactgtt cttctagtgt agccgtagtt aggccaccac ttcaagaact      1440
ctgtagcacc gcctacatac ctcgctctgc taatcctgtt accagtggct gctgccagtg     1500
gcgataagtc gtgtcttacc gggttggact caagacgata gttaccggat aaggcgcagc     1560
ggtcgggctg aacggggggt tcgtgcacac agcccagctt ggagcgaacg acctacaccg     1620
aactgagata cctacagcgt gagctatgag aaagcgccac gcttcccgaa gggagaaagg     1680
cggacaggta tccggtaagc ggcagggtcg aacaggaga gcgcacgagg gagcttccag      1740
ggggaaacgc ctggtatctt tatagtcctg tcgggtttcg ccacctctga cttgagcgtc     1800
gatttttgtg atgctcgtca ggggggcgga gcctatggaa aaacgccagc aacgcggcct     1860
ttttacggtt cctggccttt tgctggcctt ttgctcacat gttctttcct gcgttatccc     1920
ctgattctgt ggataaccgt attaccgcct ttgagtgagc tgataccgct cgccgcagcc     1980
gaacgaccga gcgcagcgag tcagtgagcg aggaagcgga agagcgcctg atgcggtatt     2040
ttctccttac gcatctgtgc ggtatttcac accgcatatg gtgcactctc agtacaatct     2100
gctctgatgc cgcatagtta agccagtatc tgctccctgc ttgtgtgttg gaggtcgctg     2160
agtagtgcgc gagcaaaatt taagctacaa caaggcaagg cttgaccgac aattgcatga     2220
agaatctgct tagggttagg cgttttgcgc tgcttcgcga tgtacgggcc agatatagcc     2280
gcggcatcga tgataattcg gcttatttaa attccccagc atgcctgcta ttgtcttccc     2340
aatcctcccc cttgctgtcc tgccccaccc caccccccag aatagaatga cacctactca     2400
gacaatgcga tgcaatttcc tcattttatt aggaaaggac agtgggagtg caccttcca      2460 gggtcaagga aggcacgggg gagggcaaa caacagatgg ctgcaacta aaggcacag       2520 tcgaggctga tcagcgagct cggcgcgcct ctcgagttag gaagcgttca ggtatgacat     2580
gacccgatca atagtgacag cccgaatccg aaaggcatgc agcagaatgc acagcttgat    2640
ttttgtctta taaagtcgg gttcctccag actagacttc tgtgggacgg tttcgctatt     2700
gaagttcagg gcctgcatca gctcgtcaat cactgccagc atattctgat ccagaaagat    2760
ctgtcgttta gggtccatca gcagcttagc gttcatggtt ttgaattcca cctgatacat    2820
cttcagatcc tcgtagatgg agctcaggca cagtgccatc atgaagctgg tcttgcgact    2880
agccaggcaa gacccgttgg tgatgaagga agtctccctg ctattcagac atgattcgtt    2940
cttggtcagc tccagtggca ggcagcttc gactgtggag gttttgtcct tagtaatatc     3000
ctcgtggtcg atttcctcag aagtacaagg gtaaaactcc agtgtctgtc tagctttctg    3060
cagcatattg gacacggccc gcagcaggtt ctggctatgg tgcaggcagg gaacatgcc     3120 aggatcgggg gtagcgacag gcagatttcg agccagtgac aggtgatcca gcaggaccag    3180
ggtagcgacc agcagcaggg accgagcggg gcacatgttt aaacgctcct ccgacgtccc    3240
caggcagaat ggcggttccc taaacgagca ttgcttatat agacctccca ttaggcacgc    3300
ctaccgccca tttacgtcaa tggaacgccc atttgcgtca ttgcccctcc ccattgacgt    3360
caatggggat gtacttggca gccatcgcgg gccatttacc gccattgacg tcaatgggag    3420
tactgccaat gtaccctggc gtacttccaa tagtaatgta cttgccaagt tactattaat    3480
```

```
agatattgat gtactgccaa gtgggccatt taccgtcatt gacgtcaata gggggcgtga      3540
gaacggatat gaatgggcaa tgagccatcc cattgacgtc aatggtgggt ggtcctattg      3600
acgtcaatgg gcattgagcc aggcgggcca tttaccgtaa ttgacgtcaa tgggggaggc      3660
gccatatacg tcaataggac cgcccatatg acgtcaatag gaaagaccat gctaagccga      3720
attatcgcgg ctatctgagg ggactagggt gtgtttaggc gaaaagcggg gcttcggttg      3780
tacgcggtta ggagtcccct caggatatag tagtttcgct tttgcatagg gagggggaaa      3840
tgtagtctta tgcaatactc ttgtagtctt gcaacatggt aacgatgagt tagcaacatg      3900
ccttacaagg agagaaaaag caccgtgcat gccgattggt ggaagtaagg tggtacgatc      3960
gtgccttatt aggaaggcaa cagacgggtc tgacatggat tggacgaacc actgaattcc      4020
gcattgcaga gatattgtat ttaagtgcct agctcgatac aataaacgcc atttgaccat      4080
tcaccacatt ggtgtgcacc tccaagcttc gaccaattct catgtttgac agcttatcat      4140
cgcagatccg ggcaacgttg ttgccattgc tgcaggcgca gaactggtag gtatggaaga      4200
tctatacatt gaatcaatat tggcaattag ccatattagt cattggttat atagcataaa      4260
tcaatattgg ctattggcca ttgcatacgt tgtatctata tcataatatg tacatttata      4320
ttggctcatg tccaatatga ccgccatgtt gacattgatt attgactagt tattaatagt      4380
aatcaattac ggggtcatta gttcatagcc catatatgga gttccgcgtt acataactta      4440
cggtaaatgg cccgcctggc tgaccgccca acgacccccg cccattgacg tcaataatga      4500
cgtatgttcc catagtaacg ccaataggga ctttccattg acgtcaatgg gtggagtatt      4560
tacggtaaac tgcccacttg gcagtacatc aagtgtatca tatgccaagt ccgcccccta      4620
ttgacgtcaa tgacggtaaa tggcccgcct ggcattatgc ccagtacatg accttacggg      4680
actttcctac ttggcagtac atctacgtat tagtcatcgc tattaccatg gtgatgcggt      4740
tttggcagta catcaatggg cgtggatagc ggtttgactc acggggattt ccaagtctcc      4800
accccattga cgtcaatggg agtttgtttt ggcaccaaaa tcaacgggac tttccaaaat      4860
gtcgtaacaa ctccgcccca ttgacgcaaa tgggcggtag gcgtgtacgg tgggaggtct      4920
atataagcag agctcgttta gtgaaccgtc agatcgcctg gagacgccat ccacgctgtt      4980
ttgacctcca tagaagacac cgggaccgat ccagcctccg cgggcgcgcg tcgacatgtg      5040
ccatcagcag ctggtcatct cttggtttag tctggtgttt ctggcttctc cactggtcgc      5100
tatctgggaa ctgaaaaagg atgtgtacgt ggtcgagctg gactggtatc cagatgcacc      5160
cggagaaatg gtggtcctga cctgcgcacac acccgaggaa gatggcatca cttggaccct      5220
ggaccagagc tccgaggtgc tgggatctgg caagacactg actattcagg tcaaagaatt      5280
cggggatgcc ggacagtaca catgtcacaa gggcggggag gtgctgagtc actcactgct      5340
gctgctgcat aagaaagaag acggcatctg gtctactgac attctgaagg atcagaaaga      5400
gcctaagaac aaaaccttcc tgagatgcga agctaagaat tatagtggga ggtttacctg      5460
ttggtggctg accacaatct caactgacct gacctttagc gtgaaatcta gtaggggtc      5520 aagcgatcca cagggagtga cctgcggagc agctacactg agcgccgagc gggtgagagg      5580
agacaacaag gagtacgaat atagtgtcga gtgccaggaa gattcagcct gtcccgcagc      5640
cgaggaatcc ctgcctatcg aagtgatggt ggacgctgtg cacaagctga atacgaaaa      5700 ctacacatcc tctttcttta ttcgcgacat cattaagcca gatcccccta aaaacctgca      5760
gctgaagccc ctgaaaaatt cccgacaggt ggaggtctct tgggaatacc ctgatacatg      5820
gagcactcca cattcttatt tcagtctgac ttttttgcgtg caggtccagg gcaagagcaa      5880
```

```
aagggagaag aaagaccgcg tgttcaccga taagacatcc gctactgtca tctgtcgaaa    5940
aaacgcaagc atttccgtgc gggcacagga taggtattat tccagcagtt ggtctgagtg    6000
ggcttccgtc ccttgtagtt gaacgcgtaa aaagatccag acatgataag atacattgat    6060
gagtttggac aaaccacaac tagaatgcag tgaaaaaaat gctttatttg tgaaatttgt    6120
gatgctattg ctttatttgt aaccattata agctgcaata aacaagttaa caacaacaat    6180
tgcattcatt ttatgtttca ggttcagggg gaggtgtggg aggttttttt              6229

<210> SEQ ID NO 5
<211> LENGTH: 660
<212> TYPE: DNA
<213> ORGANISM: Homo sapiens

<400> SEQUENCE: 5
atgtgtccag cgcgcagcct cctccttgtg ctaccctgg tcctcctgga ccacctcagt      60
ttggccagaa actcccccgt ggccactcca gacccaggaa tgttcccatg ccttcaccac    120
tcccaaaacc tgctgagggc cgtcagcaac atgctccaga aggccagaca aactctagaa    180 ttttacccctt gcacttctga agagattgat catgaagata tcacaaaaga taaaaccagc    240
acagtggagg cctgtttacc attggaatta accaagaatg agagttgcct aaattccaga    300
gagacctctt tcataactaa tgggagttgc ctggcctcca aaagacctc ttttatgatg    360 gccctgtgcc ttagtagtat ttatgaagac ttgaagatgt accaggtgga gttcaagacc    420
atgaatgcaa agcttctgat ggatcctaag aggcagatct ttctagatca aaacatgctg    480
gcagttattg atgagctgat gcaggccctg aatttcaaca gtgagactgt gccacaaaaa    540
tcctcccttg aagaaccgga ttttataaaa actaaaatca agctctgcat acttcttcat    600
gctttcagaa ttcgggcagt gactattgat agagtgatga gctatctgaa tgcttcctaa    660

<210> SEQ ID NO 6
<211> LENGTH: 219
<212> TYPE: PRT
<213> ORGANISM: Homo sapiens

<400> SEQUENCE: 6

Met Cys Pro Ala Arg Ser Leu Leu Val Ala Thr Leu Val Leu Leu
1               5                   10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
```

```
                   145                 150                 155                 160
Ala Val Ile Asp Glu Leu Met Gln Ala Leu Asn Phe Asn Ser Glu Thr
               165                 170                 175

Val Pro Gln Lys Ser Ser Leu Glu Glu Pro Asp Phe Tyr Lys Thr Lys
           180                 185                 190

Ile Lys Leu Cys Ile Leu Leu His Ala Phe Arg Ile Arg Ala Val Thr
       195                 200                 205

Ile Asp Arg Val Met Ser Tyr Leu Asn Ala Ser
   210                 215
```

<210> SEQ ID NO 7
<211> LENGTH: 987
<212> TYPE: DNA
<213> ORGANISM: Homo sapiens

<400> SEQUENCE: 7

```
atgtgtcacc agcagttggt catctcttgg tttcccctgg tttttctggc atctcccctc      60
gtggccatat gggaactgaa gaaagatgtt tatgtcgtag aattggattg gtatccggat     120
gcccctggag aaatggtggt cctcacctgt gacacccctg aagaagatgg tatcacctgg     180
accttggacc agagcagtga ggtcttaggc tctggcaaaa ccctgaccat ccaagtcaaa     240
gagtttggag atgctggcca gtacacctgt cacaaggagc gaggttct aagccattcg      300
ctcctgctgc ttcacaaaaa ggaagatgga atttggtcca ctgatatttt aaaggaccag     360
aaagaaccca aaataagac ctttctaaga tgcgaggcca agaattattc tggacgtttc      420
acctgctggt ggctgacgac aatcagtact gatttgacat tcagtgtcaa agcagcaga     480
ggctcttctg acccccaagg ggtgacgtgc ggagctgcta cactctctgc agagagagtc     540
agaggggaca caaggagta tgagtactca gtggagtgcc aggaggacag tgcctgccca      600
gctgctgagg agagtctgcc cattgaggtc atggtggatg ccgttcacaa gctcaagtat     660
gaaaactaca ccagcagctt cttcatcagg acatcatca aacctgaccc acccaagaac     720
ttgcagctga agccattaaa gaattctcgg caggtggagg tcagctggga gtaccctgac     780
acctggagta ctccacattc ctacttctcc ctgacattct gcgttcaggt ccagggcaag     840
agcaagagag aaaagaaaga tagagtcttc acggacaaga cctcagccac ggtcatctgc     900
cgcaaaaatg ccagcattag cgtgcgggcc caggaccgct actatagctc atcttggagc     960
gaatgggcat ctgtgccctg cagttag                                         987
```

<210> SEQ ID NO 8
<211> LENGTH: 328
<212> TYPE: PRT
<213> ORGANISM: Homo sapiens

<400> SEQUENCE: 8

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
               20                  25                  30

Val Glu Leu Asp Trp Tyr Pro Asp Ala Pro Gly Glu Met Val Val Leu
           35                  40                  45

Thr Cys Asp Thr Pro Glu Glu Asp Gly Ile Thr Trp Thr Leu Asp Gln
       50                  55                  60

Ser Ser Glu Val Leu Gly Ser Gly Lys Thr Leu Thr Ile Gln Val Lys
65                  70                  75                  80
```

Glu Phe Gly Asp Ala Gly Gln Tyr Thr Cys His Lys Gly Gly Glu Val
                85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atggactgga cctggatcct gttcctggtg gccgctgcca cacgggtgca cagc          54

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Asp Trp Thr Trp Ile Leu Phe Leu Val Ala Ala Thr Arg Val
1               5                   10                  15

His Ser

<210> SEQ ID NO 11

```
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

Met Asp Trp Thr Trp Ile Leu Phe Leu Val Ala Ala Thr Arg Val
1               5                   10                  15

His Ser Glu Ser Lys Asp Ala Ser Ser Ala Thr Ser Ile Asp Gln
            20                  25                  30

Leu Cys Lys Thr Phe Asn Leu Ser Leu His Thr Leu Gln Ile Gln Cys
        35                  40                  45

Val Phe Cys Arg Asn Ala Leu Thr Thr Ala Glu Ile Tyr Ala Tyr Ala
    50                  55                  60

Tyr Lys Asn Leu Lys Val Val Trp Arg Asp Asn Phe Pro Phe Ala Ala
65                  70                  75                  80

Cys Ala Cys Cys Leu Glu Leu Gln Gly Lys Ile Asn Gln Tyr Arg His
                85                  90                  95

Phe Asn Tyr Ala Ala Tyr Ala Pro Thr Val Glu Glu Glu Thr Asn Glu
            100                 105                 110

Asp Ile Leu Lys Val Leu Ile Arg Cys Tyr Leu Cys His Lys Pro Gln
        115                 120                 125

Cys Glu Ile Glu Lys Leu Lys His Ile Leu Gly Lys Ala Arg Phe Ile
130                 135                 140

Lys Leu Asn Asn Gln Arg Lys Gly Arg Cys Leu His Cys Trp Thr Thr
145                 150                 155                 160

Cys Met Glu Asp Leu Leu Pro Arg Gly Arg Lys Arg Arg Ser Gly Ser
                165                 170                 175

Gly Ala Thr Asn Phe Ser Leu Leu Lys Gln Ala Gly Asp Val Glu Glu
            180                 185                 190

Asn Pro Gly Pro His Gly Arg Leu Val Thr Leu Lys Asp Ile Val Leu
        195                 200                 205

Asp Leu Gln Pro Pro Asp Pro Val Gly Leu His Ala Tyr Glu Gln Leu
    210                 215                 220

Glu Asp Ser Ser Glu Asp Glu Val Asp Lys Val Asp Lys Gln Asp Ser
225                 230                 235                 240

Gln Pro Leu Thr Gln His Tyr Gln Ile Leu Thr Cys Cys Cys Gly Cys
                245                 250                 255

Asp Ser Asn Val Arg Leu Val Val Glu Cys Thr Asp Gly Asp Ile Arg
            260                 265                 270

Gln Leu Gln Asp Leu Leu Leu Gly Thr Leu Asn Ile Val Cys Pro Ile
        275                 280                 285

Cys Ala Pro Lys Pro Arg Gly Arg Lys Arg Arg Ser Gly Ser Gly Ala
    290                 295                 300

Thr Asn Phe Ser Leu Leu Lys Gln Ala Gly Asp Val Glu Glu Asn Pro
305                 310                 315                 320

Gly Pro Glu Ser Ala Asn Ala Ser Thr Ser Ala Thr Thr Ile Asp Gln
                325                 330                 335

Leu Cys Lys Thr Phe Asn Leu Ser Met His Thr Leu Gln Ile Asn Cys
            340                 345                 350

Val Phe Cys Lys Asn Ala Leu Thr Thr Ala Glu Ile Tyr Ser Tyr Ala
        355                 360                 365

Tyr Lys Gln Leu Lys Val Leu Phe Arg Gly Gly Tyr Pro Tyr Ala Ala

```
                    370                 375                 380
Cys Ala Cys Cys Leu Glu Phe His Gly Lys Ile Asn Gln Tyr Arg His
385                 390                 395                 400

Phe Asp Tyr Ala Gly Tyr Ala Thr Thr Val Glu Glu Thr Lys Gln
                405                 410                 415

Asp Ile Leu Asp Val Leu Ile Arg Cys Tyr Leu Cys His Lys Pro Gln
            420                 425                 430

Cys Glu Val Glu Lys Val Lys His Ile Leu Thr Lys Ala Arg Phe Ile
                435                 440                 445

Lys Leu Asn Cys Thr Arg Lys Gly Arg Cys Leu His Cys Trp Thr Thr
            450                 455                 460

Cys Met Glu Asp Met Leu Pro Arg Gly Arg Lys Arg Arg Ser Gly Ser
465                 470                 475                 480

Gly Ala Thr Asn Phe Ser Leu Leu Lys Gln Ala Gly Asp Val Glu Glu
                485                 490                 495

Asn Pro Gly Pro His Gly Arg His Val Thr Leu Lys Asp Ile Val Leu
            500                 505                 510

Asp Leu Gln Pro Pro Asp Pro Val Gly Leu His Ala Tyr Glu Gln Leu
            515                 520                 525

Val Asp Ser Ser Glu Asp Glu Val Asp Glu Val Asp Gly Gln Asp Ser
530                 535                 540

Gln Pro Leu Lys Gln His Tyr Gln Ile Val Thr Cys Cys Cys Gly Cys
545                 550                 555                 560

Asp Ser Asn Val Arg Leu Val Val Gln Cys Thr Glu Thr Asp Ile Arg
            565                 570                 575

Glu Val Gln Gln Leu Leu Leu Gly Thr Leu Asn Ile Val Cys Pro Ile
            580                 585                 590

Cys Ala Pro Lys Thr
        595

<210> SEQ ID NO 12
<211> LENGTH: 1797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggattgga cctggattct ctttctcgtt gccgctgcta ctcgcgttca tagtgagagc        60
aaggatgcca gcacaagcgc caccagcatc gaccagcttt gcaagacctt taacctgagc      120
ctgcacacac ttcagatcca gtgtgtcttc tgccgaaatg ctctgacaac agcagaaatc      180
tacgcctacg cctacaaaaa cctgaaggtg gtgtggagag acaactttcc tttcgctgcc      240
tgcgcttgct gcctggagct gcagggcaag atcaatcagt accggcactt caactacgct      300
gcctacgccc ctacagtgga ggaggaaaca aacgaagaca tcctgaaggt gctgatcaga      360
tgctacctct gccacaagcc acagtgtgaa atcgagaagc tgaagcacat tctgggcaag      420
gccagattta tcaagctgaa caaccagaga aagggaagat gtctgcactg ttggacaacc      480
tgcatggagg acctgctgcc agaggcagaa agaagagat ctggcagcgg agctaccaac      540
ttctctctgc tgaagcaggc tggagatgtt gaggagaacc caggccctca cggccggctg      600
gtcaccctga aggatatcgt gctggatctg cagccccctg atcctgtggg ccttcacgcc      660
tacgaacagc tggaggacag ctctgaagac gaagtggaca aggtggacaa gcaggactct      720
```

```
cagcctctga cacagcacta tcagatcctg acctgctgct gcggctgtga ctctaacgtg    780
agactggtgg tggagtgcac cgatggagac atcagacagc tgcaggacct gctgctgggt    840
accctgaaca ttgtgtgtcc tatctgtgct ccaaagccaa gaggcaggaa aagaagatcc    900
ggcagcggag ccaccaattt ctccctgctg aagcaagctg gagatgtgga ggagaaccct    960
ggccctgaga gcgccaacgc cagcacatcc gccaccacca tcgaccagct gtgcaagacc   1020
ttcaacctga gcatgcacac actgcagatc aactgtgtct tctgcaagaa tgccctgacc   1080
acagcagaga tctacagcta cgcctacaag cagctgaagg tgctgttcag aggcggctac   1140
ccttatgctg cctgtgcctg ctgcctggag ttccacggca agatcaacca gtacagacac   1200
ttcgactacg ctggctacgc caccacagtg gaagaggaaa caaagcagga catcctggac   1260
gtgctgatcc gatgctacct gtgccacaag cctcagtgtg aagtggaaaa agtgaagcac   1320
atcctgacca aggccagatt catcaagctg aactgcacca gaaaaggcag atgcctgcac   1380
tgctggacca cctgcatgga agacatgctg cctagaggca gaaaagaag aagcggctct   1440 ggagccacca acttttccct gctgaaacaa gctggagacg tggaggaaaa ccctggccct   1500
cacggcagac acgtgacact gaaggacatc gtgctggacc tgcagcctcc tgaccctgtg   1560
ggcctgcacc cctacgagca gctggtggac agcagcgagg acgaagtgga cgaagtggat   1620
ggccaggaca gccagcctct gaagcagcac taccagatcg tcacctgctg ctgtggctgt   1680
gatagcaatg tgaggctggt ggtgcagtgc acagaaacag acatcagaga agtgcagcaa   1740
ctgctgctgg gcaccctgaa catcgtgtgt cccatctgtg ctcccaagac atgataa     1797
```

VACCINES FOR RECURRENT RESPIRATORY PAPILLOMATOSIS AND METHODS OF USING THE SAME

CROSS-REFERENCE TO RELATED APPLICATIONS

This application claims the benefit of U.S. Provisional Application No. 63/024,912, filed May 14, 2020, the contents of which are incorporated herein in their entirety.

SEQUENCE LISTING

The instant application contains a Sequence Listing which has been submitted electronically in ASCII format and is hereby incorporated by reference in its entirety. Said ASCII copy, created on May 14, 2021, is named 104409_000619_US_SL.txt and is 37,912 bytes in size.

TECHNICAL FIELD

The present invention relates to human papillomavirus (HPV) vaccines, methods of inducing immune responses, and methods for prophylactically and/or therapeutically immunizing individuals against HPV6 and/or HPV11, and methods of preventing or treating recurrent respiratory papillomatosis (RRP).

BACKGROUND

Human Papilloma Virus-associated (HPV+) malignancies are an emerging global epidemic (Gradishar et al., *JNCCN* 2014; 12(4):542-90). HPV-associated aerodigestive precancerous lesions and malignancies may occur in the oropharynx, larynx, and upper respiratory tract. While the roles of HPV6 and HPV11 in the etiology of a majority of aerodigestive malignancies remain unclear, they are widely accepted as being causally implicated in recurrent respiratory papillomatosis (RRP) (Mounts et al., *PNAS USA* 1982; 79(17):5425-9; Gissmann et al., *PNAS USA* 1983; 80(2): 560-3; Bonagura et al., *APMIS*. 2010; 118(6-7):455-70), the most common benign tumor of the laryngeal epithelium. RRP is rare, with an incidence rate estimated at 1.8 per 100,000 adults in the United States (Winton et al., *NEJM* 2005; 352(25):2589-97). Although most lesions are benign, some undergo malignant transformation, and patients with RRP have a higher risk of developing laryngeal neoplasias and carcinomas (Omland et al., *PloS One*. 2014; 9(6): e99114).

Recurrent respiratory papillomatosis remains a challenging disease afflicting children and adults, resulting in an estimated $120 million per year in United States healthcare-related costs, with annual costs per patient approaching $60,000. Although the prevalence of RRP has declined, RRP remains the most common benign laryngeal neoplasm in children. RRP is unique in its high rate of multisite recurrence, its high burden on patient quality of life, and its high associated healthcare costs. Thus, there is a need for improved compositions and methods for treatment or prevention of RRP. The present invention satisfies this unmet need.

SUMMARY

Provided herein are nucleic acid molecules encoding a human papillomavirus (HPV) antigen, the HPV antigen comprising a HPV6 antigenic domain and a HPV11 antigenic domain. In some embodiments, the HPV6 antigenic domain comprises a HPV6 E6 antigenic domain and a HPV6 E7 antigenic domain. In some embodiments, the HPV11 antigenic domain comprises a HPV11 E6 antigenic domain and a HPV11 E7 antigenic domain. The nucleic acid molecules provided herein may encode a HPV antigen comprising: the amino acid sequence of SEQ ID NO:1 or SEQ ID NO: 11; an amino acid sequence that is at least 95% homologous to SEQ ID NO:1 or SEQ ID NO: 11; a fragment of the amino acid sequence of SEQ ID NO:1 or SEQ ID NO: 11; or an amino acid sequence that is at least 95% homologous to a fragment of the amino acid sequence of SEQ ID NO:1 or SEQ ID NO: 11. According to some aspects, the nucleic acid molecules comprise: a nucleotide sequence at least 95% homologous to SEQ ID NO:2 or SEQ ID NO: 12; the nucleotide sequence of SEQ ID NO: 2; or the nucleotide sequence of SEQ ID NO 12.

In some embodiments, the nucleic acid sequence encoding the HPV11 antigenic domain is located 5' to the nucleic acid sequence encoding the HPV6 antigenic domain. In alternative embodiments, the nucleic acid sequence encoding the HPV6 antigenic domain is located 5' to the nucleic acid sequence encoding the HPV11 antigenic domain.

The nucleic acid molecules may include nucleic acid sequence encoding one or more post-translational cleavage sites, one or more translational skipping sites, or both. Such sequence(s) may be included between the nucleic acid sequence encoding the HPV6 antigenic domain and the nucleic acid sequence encoding the HPV11 antigenic domain, between the nucleic acid sequence encoding the HPV6 E6 antigenic domain and the nucleic acid sequence encoding the HPV6 E7 antigenic domain, between the nucleic acid sequence encoding the HPV11 E6 antigenic domain and the nucleic acid sequence encoding the HPV11 E7 antigenic domain, or any combination thereof.

Also provided herein are expression vectors comprising any of the disclosed nucleic acid molecules. In some embodiments, the expression vector is a DNA plasmid. As an example, the expression vector may comprise the nucleotide sequence of SEQ ID NO: 3.

Further disclosed herein are immunogenic proteins comprising a human papillomavirus (HPV) 6 antigenic domain fused to a HPV11 antigenic domain. In some embodiments, the HPV6 antigenic domain comprises HPV6 E6 and HPV6 E7; the HPV11 antigenic domain comprises HPV11 E6 and HPV11 E7; or both. The HPV11 antigenic domain may be located N-terminal or C-terminal to the HPV6 antigenic domain. The immunogenic proteins may contain one or more post-translational cleavage sites, one or more translational skipping sites, or both. Such sites may be located between the HPV6 and HPV11 antigenic domain, between the HPV6 E6 and HPV6 E7 antigenic domains, between the HPV11 E6 and HPV11 E7 antigenic domains, or any combination thereof.

According to some embodiments, the immunogenic protein comprises: the amino acid sequence of SEQ ID NO:1 or SEQ ID NO: 11; an amino acid sequence that is at least 95% homologous to the amino acid sequence of SEQ ID NO:1 or SEQ ID NO: 11; a fragment of the amino acid sequence of SEQ ID NO:1 or SEQ ID NO: 11; or an amino acid sequence that is at least 95% homologous to a fragment of the amino acid sequence of SEQ ID NO:1 or SEQ ID NO: 11.

Also provided herein are compositions comprising the nucleic acid molecules, the expression vectors, the immunogenic proteins, or any combination thereof, and a pharmaceutically acceptable carrier. In some aspects are provided vaccines comprising the nucleic acid molecules, the expression vectors, the immunogenic proteins, or any combination thereof. In some embodiments are provided pharmaceutical compositions comprising the nucleic acid molecules, the expression vectors, the immunogenic proteins, or any combination thereof, and an adjuvant. The adjuvant may be, for example, interleukin 12 (IL12). According to some embodiments, the IL12 is encoded by a nucleic acid molecule, such as an expression vector. In some embodiments, the adjuvant comprises a nucleic acid molecule comprising a nucleotide sequence encoding the p35 subunit of IL-12, the p40 subunit of IL-12, or both. For example, the nucleotide sequence encoding the p35 subunit of IL12 may comprise a nucleotide sequence selected from the group consisting of: a nucleotide sequence that encodes SEQ ID NO: 6; a nucleotide sequence that is at least 95% homologous to a nucleotide sequence that encodes SEQ ID NO: 6; a fragment of a nucleotide sequence that encodes SEQ ID NO: 6; and a nucleotide sequence that is at least 95% homologous to a fragment of a nucleotide sequence that encodes SEQ ID NO: 6. In some aspects, the nucleotide sequence encoding the p40 subunit of IL12 comprises a nucleotide sequence selected from the group consisting of: a nucleotide sequence that encodes SEQ ID NO: 8; a nucleotide sequence that is at least 95% homologous to a nucleotide sequence that encodes SEQ ID NO: 8; a fragment of a nucleotide sequence that encodes SEQ ID NO: 8; and a nucleotide sequence that is at least 95% homologous to a fragment of a nucleotide sequence that encodes SEQ ID NO: 8. According to some embodiments, the nucleotide sequence encoding IL12 comprises a nucleotide sequence selected from the group consisting of: the nucleotide sequence of SEQ ID NO: 4; a nucleotide sequence that is at least 95% homologous to the nucleotide sequence of SEQ ID NO: 4; a fragment of the nucleotide sequence of SEQ ID NO: 4; and a nucleotide sequence that is at least 95% homologous to a fragment of the nucleotide sequence of SEQ ID NO: 4.

Further described herein are methods of inducing an immune response in a subject by administering to the subject an effective amount of any of the disclosed nucleic acid molecules, expression vectors, immunogenic proteins, pharmaceutical compositions, or vaccines, to thereby induce the immune response.

Also provided herein are methods of prophylactically or therapeutically immunizing a subject against HPV6 and/or HPV11 comprising administering to the subject an effective amount of any of the disclosed nucleic acid molecules, expression vectors, immunogenic proteins, pharmaceutical compositions, or vaccines, to thereby induce an immune response against HPV6, HPV11, or both.

Additionally provided herein are methods for treating or preventing recurrent respiratory papillomatosis (RRP) in a subject comprising administering to the subject an effective amount of any of the disclosed nucleic acid molecules, expression vectors, immunogenic proteins, pharmaceutical compositions, or vaccines, to thereby treat or prevent RRP. The RRP may be juvenile-onset RRP or adult-onset RRP.

According to some embodiments of the disclosed methods, a nucleic acid molecule comprising the nucleotide sequence of SEQ ID NO: 2, SEQ ID NO: 3, or SEQ ID NO: 12 is administered to the subject.

In some aspects of the disclosed methods, an adjuvant is further administered to the subject. The adjuvant may be interleukin-12 (IL12). The IL12 may be encoded by a nucleic acid molecule, such as, for example, an expression vector or plasmid. In some embodiments, the adjuvant comprises a nucleic acid molecule comprising a nucleotide sequence encoding the p35 subunit of IL-12, the p40 subunit of IL-12, or both. The nucleotide sequence encoding p35 may comprise a nucleotide sequence selected from the group consisting of: a nucleotide sequence that encodes SEQ ID NO: 6; a nucleotide sequence that is at least 95% homologous to a nucleotide sequence that encodes SEQ ID NO: 6; a fragment of a nucleotide sequence that encodes SEQ ID NO: 6; and a nucleotide sequence that is at least 95% homologous to a fragment of a nucleotide sequence that encodes SEQ ID NO: 6. The nucleotide sequence encoding p40 may comprise a nucleotide sequence selected from the group consisting of: a nucleotide sequence that encodes SEQ ID NO: 8; a nucleotide sequence that is at least 95% homologous to a nucleotide sequence that encodes SEQ ID NO: 8; a fragment of a nucleotide sequence that encodes SEQ ID NO: 8; and a nucleotide sequence that is at least 95% homologous to a fragment of a nucleotide sequence that encodes SEQ ID NO: 8. According to some aspects, the nucleotide sequence encoding IL12 may comprise a nucleotide sequence selected from the group consisting of: the nucleotide sequence of SEQ ID NO: 4; a nucleotide sequence that is at least 95% homologous to the nucleotide sequence of SEQ ID NO: 4; a fragment of the nucleotide sequence of SEQ ID NO: 4; and a nucleotide sequence that is at least 95% homologous to a fragment of the nucleotide sequence of SEQ ID NO: 4. According to some embodiments, the nucleic acid molecule comprising a nucleotide sequence encoding IL12 is pGX6010.

In some embodiments, the subject is human.

According to some embodiments of the methods provided herein, the methods comprise administering pGX3024 and pGX6010 to the subject. In some aspects of the methods, the pGX3024 and pGX6010 are administered as a composition, for example, as INO-3107. Some embodiments of the methods comprises administering 6 milligrams pGX3024 and 0.25 milligrams pGX6010 to the subject. In some aspects of the disclosed methods, the administering comprises intradermal or intramuscular injection. The administering may further comprises electroporation.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the thereof; however, the methods are not limited to the specific embodiments disclosed. In the drawings:

FIG. 2 illustrates pGX3024 E6 and E7 protein antigen expression in vitro. HEK-293T cells were transfected with either pGX3024 plasmid, positive control pGX3021 or pGX3022 plasmid, or negative control empty pGX0001 plasmid using Lipofectamine 3000 transfection reagent. Cells were harvested 48 hours post-transfection and cell lysates were then probed with anti-HPV11 E7 (left panel) or anti-2A (middle panel) antibodies by Western blot. Blots were stripped and reprobed with anti-β-actin antibody (right panel) to confirm equal protein loading. E6 and E7 proteins were detected in cells transfected with pGX3024 and control pGX3021 and pGX3022 plasmids, but not negative control pGX0001 plasmid.

DETAILED DESCRIPTION OF ILLUSTRATIVE EMBODIMENTS

Figure 1A:
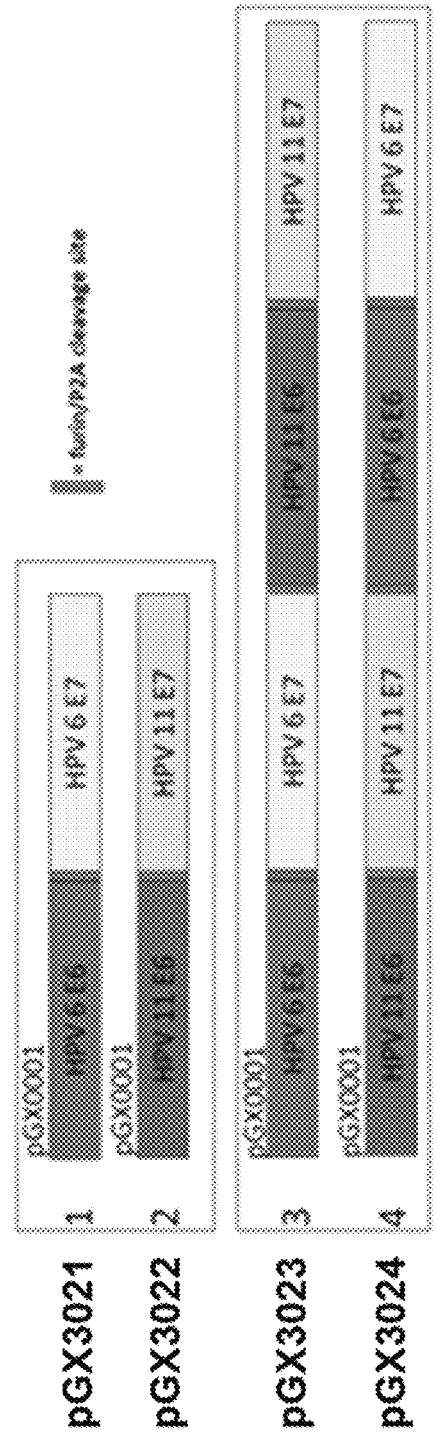
FIG. 1A shows a schematic of antigens encoded in different HPV6 and/or HPV11 plasmids. Individual antigens are separated by a P2A cleavage site for translational skipping and a furin cleavage site for post-translational cleavage of the P2A sequence. DNA plasmid pGX3024 encodes consensus SynCon® E6 and E7 antigens of both HPV6 and HPV11.

The disclosed nucleic acid molecules, proteins, vaccines, and methods may be understood more readily by reference to the following detailed description taken in connection with the accompanying figures, which form a part of this disclosure. It is to be understood that the disclosed nucleic acid molecules, proteins, vaccines, and methods are not limited to the specific nucleic acid molecules, proteins, vaccines, and methods described and/or shown herein, and that the terminology used herein is for the purpose of describing particular embodiments by way of example only and is not intended to be limiting of the claimed nucleic acid molecules, proteins, vaccines, and methods.

Unless specifically stated otherwise, any description as to a possible mechanism or mode of action or reason for improvement is meant to be illustrative only, and the disclosed nucleic acid molecules, proteins, vaccines, and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

It is to be appreciated that certain features of the disclosed nucleic acid molecules, proteins, vaccines, and methods which are, for clarity, described herein in the context of separate embodiments, may also be provided in combination in a single embodiment. Conversely, various features of the disclosed nucleic acid molecules, proteins, vaccines, and methods that are, for brevity, described in the context of a single embodiment, may also be provided separately or in any subcombination.

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The term "comprising" is intended to include examples encompassed by the terms "consisting essentially of" and "consisting of"; similarly, the term "consisting essentially of" is intended to include examples encompassed by the term "consisting of" The present disclosure also contemplates other embodiments "comprising," "consisting of," and "consisting essentially of" the embodiments or elements presented herein, whether explicitly set forth or not.

The singular forms "a," "and" and "the" include plural references unless the context clearly dictates otherwise.

For recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Some of the quantitative expressions given herein are not qualified with the term "about". It is understood that, whether the term "about" is used explicitly or not, every quantity given is intended to refer to the actual given value, and it is also meant to refer to the approximation to such given value that would reasonably be inferred based on the ordinary skill in the art, including approximations due to the experimental and/or measurement conditions for such value.

"Adjuvant" as used herein means any molecule added to the immunogenic compositions described herein to enhance the immunogenicity of the antigens and antigen-encoding nucleic acid molecules and sequences described hereinafter.

"Antigen" refers to proteins having an HPV6 E6 domain, HPV6 E7 domain, HPV11 E6 domain, HPV11 E7 domain, or any combination thereof, and preferably a fusion protein of an HPV6 E6 domain, HPV6 E7 domain, HPV11 E6 domain, and HPV11 E7 domain with an endeoproteolytic cleavage site between each domain. Antigens include SEQ ID NO: 1; fragments thereof of lengths set forth herein, variants, i.e. proteins with sequences homologous to SEQ ID NO: 1 as set forth herein, fragments of variants having lengths set forth herein, and combinations thereof. Antigens may have an IgE leader sequence of SEQ ID NO:10 or may alternatively have such sequence removed from the N-terminal end. For example, an HPV antigen comprising an HPV6 E6 domain, HPV6 E7 domain, HPV11 E6 domain, and HPV11 E7 domain, with or without an endeoproteolytic cleavage site between each domain, may have an IgE leader sequence located N-terminal to the N-terminal HPV domain of the HPV antigen. Antigens may optionally include signal peptides such as those from other proteins.

The term "biosimilar" (of an approved reference product/biological drug, i.e., reference listed drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is to be expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extent the mechanisms are known for the reference product. The condition or conditions of use prescribed, recommended, or suggested in the labeling proposed for the biosimilar have been previously approved for the reference product. The route of administration, the dosage form, and/or the strength of the biosimilar are the same as those of the reference product and the biosimilar is manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein refers to a nucleic acid molecule that has Watson-Crick (e.g., A-T/U and C-G) or Hoogsteen base pairing between nucleotides or nucleotide analogs with a reference nucleic acid molecule.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Immunogenic compositions comprising proteins that comprise consensus sequences and/or nucleic acid molecules that encode such proteins can be used to induce broad immunity against an antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acid sequences below. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein sequence disclosed herein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operably linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used herein, "INO-3107" refers to an immunogenic composition of two DNA plasmids: a DNA plasmid pGX3024 encoding an HPV antigen comprising SynCon® E6 and E7 antigens of both HPV6 and HPV11 in combination with DNA plasmid pGX6010 encoding human IL-12. The amino acid sequence of the HPV antigen comprising SynCon® E6 and E7 antigens of both HPV6 and HPV11 is provided in SEQ ID NO: 1. The nucleotide sequence encoding the HPV antigen comprising SynCon® E6 and E7 antigens of both HPV6 and HPV11 is provided in SEQ ID NO: 2. The nucleic acid sequence of DNA plasmid pGX3024 is set forth in SEQ ID NO: 3. The sequence of DNA plasmid pGX6010 is set forth in SEQ ID NO: 4. "INO-3107" may further include saline-sodium citrate buffer. "INO-3107 drug product" refers to an immunogenic composition containing 6.25 mg total plasmid/mL (6 mg/mL pGX3024, 0.25 mg/mL pGX6010) in 150 mM sodium chloride and 15 mM sodium citrate, pH 7.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double-stranded or can contain portions of both double-stranded and single-stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein can facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used herein, the expression "a subject in need thereof" means a human or non-human mammal that exhibits one or more symptoms or indications of recurrent respiratory papillomatosis (RRP), and/or who has been diagnosed with RRP, and who needs treatment for the same. In many embodiments, the term "subject" may be interchangeably used with the term "patient". For example, a human subject may be diagnosed with RRP and/or with one or more symptoms or indications including, but not limited to, hoarseness, weak cry, chronic coughing, breathing problems, dyspnea, recurrent upper respiratory tract infections, pneumonia, dysphagia, stridor, failure to thrive, and/or respiratory tumors. For example, the expression includes subjects who have been newly diagnosed. In some embodiments, the expression includes subjects for whom treatment in accordance with the disclosed methods is an initial treatment (e.g., "first line" treatment, wherein the patient has not received prior systemic treatment for RRP). In certain embodiments, the expression includes subjects for whom treatment in accordance with the disclosed methods is "second-line" treatment, wherein the patient has been previously treated with "standard-of-care" therapy including, but not limited to surgery, antiviral therapy, and tracheostomy.

As used herein, the term "treat", "treating", or the like, means to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit malignant transformation, and/or to increase duration of survival of the subject.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMA or a corresponding national regulatory agency. For example, proof may be provided by the clinical trial(s) described in the examples provided herein.

The term "clinically proven safe", as it relates to a dose, dosage regimen, treatment or method with a human papillomavirus (HPV) antigen (for example, a HPV antigen administered as pGX3024 or INO-3107 drug product or a biosimilar thereof) refers to a favorable risk:benefit ratio with an acceptable frequency and/or acceptable severity of treatment-emergent adverse events (referred to as TEAEs) compared to the standard of care or to another comparator. An adverse event is an untoward medical occurrence in a patient administered a medicinal product. One index of safety is the National Cancer Institute (NCI) incidence of adverse events (AE) graded per Common Toxicity Criteria for Adverse Events CTCAE v5.0.

The terms "clinically proven efficacy" and "clinically proven effective" as used herein in the context of a dose, dosage regimen, treatment or method refer to the effectiveness of a particular dose, dosage or treatment regimen. Efficacy can be measured based on change in the course of the disease in response to an agent of the present invention. For example, a human papillomavirus (HPV) antigen (for example, a HPV antigen administered as pGX3024 or INO-3107 drug product or a biosimilar thereof) is administered to a patient in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. Improvement may be indicated by an improvement in an index of disease activity, by amelioration of clinical symptoms or by any other measure of disease activity. For example, human papillomavirus (HPV) antigen (for example, a HPV antigen administered as pGX3024 or INO-3107 drug product or a biosimilar thereof) may be administered to achieve an improvement in a patient's condition related to reduced frequency of RRP surgical interventions, a change in RRP Staging Assessment score, increased intersurgical interval, or HPV clearance or reduced disease burden.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto. A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof.

"Variant" with respect to a polypeptide is one that differs in amino acid sequence by the insertion, deletion, or conservative substitution of amino acids, but retains at least one biological activity of the reference polypeptide. Variant can also mean a protein with an amino acid sequence that is substantially identical to a reference protein with an amino acid sequence that retains at least one biological activity. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and in one embodiment, is an expression plasmid. The vector can contain or include one or more heterologous nucleic acid sequences.

As used herein, the phrase "in combination with" means that the HPV6 E6 and E7 antigens and HPV11 E6 and E7 antigens are administered to the subject at the same time as, just before, or just after administration of the adjuvant. In certain embodiments, the HPV6 E6 and E7 antigens and HPV11 E6 and E7 antigens are administered as a co-formulation with the adjuvant.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMA or a corresponding national regulatory agency. For example, proof may be provided by the clinical trial described in the example provided herein.

The term "clinically proven safe", as it relates to a dose, dosage regimen, treatment or method with HPV6 E6 and E7 antigens and HPV11 E6 and E7 antigens (for example, administered as pGX3024) in combination with the adjuvant, such as IL-12 (for example, administered as pGX6010), refers to a favorable risk:benefit ratio with an acceptable frequency and/or acceptable severity of treatment-emergent adverse events (referred to as AEs or TEAEs) compared to the standard of care or to another comparator. An adverse event is an untoward medical occurrence in a subject administered a medicinal product.

The terms "clinically proven efficacy" and "clinically proven effective" as used herein in the context of a dose, dosage regimen, treatment or method refer to the effectiveness of a particular dose, dosage or treatment regimen. Efficacy can be measured based on change in the course of the disease in response to an agent of the present invention. For example, a combination of HPV6 E6 and E7 antigens and HPV11 E6 and E7 antigens (for example, administered as pGX3024) with an adjuvant, such as IL-12 (for example, administered as pGX6010) is administered to a subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. The degree of improvement generally is determined by a physician, who may make this determination based on signs, symptoms, biopsies, or other test results, and who may also employ questionnaires that are administered to the subject, such as quality-of-life questionnaires developed for a given disease. For example, the combination of HPV6 E6 and E7 antigens and HPV11 E6 and E7 antigens (for example, administered as pGX3024) with the adjuvant, such as IL-12 (for example, administered as pGX6010), may be administered to achieve an improvement in a patient's condition related to RRP. Improvement may be indicated by an improvement in an index of disease activity, by amelioration of clinical symptoms or by any other measure of disease activity.

Provided herein are nucleic acid molecules, proteins, immunogenic compositions, including vaccines, and methods of their use to induce an immune response and/or prevent or treat RRP. The immunogenic compositions preferably include a human papillomavirus (HPV) antigen comprising a HPV6 E6 antigenic domain, a HPV6 E7 antigenic domain, a HPV11 E6 antigenic domain, and a HPV11 E7 antigenic domain. The disclosed immunogenic compositions arise from a multi-phase strategy in which modified consensus sequences were generated and genetic modifications, including codon optimization, RNA optimization, and the addition of a high efficient immunoglobin leader sequence, were made. The immunogenic compositions can be used to protect against multiple strains of HPV, thereby treating, preventing, and/or protecting against HPV-based pathologies. In particular, the immunogenic compositions can be used to prevent or treat HPV6- and/or HPV11-based pathologies. The immunogenic compositions can significantly induce an immune response of a subject administered the immunogenic composition, thereby protecting against and treating HPV6 infection, HPV11 infection, or both.

The vaccine can be a DNA vaccine, a peptide vaccine, or a combination DNA and peptide vaccine. The DNA vaccine can include a nucleic acid sequence encoding the HPV antigen. The nucleic acid sequence can be DNA, RNA, cDNA, a variant thereof, a fragment thereof, or a combination thereof. The nucleic acid sequence can also include additional sequences that encode linker, leader, or tag sequences that are linked to the HPV antigen by a peptide bond. The peptide vaccine can include a HPV antigenic peptide, a HPV antigenic protein, a variant thereof, a fragment thereof, or a combination thereof. The combination DNA and peptide vaccine can include the above described nucleic acid sequence encoding the HPV antigen and the HPV antigenic peptide or protein, in which the HPV antigenic peptide or protein and the encoded HPV antigen have the same amino acid sequence.

The vaccine can induce a humoral immune response in the subject administered the vaccine. The induced humoral immune response can be specific for the HPV6 E6 antigenic domain, the HPV6 E7 antigenic domain, the HPV11 E6 antigenic domain, the HPV11 E7 antigenic domain, or any combination thereof. The induced humoral immune response can be reactive with the HPV6 E6 antigen, the HPV6 E7 antigen, the HPV11 E6 antigen, the HPV11 E7 antigen, or any combination thereof. The humoral immune response can be induced in the subject administered the vaccine by about 1.5-fold to about 16-fold, about 2-fold to about 12-fold, or about 3-fold to about 10-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold.

The humoral immune response induced by the vaccine can include an increased level of IgG antibodies associated with the subject administered the vaccine as compared to a subject not administered the vaccine. These IgG antibodies can be specific for the HPV6 E6 antigen, the HPV6 E7 antigen, the HPV11 E6 antigen, the HPV11 E7 antigen, or any combination thereof. These IgG antibodies can be reactive with the HPV6 E6 antigen, the HPV6 E7 antigen, the HPV11 E6 antigen, the HPV11 E7 antigen, or any combination thereof. The level of IgG antibody associated with the subject administered the vaccine can be increased by about 1.5-fold to about 16-fold, about 2-fold to about 12-fold, or about 3-fold to about 10-fold as compared to the subject not administered the vaccine. The level of IgG antibody associated with the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to the subject not administered the vaccine.

The vaccine can induce a cellular immune response in the subject administered the vaccine. The induced cellular immune response can be specific for the HPV6 E6 antigen, the HPV6 E7 antigen, the HPV11 E6 antigen, the HPV11 E7 antigen, or any combination thereof. The induced cellular immune response can be reactive to the HPV6 E6 antigen, the HPV6 E7 antigen, the HPV11 E6 antigen, the HPV11 E7 antigen, or any combination thereof. The induced cellular immune response can include eliciting a T cell response. The elicited T cell response can be reactive with the HPV6 E6 antigen, the HPV6 E7 antigen, the HPV11 E6 antigen, the HPV11 E7 antigen, or any combination thereof. The elicited T cell response can be polyfunctional. The induced cellular immune response can include eliciting a T cell response, in which the T cells produce interferon-gamma (IFN-γ). The induced cellular immune response can include an increased T cell response associated with the subject administered the vaccine as compared to the subject not administered the vaccine. The T cell response associated with the subject administered the vaccine can be increased by about 2-fold to about 30-fold, about 3-fold to about 25-fold, or about 4-fold to about 20-fold as compared to the subject not administered the vaccine. The T cell response associated with the subject administered the vaccine can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to the subject not administered the vaccine.

The vaccine of the present invention can have features required of effective vaccines such as being safe so the vaccine itself does not cause illness or death; is protective against illness resulting from exposure to live pathogens such as viruses or bacteria; induces antibody to prevent invention of cells; induces protective T cells against intracellular pathogens; and provides ease of administration, few side effects, biological stability, and low cost per dose.

The vaccine can further induce an immune response when administered to different tissues such as the muscle or skin. The vaccine can further induce an immune response when administered via electroporation, or injection, or subcutaneously, or intramuscularly.

The HPV antigen is capable of eliciting an immune response in a mammal against one or more HPV strains. Thus disclosed herein are HPV antigens comprising a HPV6 antigenic domain and a HPV11 antigenic domain. The HPV6 antigenic domain may be located N-terminal or C-terminal to the HPV11 antigenic domain.

In some embodiments, the HPV6 antigenic domain comprises an HPV6 E6 antigenic domain, a fragment thereof, or a variant thereof and an HPV6 E7 antigenic domain, a fragment thereof, a variant thereof, or a combination thereof. The HPV6 E6 antigenic domain may be located N-terminal or C-terminal to the HPV6 E7 antigenic domain. In some embodiments, the HPV6 E6 antigenic domain can comprise an epitope(s) that makes it particularly effective as an immunogen against which an immune response can be induced. The HPV6 E6 antigenic domain can be a consensus sequence derived from two or more strains of HPV6. The HPV6 E6 antigenic domain can comprise a consensus sequence and/or modification(s) for improved expression. Modification can include codon optimization, RNA optimization, addition of a kozak sequence for increased translation initiation, and/or the addition of an immunoglobulin leader sequence to increase the immunogenicity of the HPV6 E6 antigenic domain. The HPV6 E6 consensus antigenic domain can comprise a signal peptide such as an immunoglobulin signal peptide, for example, but not limited to, an immunoglobulin E (IgE) or immunoglobulin (IgG) signal peptide. In some embodiments, the HPV6 E6 consensus antigenic domain can comprise a hemagglutinin (HA) tag. The HPV6 E6 consensus antigenic domain can be designed to elicit stronger and broader cellular and/or humoral immune responses than a corresponding codon optimized HPV6 E6 antigenic domain. In some embodiments, the HPV6 E7 antigenic domain can comprise an epitope(s) that makes it particularly effective as an immunogen against which an immune response can be induced. The HPV6 E7 antigenic domain can be a consensus sequence derived from two or more strains of HPV6. The HPV6 E7 antigenic domain can comprise a consensus sequence and/or modification(s) for improved expression. Modification can include codon optimization, RNA optimization, addition of a kozak sequence for increased translation initiation, and/or the addition of an immunoglobulin leader sequence to increase the immunogenicity of the HPV6 E7 antigenic domain. The HPV6 E7 consensus antigenic domain can comprise a signal peptide such as an immunoglobulin signal peptide, for example, but not limited to, an immunoglobulin E (IgE) or immunoglobulin (IgG) signal peptide. In some embodiments, the HPV6 E7 consensus antigenic domain can comprise a hemagglutinin (HA) tag. The HPV6 E7 consensus antigenic domain can be designed to elicit stronger and broader cellular and/or humoral immune responses than a corresponding codon optimized HPV6 E7 antigenic domain.

In some embodiments, the HPV11 antigenic domain comprises an HPV11 E6 antigenic domain, a fragment thereof, or a variant thereof and an HPV11 E7 antigenic domain, a fragment thereof, a variant thereof, or a combination thereof. The HPV11 E6 antigenic domain may be positioned N-terminal or C-terminal to the HPV11 E7 antigenic domain. In some embodiments, the HPV11 E6 antigenic domain can comprise an epitope(s) that makes it particularly effective as an immunogen against which an immune response can be induced. The HPV11 E6 antigenic domain can be a consensus sequence derived from two or more strains of HPV11. The HPV11 E6 antigenic domain can comprise a consensus sequence and/or modification(s) for improved expression. Modification can include codon optimization, RNA optimization, addition of a kozak sequence for increased translation initiation, and/or the addition of an immunoglobulin leader sequence to increase the immunogenicity of the HPV11 E6 antigenic domain. The HPV11 E6 consensus antigenic domain can comprise a signal peptide such as an immunoglobulin signal peptide, for example, but not limited to, an immunoglobulin E (IgE) or immunoglobulin (IgG) signal peptide. In some embodiments, the HPV11 E6 consensus antigenic domain can comprise a hemagglutinin (HA) tag. The HPV11 E6 consensus antigenic domain can be designed to elicit stronger and broader cellular and/or humoral immune responses than a corresponding codon optimized HPV11 E6 antigenic domain. In some embodiments, the HPV11 E7 antigenic domain can comprise an epitope(s) that makes it particularly effective as an immunogen against which an immune response can be induced. The HPV11 E7 antigenic domain can be a consensus sequence derived from two or more strains of HPV11. The HPV11 E7 antigenic domain can comprise a consensus sequence and/or modification(s) for improved expression. Modification can include codon optimization, RNA optimization, addition of a kozak sequence for increased translation initiation, and/or the addition of an immunoglobulin leader sequence to increase the immunogenicity of the HPV11 E7 antigenic domain. The HPV11 E7 consensus antigenic domain can comprise a signal peptide such as an immunoglobulin signal peptide, for example, but not limited to, an immunoglobulin E (IgE) or immunoglobulin (IgG) signal peptide. In some embodiments, the HPV11 E7 consensus antigenic domain can comprise a hemagglutinin (HA) tag. The HPV11 E7 consensus antigenic domain can be designed to elicit stronger and broader cellular and/or humoral immune responses than a corresponding codon optimized HPV11 E7 antigenic domain.

In some aspects, the HPV antigen comprises the amino acid sequence of SEQ ID NO:1 or SEQ ID NO: 11; an amino acid sequence that is at least about 95%, about 96%, about 97%, about 98%, or about 99% homologous to the amino acid sequence of SEQ ID NO:1 or SEQ ID NO: 11; an immunogenic fragment of the amino acid sequence of SEQ ID NO:1 or SEQ ID NO: 11; or an amino acid sequence that is at least about 95%, about 96%, about 97%, about 98%, or about 99% homologous to an immunogenic fragment of the amino acid sequence of SEQ ID NO:1 or SEQ ID NO: 11.

Fragments of the amino acid sequence of SEQ ID NO:1 or SEQ ID NO: 11 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length of the amino acid sequence of SEQ ID NO:1 or SEQ ID NO: 11. Fragments of the amino acid sequence of SEQ ID NO:1 or SEQ ID NO: 11 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length of the amino acid sequence of SEQ ID NO:1 or SEQ ID NO: 11. Fragments of SEQ ID NO:1 or SEQ ID NO: 11 may be 100% identical to the full-length reference sequence except missing at least one amino acid from the N and/or C terminal, in each case with or without signal peptides and/or a methionine at position 1. Fragments of SEQ ID NO:1 or SEQ ID NO: 11 can comprise 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the full length SEQ ID NO:1 or SEQ ID NO: 11, excluding any heterologous signal peptide added. The fragment can, preferably, comprise a fragment of SEQ ID NO:1 or SEQ ID NO: 11 that is 95% or more, 96% or more, 97% or more, 98% or more or 99% or more homologous to SEQ ID NO:1 or SEQ ID NO: 11 and additionally comprise an N terminal methionine or heterologous signal peptide which is not included when calculating percent homology Fragments can further comprise an N-terminal methionine and/or a signal peptide such as an immunoglobulin signal peptide, for example an IgE or IgG signal peptide. The N-terminal methionine and/or signal peptide may be linked to the fragment.

In some embodiments, fragments of SEQ ID NO:1 or SEQ ID NO: 11 may comprise 100 or more residues; in some embodiments, 200 or more residues; in some embodiments 300 or more residues; in some embodiments, 400 or more residues; and in some embodiments 500 or more residues.

In some aspects, the HPV antigen may comprise HPV6 and HPV11 antigenic domains separated by one or more post-translational cleavage sites, one or more translational skipping sites, or both. In some embodiments, a post-translational cleavage site is located between the HPV6 and HPV11 antigen domains, between the HPV6 E6 and E7 antigenic domains, and/or between the HPV11 E6 and E7 antigenic domains. In some embodiments, a translational skipping site is located between the HPV6 and HPV11 antigen domains, between the HPV6 E6 and E7 antigenic domains, and/or between the HPV11 E6 and E7 antigenic domains. In some embodiments, a post-translational cleavage site and a translational skipping site are located between the HPV6 and HPV11 antigen domains, between the HPV6 E6 and E7 antigen domains, and/or between the HPV11 E6 and E7 antigenic domains. In some embodiments, the post-translational cleavage site is a furin cleavage site. In some embodiments, the translational skipping site is a P2A site. In some aspects, the HPV immunogenic protein comprises the amino acid sequence of SEQ ID NO: 1 or SEQ ID NO: 11.

In some aspects, the HPV antigen comprises the amino acid sequence of SEQ ID NO:1 or SEQ ID NO: 11; an amino acid sequence that is at least about 95%, about 96%, about 97%, about 98%, or about 99% homologous to SEQ ID NO:1 or SEQ ID NO: 11; an immunogenic fragment of SEQ ID NO:1 or SEQ ID NO: 11; or an amino acid sequence that is at least about 95%, about 96%, about 97%, about 98%, or about 99% homologous to an immunogenic fragment of SEQ ID NO:1 or SEQ ID NO: 11.

Proteins of the invention may be generated using well known techniques. In some embodiments, for example, DNA molecules that encode a protein of the invention can be inserted into a commercially available expression vector for use in an expression system. The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology. In addition to producing proteins by recombinant techniques, automated peptide synthesizers may also be employed to produce isolated, essentially pure protein.

The HPV antigen can be a nucleic acid molecule that encodes the HPV6-HPV11 fusion antigen disclosed herein. The nucleotide sequence encoding the HPV11 antigenic domain may be located 5' or 3' to the nucleotide sequence encoding the HPV6 antigenic domain.

In some embodiments, the nucleic acid sequence encoding the HPV6 antigenic domain comprises a nucleic acid sequence encoding a HPV6 E6 antigenic domain and a HPV6 E7 antigenic domain. The nucleic acid sequence encoding the HPV6 E6 antigenic domain may be located 5' or 3' to the nucleic acid sequence encoding the HPV6 E7 antigenic domain.

In some embodiments, the nucleic acid sequence encoding the HPV11 antigenic domain comprises a nucleic acid sequence encoding a HPV11 E6 antigenic domain and a HPV11 E7 antigenic domain. The nucleic acid sequence encoding the HPV11 E6 antigenic domain may be located 5' or 3' to the nucleic acid sequence encoding the HPV11 E7 antigenic domain.

In some aspects, nucleotide sequences encoding antigenic domains of the HPV antigen may be separated by nucleotide sequences encoding one or more post-translational cleavage sites, one or more translational skipping sites, or both. In some embodiments, a nucleotide sequence encoding a post-translational cleavage site is located between the nucleotide sequences encoding the HPV6 and HPV11 antigenic domains, between the nucleotide sequences encoding the HPV6 E6 and E7 antigenic domains, between the nucleotide sequences encoding the HPV11 E6 and E7 antigenic domains, or any combination thereof. In some embodiments, nucleotide sequences encoding a translational skipping site is located between the nucleotide sequences encoding the HPV6 and HPV11 antigen domains, between the nucleotide sequences encoding the HPV6 E6 and E7 antigen domains, between the nucleotide sequences encoding the HPV11 E6 and E7 antigenic domains, or any combination thereof. In some embodiments, nucleotide sequences encoding a post-translational cleavage site and a translational skipping site are located between the nucleotide sequences encoding the HPV6 and HPV11 antigenic domains, between the nucleotide sequences encoding the HPV6 E6 and E7 antigenic domains, between the nucleotide sequences encoding the HPV11 E6 and E7 antigenic domains, or any combination thereof. In some embodiments, the post-translational cleavage site is a furin cleavage site. In some embodiments, the translational skipping site is a P2A site.

In some embodiments, the nucleic acid sequence encoding the HPV antigen comprises: the nucleotide sequence of SEQ ID NO:2 or SEQ ID NO: 12; a nucleotide sequence that is at least about 95%, about 96%, about 97%, about 98%, or about 99% homologous to the nucleotide sequence of SEQ ID NO:2 or SEQ ID NO: 12; a fragment of the nucleotide sequence of SEQ ID NO:2 or SEQ ID NO: 12; or a nucleotide sequence that is at least about 95%, about 96%, about 97%, about 98%, or about 99% homologous to a fragment of the nucleotide sequence of SEQ ID NO:2 or SEQ ID NO: 12. Fragments can further comprise coding sequences for an N terminal methionine and/or a signal peptide such as an immunoglobulin signal peptide, for example an IgE or IgG signal peptide. The coding sequence encoding the N-terminal methionine and/or signal peptide may be linked to the fragment.

Nucleic acid molecules that comprise a nucleotide sequence that encodes the immunogen(s) may be operably linked to regulatory elements. The nucleic acid molecule can be DNA, RNA, cDNA, a variant thereof, a fragment thereof, or a combination thereof. The nucleic acid sequence can also include additional sequences that encode linker or tag sequences that are linked to the antigen by a peptide bond.

In some aspects, the nucleic acid molecule encoding the HPV antigen is an expression vector. An expression vector can be a circular plasmid or a linear nucleic acid. An expression vector is capable of directing expression of a particular nucleotide sequence in an appropriate subject cell. An expression vector can have a promoter operably linked to the antigen-encoding nucleotide sequence, which may be operably linked to termination signals. An expression vector can also contain sequences required for proper translation of the nucleotide sequence. The expression vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

In one embodiment, the nucleic acid is an RNA molecule. Accordingly, in one embodiment, the invention provides an RNA molecule encoding one or more polypeptides of interest. The RNA may be plus-stranded. Accordingly, in some embodiments, the RNA molecule can be translated by cells without needing any intervening replication steps such as reverse transcription. An RNA molecule useful with the invention may have a 5' cap (e.g. a 7-methylguanosine). This cap can enhance in vivo translation of the RNA. The 5' nucleotide of an RNA molecule useful with the invention may have a 5' triphosphate group. In a capped RNA this may be linked to a 7-methylguanosine via a 5'-to-5' bridge. An RNA molecule may have a 3' poly-A tail. It may also include a poly-A polymerase recognition sequence (e.g. AAUAAA) near its 3' end. An RNA molecule useful with the invention may be single-stranded. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

The expression vector may be a circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid immunogenic composition, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleotide sequences unrelated to the desired antigen gene expression. The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system. The LEC can be perM2. The LEC can be perNP. perNP and perMR can be derived from pNP (Puerto Rico/34) and pM2 (New Caledonia/99), respectively.

The vector can comprise heterologous nucleic acid encoding the above described antigens and can further comprise an initiation codon, which can be upstream of the one or more cancer antigen coding sequence(s), and a stop codon, which can be downstream of the coding sequence(s) of the above described antigens.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The initiation and termination codon can be in frame with the coding sequence(s) of the above described antigens. The vector can also comprise a promoter that is operably linked to the coding sequence(s) of the above described antigens. The promoter operably linked to the coding sequence(s) of the above described antigens can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metallothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the above described antigens and/or antibodies. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the above described antigens. The enhancer can be necessary for expression. The enhancer can be human actin, human myosin, human hemoglobin, human muscle creatine or a viral enhancer such as one from CMV, HA, RSV or EBV.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

The vector can further comprise elements or reagents that inhibit it from integrating into the chromosome. The vector can comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVAX1 variant with changes such as the variant plasmid described herein. The variant pVax1 plasmid is a 2998 base pair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1:

C>G241 in CMV promoter
C>T 1942 backbone, downstream of the bovine growth hormone polyadenylation signal (bGHpolyA)
A>-2876 backbone, downstream of the Kanamycin gene
C>T 3277 in pUC origin of replication (Ori) high copy number mutation (see Nucleic Acid Research 1985)
G>C 3753 in very end of pUC Ori upstream of RNASeH site Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), incorporated fully herein by reference.

An exemplary DNA plasmid comprises SEQ ID NO: 3.

Immunogenic compositions of the invention may include a HPV antigen of the invention, a recombinant vaccine comprising a nucleotide sequence that encodes a HPV antigen of the invention, a live attenuated pathogen that encodes a HPV antigen of the invention and/or includes a HPV antigen of the invention; a killed pathogen including a HPV antigen of the invention; or a composition such as a liposome or subunit vaccine that comprises a HPV antigen of the invention. The present invention further relates to pharmaceutical compositions, for example but not limited to injectable pharmaceutical compositions, that comprise the disclosed immunogenic compositions.

The immunogenic compositions of the invention may be formulated with suitable pharmaceutically acceptable carriers, excipients, and other agents that provide suitable transfer, delivery, tolerance, and the like. The pharmaceutically acceptable excipient can be functional molecules such as vehicles, carriers, or diluents.

The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The pharmaceutically acceptable excipient may be an adjuvant. In some aspects are provided compositions and vaccines comprising the HPV antigen of the invention in combination with an adjuvant. The adjuvant can be other genes that are expressed in an alternative plasmid or are delivered as proteins in combination with the HPV antigen of the invention. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

In certain embodiments, the adjuvant is interleukin-12 (IL12). IL12 may be included in a vaccine in the form of its p35 and p40 subunits. The adjuvant IL-12 may be administered to the subject as its p35 and p40 subunits. The IL12 p35 and p40 subunits may be encoded by the same expression vector or by separate expression vectors. The nucleic acid molecule encoding the IL12 may the same as or different than the nucleic acid molecule encoding the HPV6 antigen fused to the HPV11 antigen. In some aspects, the nucleic acid molecule encoding IL12 comprises a nucleotide sequence encoding the p35 subunit of IL-12, the p40 subunit of IL-12, or both. The nucleic acid molecule encoding the p35 subunit of IL12 may comprise a nucleotide sequence that encodes SEQ ID NO:6; a nucleotide sequence that is at least about 95%, about 96%, about 97%, about 98%, or about 99% homologous to a nucleotide sequence that encodes SEQ ID NO:6; a fragment of a nucleotide sequence that encodes SEQ ID NO:6; or a nucleotide sequence that is at least about 95%, about 96%, about 97%, about 98%, or about 99% homologous to a fragment of a nucleotide sequence that encodes SEQ ID NO:6. The nucleic acid molecule encoding the p40 subunit of IL12 may comprise a nucleotide sequence that encodes SEQ ID NO:8; a nucleotide sequence that is at least about 95%, about 96%, about 97%, about 98%, or about 99% homologous to a nucleotide sequence that encodes SEQ ID NO: 8; a fragment of a nucleotide sequence that encodes SEQ ID NO:8; or a nucleotide sequence that is at least 95% homologous to a fragment of a nucleotide sequence that encodes SEQ ID NO:8. The nucleic acid molecule encoding the p35 subunit of IL12 may comprise a nucleotide sequence of SEQ ID NO:5; a nucleotide sequence that is at least about 95%, about 96%, about 97%, about 98%, or about 99% identical to the nucleotide sequence of SEQ ID NO:5; a fragment of the nucleotide sequence of SEQ ID NO:5; or a nucleotide sequence that is at least about 95%, about 96%, about 97%, about 98%, or about 99% identical to a fragment of the nucleotide sequence of SEQ ID NO:5. The nucleic acid molecule encoding the p40 subunit of IL12 may comprise a nucleotide sequence of SEQ ID NO:7; a nucleotide sequence that is at least about 95%, about 96%, about 97%, about 98%, or about 99% identical to the nucleotide sequence of SEQ ID NO:7; a fragment of the nucleotide sequence of SEQ ID NO:7; or a nucleotide sequence that is at least about 95%, about 96%, about 97%, about 98%, or about 99% identical to a fragment of the nucleotide sequence of SEQ ID NO:7.

In some embodiments of the described immunogenic compositions, the composition comprises pGX3024 and pGX6010. In some embodiments, the composition is INO-3107.

As used herein, "buffer" refers to a buffered solution that resists changes in pH by the action of its acid-base conjugate components. The buffer generally has a pH from about 4.0 to about 8.0, for example from about 5.0 to about 7.0. In some embodiments, the buffer is saline-sodium citrate (SSC) buffer. In some embodiments in which the immunogenic composition comprises a vector comprising a nucleic acid molecule encoding a HPV antigen as described above, the immunogenic composition comprises 6 mg/ml of vector in buffer, for example but not limited to SSC buffer. In some embodiments, the immunogenic composition comprises 6 mg/mL of the DNA plasmid pGX3024 in buffer. In some embodiments in which the immunogenic composition further comprises a separate vector comprising a nucleic acid molecule encoding the p35 subunit of IL-12, the p40 subunit of IL-12, or both, the immunogenic composition comprises 0.25 mg/ml of the separate vector in the buffer. In some embodiments, the immunogenic composition comprises 0.25 mg/mL of the DNA plasmid pGX6010 in the buffer in addition to the vector comprising a nucleic acid molecule encoding the HPV antigen (e.g., pGX3024).

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Also provided herein are methods of treating, protecting against, and/or preventing disease in a subject in need thereof by administering the vaccine of the invention to the subject. Administration of the vaccine to the subject can induce or elicit an immune response in the subject. Methods of inducing an immune response in a subject comprising administering to the subject an effective amount of the HPV antigen of the invention to thereby induce the immune response are thus provided.

Further provided are methods of prophylactically or therapeutically immunizing a subject against HPV6, HPV11, or both, comprising administering to the subject an effective amount of the HPV antigen of the invention to thereby induce an immune response against HPV6, HPV11, or both. Also provided are methods for treating or preventing recurrent respiratory papillomatosis (RRP) in a subject comprising administering to the subject an effective amount of the HPV antigen of the invention to thereby treat or prevent RRP.

The induced immune response can be used to treat, prevent, and/or protect against disease, for example, pathologies relating to HPV infection. In some embodiments, are provided methods of treating, protecting against, and/or preventing RRP in a subject in need thereof by administering the HPV antigen of the invention to the subject. The induced immune response provides the subject administered the vaccine resistance to one or more HPV strains. The induced immune response can include an induced humoral immune response and/or an induced cellular immune response.

The subject can be a mammal, such as a human, a horse, a cow, a pig, a sheep, a cat, a dog, a rabbit, a guinea pig, a rat, or a mouse.

The vaccine dose can be between 1 µg to 10 mg total plasmid per injection, preferably 6.25 mg total plasmid per injection. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

In some embodiments of the described methods, the subject is administered pGX3024 and pGX6010. In some embodiments, the pGX3024 and pGX6010 are administered to the subject as INO-3107. In some embodiments, the pGX3024 and pGX6010 are administered to the subject as INO-3107 drug product containing 6.25 mg total plasmid/mL (6 mg/mL pGX3024, 0.25 mg/mL pGX6010) in 150 mM sodium chloride and 15 mM sodium citrate, pH 7.

The vaccine can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

According to some embodiments, a vaccine is delivered to an individual to modulate the activity of the individual's immune system and thereby enhance the immune response against HPV to treat RRP. When a nucleic acid molecule that encodes the HPV antigen of the invention is taken up by cells of the individual, the nucleotide sequence is expressed in the cells and the protein are thereby delivered to the individual. Methods of delivering the coding sequences of the protein on nucleic acid molecule such as plasmid, as part of recombinant vaccines and as part of attenuated vaccines, as isolated proteins or proteins part of a vector are provided.

The methods comprise administering to a subject the HPV antigen of the invention. In some aspects, the methods include a step of introducing the provided nucleic acid molecules followed by electroporation.

The disclosed methods may comprise administration of a plurality of copies of a single nucleic acid molecule such as a single plasmid, or a plurality of copies of two or more different nucleic acid molecules such as two or more different plasmids. For example, the methods may comprise administration of two, three, four, five, six, seven, eight, nine or ten or more different nucleic acid molecules.

In certain embodiments, the disclosed methods of inducing an immune response or methods of preventing or treating RRP further comprise administering to the subject an adjuvant. In certain embodiments, the adjuvant is IL12. IL12 may be included in a vaccine in the form of its p35 and p40 subunits. The adjuvant IL-12 may be administered to the subject as its p35 and p40 subunits. The IL12 p35 and p40 subunits may be encoded by the same expression vector or by separate expression vectors. In one embodiment, the IL12 p35 encoding sequence is as set forth in SEQ ID NO:5. In one embodiment, the IL12 p35 subunit has an amino acid sequence as set forth in SEQ ID NO:6. In one embodiment, the IL12 p40 encoding sequence is as set forth in SEQ ID NO:7. In one embodiment, the IL12 p40 subunit has an amino acid sequence as set forth in SEQ ID NO:8. In some embodiments, the expression vector is pGX6012 or pGX6010. In certain embodiments, the methods are clinically proven safe, clinically proven effective, or both.

In some embodiments, the method comprises concurrent administration of: (a) an immunogenic composition comprising a HPV antigen as disclosed herein and (b) a composition comprising a nucleic acid molecule encoding one or more IL-12 subunits (e.g. p35 and/or p40) disclosed herein. In some embodiments, the method comprises administering a composition comprising a nucleic acid molecule encoding one or more IL-12 subunits (e.g. p35 and/or p40) disclosed herein after the prior administration of a composition comprising a nucleic acid molecule encoding a HPV antigen disclosed herein. In some embodiments, the method comprises administering a composition comprising a nucleic acid molecule encoding a HPV antigen disclosed herein after the prior administration of a composition comprising a nucleic acid molecule encoding one or more IL-12 subunit (e.g. p35 and/or p40) disclosed herein.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520, 950; 7,171,264; 6,208,893; 6,009,347; 6,120,493; 7,245, 963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA® (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The CELLECTRA device and system is described in U.S. Pat. No. 7,245,963, the contents of which are herein incorporated by reference. The CELLECTRA® device may be the CELLECTRA 2000® device or CELLECTRA® 3PSP device. The CELLECTRA® 2000 device is configured by the manufacturer to support either ID (intradermal) or IM (intramuscular) administration. The CELLECTRA™ 2000 includes the CELLECTRA™ Pulse Generator, the appropriate applicator, disposable sterile array and disposable sheath (ID only). The DNA plasmid is delivered separately via needle and syringe injection in the area delineated by the electrodes immediately prior to the electroporation treatment.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue. Suitable tissues into which fluid may be injected by the apparatus of the present invention include tumor tissue, skin, or muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

Further provided herein are kits which can be used for treating a subject using the methods of vaccination described above. The kits can comprise the vaccine. The kits can also comprise instructions for carrying out the vaccination method described above and/or how to use the kit. Instructions included in the kit can be affixed to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an internet site which provides instructions.

ILLUSTRATIVE EMBODIMENTS

Embodiment 1. A nucleic acid molecule encoding a human papillomavirus (HPV) antigen, the HPV antigen comprising a HPV6 antigenic domain and a HPV11 antigenic domain.

Embodiment 2. The nucleic acid molecule according to Embodiment 1, wherein the HPV6 antigenic domain is an HPV6 E6-E7 fusion antigen.

Embodiment 3. The nucleic acid molecule according Embodiment 1 or 2, wherein the HPV11 antigenic domain is an HPV11 E6-E7 fusion antigen.

Embodiment 4. The nucleic acid molecule according to any preceding Embodiment, wherein the HPV antigen comprises:
the amino acid sequence of SEQ ID NO:1 or SEQ ID NO: 11; or
an amino acid sequence that is at least 95% homologous to SEQ ID NO:1 or SEQ ID NO: 11.

Embodiment 5. The nucleic acid molecule according to any preceding Embodiment, comprising:
a nucleotide sequence at least 95% homologous to SEQ ID NO:2 or SEQ ID NO: 12;
the nucleotide sequence of SEQ ID NO: 2; or
the nucleotide sequence of SEQ ID NO 12.

Embodiment 6. The nucleic acid molecule according to any preceding Embodiment wherein the nucleic acid sequence encoding the HPV11 antigenic domain is located 5' to the nucleic acid sequence encoding the HPV6 antigenic domain.

Embodiment 7. The nucleic acid molecule according to any preceding Embodiment wherein the HPV6 antigenic domain and the HPV11 antigenic domain are separated by a one or more post-translational cleavage sites, one or more translational skipping sites, or both.

Embodiment 8. The nucleic acid molecule according to Embodiment 2 wherein the HPV6 E6 antigenic domain and the HPV6 E7 antigenic domain are separated by one or more post-translational cleavage sites, one or more translational skipping sites, or both.

Embodiment 9. The nucleic acid molecule according to Embodiment 4 wherein the HPV11 E6 antigenic domain and the HPV11 E7 antigenic domain are separated by one or more post-translational cleavage sites, one or more translational skipping sites, or both.

Embodiment 10. An expression vector comprising the nucleic acid molecule according to any preceding Embodiment.

Embodiment 11. The expression vector of Embodiment 10 comprising a DNA plasmid.

Embodiment 12. The expression vector of Embodiment 10, comprising the nucleotide sequence of SEQ ID NO: 3.

Embodiment 13. An immunogenic protein comprising a human papillomavirus (HPV) 6 antigenic domain and a HPV11 antigenic domain.

Embodiment 14. The immunogenic protein according to Embodiment 14, wherein the HPV6 antigenic domain comprises a HPV6 E6 antigenic domain and a HPV6 E7 antigenic domain.

Embodiment 15. The immunogenic protein according to Embodiment 13 or 14, wherein the HPV11 antigenic domain comprises a HPV11 E6 antigenic domain and a HPV11 E7 antigenic domain.

Embodiment 16. The immunogenic protein according to any one of Embodiments 13 to 15, comprising:
the amino acid sequence of SEQ ID NO:1 or SEQ ID NO: 11; or
an amino acid sequence that is at least 95% homologous to the amino acid sequence of SEQ ID NO:1 or SEQ ID NO: 11.

Embodiment 17. The immunogenic protein according to any one of Embodiments 13 to 16, wherein the HPV11 antigenic domain is located N-terminal to the HPV6 antigen.

Embodiment 18. The immunogenic protein according to any one of Embodiments 13 to 17, wherein the HPV6 antigenic domain and the HPV11 antigenic domain are separated by one or more post-translational cleavage sites, one or more translational skipping sites, or both.

Embodiment 19. The immunogenic protein according to Embodiment 14 wherein the HPV6 E6 antigenic domain and the HPV6 E7 antigenic domain are separated by one or more post-translational cleavage sites, one or more translational skipping sites, or both.

Embodiment 20. The immunogenic protein according to Embodiment 15 wherein the HPV11 E6 antigenic domain and the HPV11 E7 antigenic domain are separated by one or more post-translational cleavage sites, one or more translational skipping sites, or both.

Embodiment 21. A vaccine comprising the nucleic acid molecule of any one of Embodiments 1 to 9 or the expression vector of any one of Embodiments 10 to 12 and a pharmaceutically acceptable excipient.

Embodiment 22. A pharmaceutical composition comprising the nucleic acid molecule of any one of Embodiments 1 to 9 or the expression vector of any one of Embodiments 10 to 12 and a pharmaceutically acceptable excipient.

Embodiment 23. The pharmaceutical composition according to Embodiment 22, comprising an adjuvant.

Embodiment 24. The pharmaceutical composition according to Embodiment 23 wherein the adjuvant comprises interleukin-12 (IL12).

Embodiment 25. The pharmaceutical composition according to Embodiment 24 wherein the IL12 is encoded by a nucleic acid molecule.

Embodiment 26. The pharmaceutical composition according to Embodiment 25, wherein the nucleic acid molecule encoding IL12 is an expression vector.

Embodiment 27. A vaccine comprising the immunogenic protein of any one of Embodiments 13 to 20.

Embodiment 28. A pharmaceutical composition comprising the immunogenic protein of any one of Embodiments 13 to 20 and a pharmaceutically acceptable excipient.

Embodiment 29. The pharmaceutical composition according to Embodiment 28, comprising an adjuvant.

Embodiment 30. The pharmaceutical composition according to Embodiment 29 wherein the adjuvant comprises interleukin-12 (IL12).

Embodiment 31. The pharmaceutical composition according to Embodiment 23 or 29, wherein the adjuvant comprises a nucleic acid molecule comprising a nucleotide sequence encoding the p35 subunit of IL-12, the p40 subunit of IL-12, or both.

Embodiment 32. The pharmaceutical composition according to Embodiment 31, wherein the nucleotide sequence encoding the p35 subunit of IL12 comprises a nucleotide sequence selected from the group consisting of:
 a nucleotide sequence that encodes SEQ ID NO: 6; or
 a nucleotide sequence that is at least 95% homologous to a nucleotide sequence that encodes SEQ ID NO: 6.

Embodiment 33. The pharmaceutical composition according to Embodiment 31 or 32, wherein the nucleotide sequence encoding the p40 subunit of IL12 comprises a nucleotide sequence selected from the group consisting of:
 a nucleotide sequence that encodes SEQ ID NO: 8; or
 a nucleotide sequence that is at least 95% homologous to a nucleotide sequence that encodes SEQ ID NO: 8.

Embodiment 34. The pharmaceutical composition according to Embodiment 31, 32, or 33, wherein the nucleotide sequence encoding IL12 comprises a nucleotide sequence selected from the group consisting of:
 the nucleotide sequence of SEQ ID NO: 4; or
 a nucleotide sequence that is at least 95% homologous to the nucleotide sequence of SEQ ID NO: 4.

Embodiment 35. The pharmaceutical composition according to any one of Embodiments 31 to 34 wherein the nucleic acid molecule comprising a nucleotide sequence encoding the p35 subunit of IL-12, the p40 subunit of IL-12, or both is an expression vector.

Embodiment 36. The pharmaceutical composition according to Embodiment 35 wherein the expression vector comprising the nucleic acid molecule encoding the p35 subunit of IL-12, the p40 subunit of IL-12, or both is the same expression vector or a different expression vector than the expression vector comprising the nucleic acid molecule encoding the HPV antigen.

Embodiment 37. The pharmaceutical composition according to any one of Embodiments 22 to 26 or 28 to 36 wherein the pharmaceutically acceptable excipient comprises a buffer, optionally saline-sodium citrate buffer, optionally a buffer comprising 150 mM sodium chloride and 15 mM sodium citrate, pH 7.

Embodiment 38. The pharmaceutical composition of Embodiment 37, wherein the composition comprises 6 mg of the vector encoding the HPV antigen per milliliter of saline-sodium citrate buffer and 0.25 mg of the vector encoding the p35 subunit of IL-12, the p40 subunit of IL-1, or both, per milliliter of buffer.

Embodiment 39. The pharmaceutical composition of Embodiment 38, wherein the composition comprises 6 mg of pGX3024 per milliliter of saline-sodium citrate buffer and 0.25 mg of pGX6010 per milliliter of buffer.

Embodiment 40. A method of inducing an immune response in a subject comprising administering to the subject an effective amount of the nucleic acid molecule according to any one of Embodiments 1 to 9, the expression vector according to any one of Embodiments 10 to 12, the immunogenic protein according to any one of Embodiments 13 to 20, the vaccine according to Embodiment 21 or Embodiment 27, or the pharmaceutical composition according to any one of Embodiments 22 to 26 or 28 to 39, to thereby induce the immune response.

Embodiment 41. A method of prophylactically or therapeutically immunizing a subject against HPV6 and/or HPV11 comprising administering to the subject an effective amount of the nucleic acid molecule according to any one of Embodiments 1 to 9, the expression vector according to any one of Embodiments 10 to 12, the immunogenic protein according to any one of Embodiments 13 to 20, the vaccine according to Embodiment 21 or Embodiment 27, or the pharmaceutical composition according to any one of Embodiments 22 to 26 or 28 to 39, to thereby induce an immune response against HPV6, HPV11, or both.

Embodiment 42. A method for treating or preventing recurrent respiratory papillomatosis (RRP) in a subject comprising administering to the subject an effective amount of the nucleic acid molecule according to any one of Embodiments 1 to 9, the expression vector according to any one of Embodiments 10 to 12, the immunogenic protein according to any one of Embodiments 13 to 20, the vaccine according to Embodiment 21 or Embodiment 27, or the pharmaceutical composition according to any one of Embodiments 22 to 26 or 28 to 39, to thereby treat or prevent RRP.

Embodiment 43. The method according to Embodiment 42 wherein the RRP is juvenile-onset RRP or adult-onset RRP.

Embodiment 44. The method according to any one of Embodiments 40 to 43, wherein the nucleic acid molecule comprises the nucleotide sequence of SEQ ID NO: 2, SEQ ID NO: 3, or SEQ ID NO: 12.

Embodiment 45. The method according to any one of Embodiments 40 to 44, further comprising administering an adjuvant to the subject.

Embodiment 46. The method according to Embodiment 45 wherein the adjuvant is interleukin-12 (IL12).

Embodiment 47. The method according to Embodiment 46 wherein the IL12 is encoded by a nucleic acid molecule.

Embodiment 48. The method according to Embodiment 45, wherein the adjuvant comprises a nucleic acid molecule comprising a nucleotide sequence encoding the p35 subunit of IL-12, the p40 subunit of IL-12, or both.

Embodiment 49. The method according to Embodiment 48, wherein the nucleotide sequence encoding the p35 subunit of IL-12 comprises a nucleotide sequence selected from the group consisting of:
 a nucleotide sequence that encodes SEQ ID NO: 6; or
 a nucleotide sequence that is at least 95% homologous to a nucleotide sequence that encodes SEQ ID NO: 6.

Embodiment 50. The method of Embodiment 48 or 49, wherein the nucleotide sequence encoding the p40 subunit of IL-12 comprises a nucleotide sequence selected from the group consisting of:
 a nucleotide sequence that encodes SEQ ID NO: 8; or
 a nucleotide sequence that is at least 95% homologous to a nucleotide sequence that encodes SEQ ID NO: 8.

Embodiment 51. The method according to Embodiment 47, wherein the nucleic acid molecule encoding IL12 comprises a nucleotide sequence selected from the group consisting of:
 the nucleotide sequence of SEQ ID NO: 4; or
 a nucleotide sequence that is at least 95% homologous to the nucleotide sequence of SEQ ID NO: 4.

Embodiment 52. The method according to Embodiment 47, wherein the nucleic acid molecule encoding the IL12 is an expression vector, optionally a plasmid.

Embodiment 53. The method according to Embodiment 52, wherein the plasmid is pGX6010.

Embodiment 54. The method according to any one of Embodiments 40 to 53, wherein the subject is a human.

Embodiment 55. The method according to any one of Embodiments 40 to 54, wherein the administering comprises intradermal or intramuscular injection.

Embodiment 56. The method according to Embodiment 55, wherein the administering further comprises electroporation.

Embodiment 57. Use of an effective amount of the nucleic acid molecule according to any one of Embodiments 1 to 9, the expression vector according to any one of Embodiments 10 to 12, or the immunogenic protein according to any one of Embodiments 13 to 20 in the manufacture of a prophylactic or medicament.

Embodiment 58. Use of an effective amount of the nucleic acid molecule according to any one of Embodiments 1 to 9, the expression vector according to any one of Embodiments 10 to 12, or the immunogenic protein according to any one of Embodiments 13 to 20 in the manufacture of a prophylactic or medicament to prevent or treat human papilloma virus (HPV) 6 or HPV11 infection.

Embodiment 59. Use of an effective amount of the nucleic acid molecule according to any one of Embodiments 1 to 9, the expression vector according to any one of Embodiments 10 to 12, the immunogenic protein according to any one of Embodiments 13 to 20, the vaccine according to Embodiment 21 or Embodiment 27, or the pharmaceutical composition according to any one of Embodiments 22 to 26 or 28 to 39 to prevent or treat human papilloma virus (HPV) 6 or HPV11 infection.

Embodiment 60. Use of an effective amount of the nucleic acid molecule according to any one of Embodiments 1 to 9, the expression vector according to any one of Embodiments 10 to 12, the immunogenic protein according to any one of Embodiments 13 to 20, the vaccine according to Embodiment 21 or Embodiment 27, or the pharmaceutical composition according to any one of Embodiments 22 to 26 or 28 to 39 to prevent or treat recurrent respiratory papillomatosis (RRP).

Embodiment 61. The use according to Embodiment 60 wherein the RRP is juvenile-onset RRP or adult-onset RRP.

Embodiment 62. The use according to any one of Embodiments 57 to 61, wherein the nucleic acid molecule comprises the nucleotide sequence of SEQ ID NO: 2, SEQ ID NO: 3, or SEQ ID NO: 12.

Embodiment 63. The use according to any one of Embodiments 57 to 62 in combination with an adjuvant.

Embodiment 64. The use according to Embodiment 63 wherein the adjuvant is interleukin-12 (IL12).

Embodiment 65. The use according to Embodiment 64 wherein the IL12 is encoded by a nucleic acid molecule.

Embodiment 66. The use according to Embodiment 65, wherein the adjuvant comprises a nucleic acid molecule comprising a nucleotide sequence encoding the p35 subunit of IL-12, the p40 subunit of IL-12, or both.

Embodiment 67. The use according to Embodiment 66, wherein the nucleotide sequence encoding the p35 subunit of IL-12 comprises a nucleotide sequence selected from the group consisting of:
a nucleotide sequence that encodes SEQ ID NO: 6; or
a nucleotide sequence that is at least 95% homologous to a nucleotide sequence that encodes SEQ ID NO: 6.

Embodiment 68. The use according to Embodiment 66 or 67, wherein the nucleotide sequence encoding the p40 subunit of IL-12 comprises a nucleotide sequence selected from the group consisting of:
a nucleotide sequence that encodes SEQ ID NO: 8; or
a nucleotide sequence that is at least 95% homologous to a nucleotide sequence that encodes SEQ ID NO: 8.

Embodiment 69. The use according to Embodiment 65, wherein the nucleic acid molecule encoding IL12 comprises a nucleotide sequence selected from the group consisting of:
the nucleotide sequence of SEQ ID NO: 4; or
a nucleotide sequence that is at least 95% homologous to the nucleotide sequence of SEQ ID NO: 4.

Embodiment 70. The use according to Embodiment 65, wherein the nucleic acid molecule encoding the IL12 is an expression vector, optionally a plasmid.

Embodiment 71. The use according to Embodiment 70, wherein the plasmid is pGX6010.

The present invention is further illustrated in the following Examples. It should be understood that these Examples, while indicating embodiments of the invention, is given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Each of the U.S. patents, U.S. applications, and references cited throughout this disclosure are hereby incorporated in their entirety by reference.

EXAMPLES

Figure 1B:
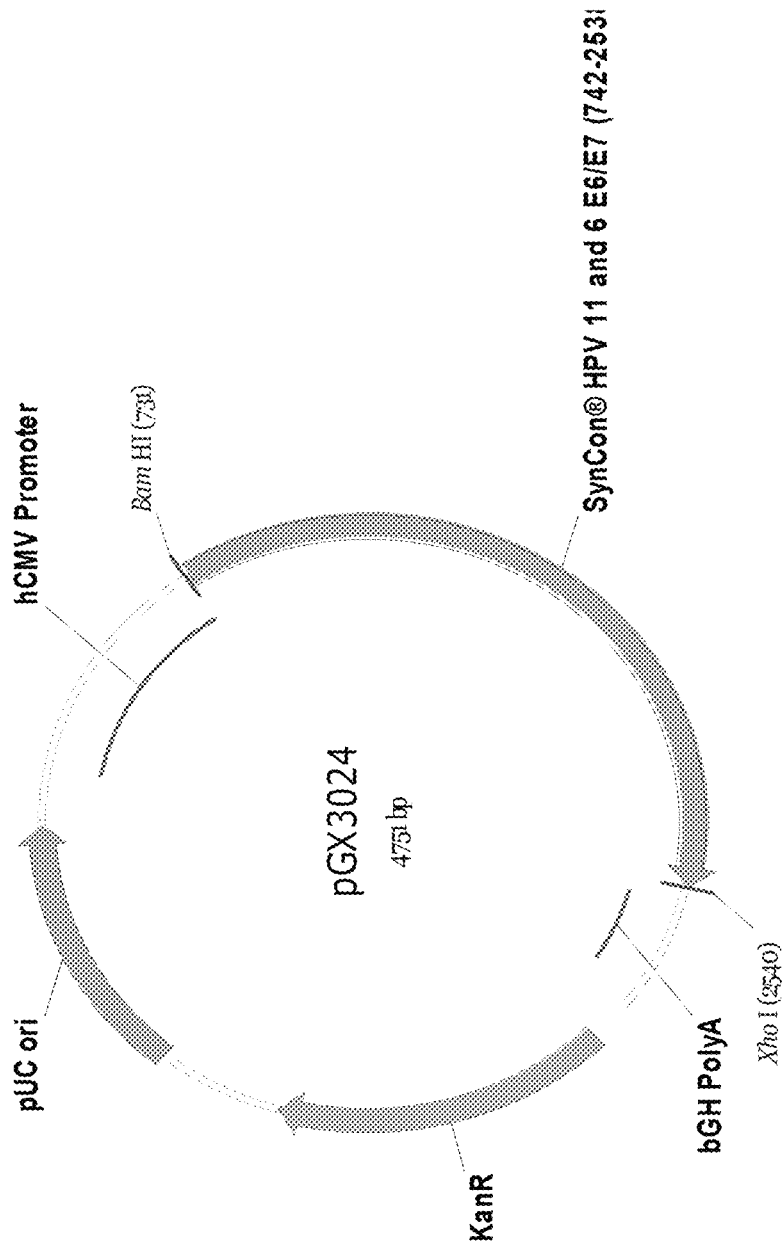
FIG. 1B provides a plasmid map of pGX3024.

Generation of HPV6 and HPV11 E6/E7 Consensus-Based Fusion Immunogen DNA Constructs HPV6 E6/E7 and HPV11 E6/E7 consensus sequences were generated using sequences obtained from GenBank. Two point mutations were introduced into the HPV6 E6 and HPV11 E6 proteins to inhibit the ability to bind and degrade p53. One point mutation was introduced into the HPV6 E7 and HPV11 E7 proteins to abolish binding of p130. Sequences were optimized using Inovio's proprietary gene optimization algorithm. FIG. 1A shows a schematic of antigens encoded in different HPV6 and/or HPV11 plasmids. Individual antigens are separated by a P2A cleavage site for translational skipping and a furin cleavage site for post-translational cleavage of the P2A sequence. DNA plasmid pGX3024 encodes consensus SynCon® E6 and E7 antigens of both HPV6 and HPV11. FIG. 1B provides a plasmid map of pGX3024.

In Vitro Transfection and Western Blot Analyses

Expression of pGX3024 in vitro. pGX3024 mediated HPV6 and HPV11 E6 and E7 antigen expression was confirmed by Western blot analysis following in vitro transfection of HEK-293T cells with pGX3024 plasmid. Cells transfected with plasmids encoding either HPV6 or HPV11 E6 and E7 antigens (pGX3021 and pGX3022, respectively) served as positive controls while cells transfected with empty plasmid backbone (pGX0001) served as negative control.

HEK-293T cells were plated at 80% confluence the day before transfections in 6-well tissue culture dishes. The following day, cells were transfected according to manufacturer recommendations with 3 μg of plasmid DNA using Lipofectamine 3000 transfection reagent (Thermo Scientific). Forty-eight hours post-transfection, cell lysates were harvested and protein concentration was determined by BCA assay (Quick Start™ Bradford Protein Assay, BioRad). Thirty micrograms (30 μg) of cell lysates were loaded onto a 12% Bis-Tris acrylamide gel (Thermo Scientific) and transferred to a PVDF membrane. Precision Plus Protein™ Dual Xtra Prestained Protein Standards (BioRad, cat #1610377) was loaded as a molecular weight reference. Following transfer, blots were washed in 1×PBS/0.05% Tween-20 and blocked for 1 h at room temperature in 1×PBS/0.05% Tween-20/5% Milk then probed overnight with diluted anti-HPV11 E7 (Genetex), at room temperature overnight. The next day, the blots were washed then incubated with anti-mouse IgG HRP (Bethyl Laboratories) 1:10,000 for 1 hour at room temperature then washed again. For detection, blots were incubated for 5 mins with ECL Prime Western blotting substrate (GE Lifesciences/Amersham cat #RPN2232/89168-782). Blots were imaged on the Protein Simple FluorChem® by chemiluminescence. After detection, blots were stripped by adding Restore reagent (Thermofisher, cat #21059) for 15 mins then washed and probed with anti-2A (EMD Millipore) or anti-β-actin (Santa Cruz Biotech) and developed as before.

As shown in FIG. 2, E6 and E7 proteins were detected in cells transfected with pGX3024 and control pGX3021 and pGX3022 plasmids, but not negative control pGX0001 plasmid. E7 protein expression was detected using a commercially available anti-HPV11 E7 antibody (FIG. 2, left panel). E7 proteins were detected in cells transfected with pGX3024, but not negative control pGX0001 plasmid. E7 antigen was detected in cells transfected with HPV6 antigen-only plasmid (pGX3021) as well HPV11 antigen-only plasmid (pGX3022), indicating the anti-HPV11 E7 antibody was cross-reactive against both HPV6 and HPV11 E7 antigens and suggesting the bands detected in pGX3024-transfected cells represent both HPV6 and HPV11 E7 protein expression.

After evaluating multiple commercially available reagents, an antibody that specifically recognized HPV6 or HPV11 E6 proteins was unable to be identified. However, using the anti-HPV11 E7 probe, two specific bands were detected at the predicted molecular weights of ~10.7 kDa and ~13 kDa for E7 and E7-furin/P2A, respectively, indicating partial furin cleavage of the P2A sequence in this in vitro system (FIG. 2, left panel). Both E6 and E7 antigen expression were therefore able to be detected using an anti-2A antibody probe against partially cleaved protein products (FIG. 2, middle panel). A band representing ~20 kDa E6-furin/P2A was detected in pGX3024, but not control pGX0001-transfected cells after probing with anti-2A antibody. Also, a ~15 kDa E7-furin/P2A band was detected in pGX3024, but not control pGX0001, transfected cells, coinciding with what was detected using the anti-HPV11 E7 probe.

Mouse IFN-γ ELISpot pGX3024 was evaluated for immunogenicity in two mouse models (FIGS. 3 through 6). DNA vaccine pGX3024-induced cellular and humoral immune responses were characterized in the C57BL/6 mouse model in two independent studies. Female C57BL/6 mice (n of 5 or 10 per group in Study 1 or Study 2, respectively) received two immunizations spaced two weeks apart by intramuscular electroporation (IM-EP) delivery of 20 μg pGX3024 or control DNA vaccines. T cell responses were measured one week post second immunization by IFNγ ELISpot after splenocyte stimulation with HPV6/HPV11 E6 or E7 peptides. Following euthanization, mouse spleens were isolated and placed in a tube containing 5 ml of R10 media (RPMI 1640 supplemented with 10% fetal bovine serum, 1% penicillin-streptomycin and 0.001% 2-mercaptoethanol). Splenocytes were isolated by mechanical disruption of the spleen using the GentleMACS Dissociator (Miltenyi Biotech) then filtered using a 40 μm cell strainer (BD Falcon). After centrifugation, resuspended cell pellets were treated with ACK lysis buffer (Lonza) for 5 mins to lyse red blood cells. The splenocytes were washed in PBS, centrifuged, resuspended in R10 media and counted using the Vi-cell (Beckman Coulter). Mouse IFN-γ ELISpot kits were purchased from MabTech (MabTech #3321-4APW-10) to evaluate antigen-specific responses. The precoated 96-well plates were washed in PBS according to the manufacturer's protocol and blocked for 2 hrs at room temperature with R10 media. Isolated splenocytes were resuspended in R10 media and plated in triplicate at $2 \times 10^5$ cells per well. Overlapping 15-mer peptides for HPV6 E6 and E7 proteins as well as HPV11 E6 and E7 proteins were synthesized. These peptides were resuspended in DMSO (Sigma) and pooled at a concentration of ~2 μg/ml per peptide into two peptide pools per each antigen (HPV6 E6, HPV6 E7, HPV11 E6 and HPV11 E7) for cell stimulation. As a positive control, Concavalin A (Sigma) was used at 5 μg/ml and complete media with DMSO was used as a negative control. The plates were incubated for a minimum of 18 hours at 37° C. 5% CO2. For development, plates were first washed in PBS then incubated with a biotinylated anti-mouse IFN-γ detection antibody (R4-6A2-biotin) for 2 hours at room temperature. After washing, plates were then incubated with streptavidin-ALP (MabTech #3321-4APW-10) for 1 hour at room temperature. Spots were detected using a filtered substrate solution (BCIP/NBT-plus) according to manufacturer's instruction (MabTech). Once the plates were dried, the spots were counted using an automated ELISpot reader (Cellular Technology). The average spot forming unit (SFU) was adjusted to $1 \times 10^6$ splenocytes and antigen-specific responses are reported as the number of IFN-γ SFU per $1 \times 10^6$ splenocytes greater than DMSO control.

Figure 3:
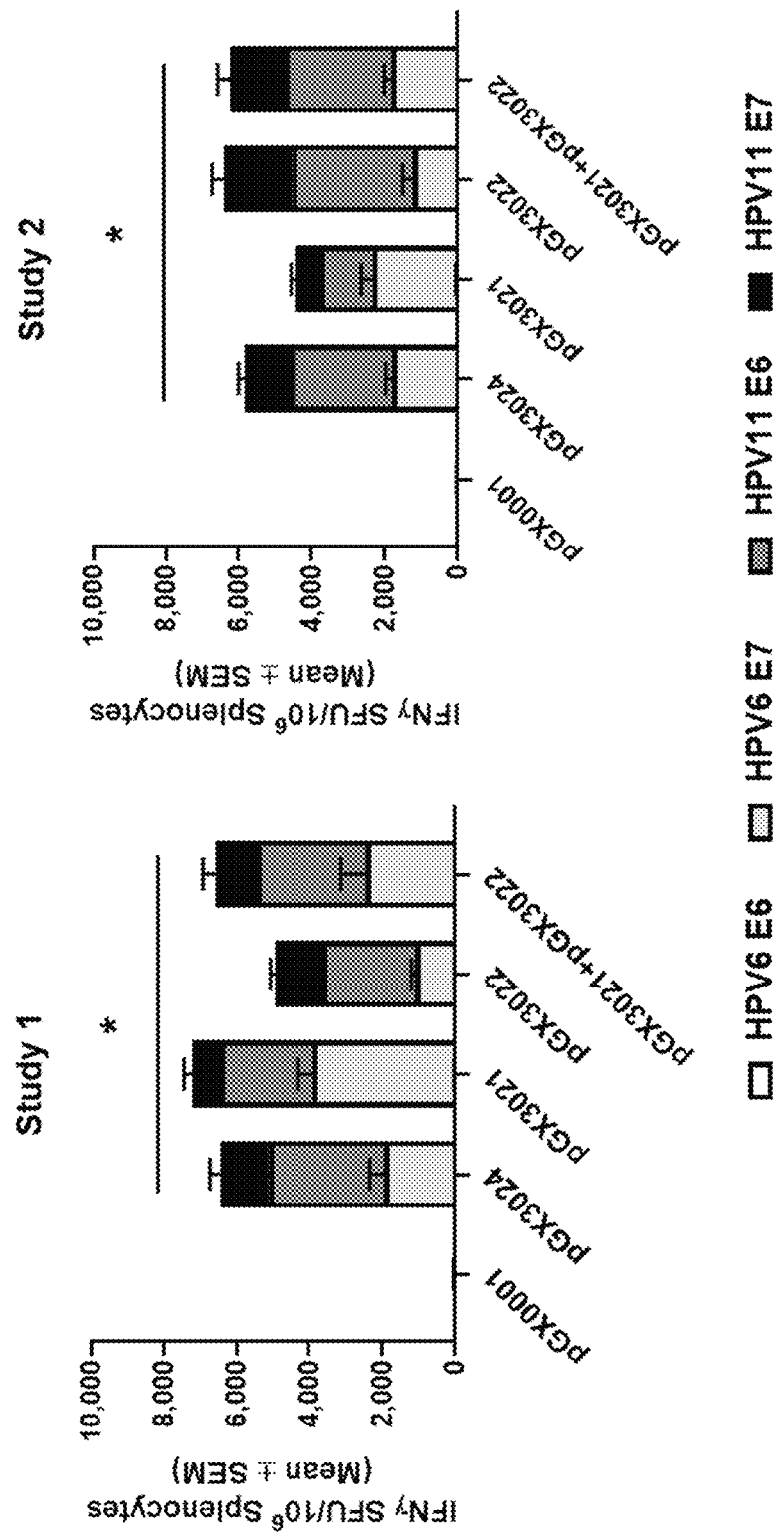
FIG. 3 illustrates HPV6- and HPV11-specific cellular responses following pGX3024 immunization of C57BL/6 mice. C57BL/6 mouse splenocytes were collected at one week post-immunization with either pGX3024, control plasmids encoding HPV6 (pGX3021) or HPV11 (pGX3022) antigens, or negative control plasmid (pGX0001). Specific cellular responses to HPV6 and HPV11 E6 and E7 peptides were measured by IFNγ ELISpot assay. Asterisk indicates significant difference in total cellular response as compared to pGX0001 control by one-way ANOVA, Dunnett's post-test.

HPV6 and HPV11 specific T cell responses were detected in mice following immunization with pGX3024, but not negative control pGX0001, plasmid (FIG. 3). There were no significant differences in T cell responses in mice immunized with pGX3024 as compared to mice immunized with pGX3021 and/or pGX3022 as determined by one-way ANOVA, Tukey's post-test (FIG. 3). Immunization with pGX3024 induced T cell responses against HPV6 E7, HPV11 E6, and HPV11 E7 antigens, but not HPV6 E6 antigen in this model. Inbred C57BL/6 mice have a single MHC haplotype (H2b) which may explain the lack of HPV6 E6 cellular responses in this model. T cell responses were highly reproducible between the two independent studies.

Antibodies against HPV6 and HPV11 E7 antigens were measured by binding IgG ELISA in sera samples collected before immunization (Week 0) and after first (Week 2) and second (Week 3) immunization with either pGX3024 or negative control plasmid (pGX0001).

IgG Antigen Binding ELISA 96-well high binding Nunc™ plates (Thermo Scientific) were coated with 0.5 μg/ml of each protein (HPV6 E7 and HPV11 E7—Tulip BioLabs) in 1×DPBS (Thermo Scientific) overnight at 4° C. The next day, plates were washed with 1×PBS+0.05% Tween-20 and blocked with 3% BSA in PBS+Tween-20 for 2 hours at 37° C. Plates were then washed as before and serially diluted sera samples were added and the plates were incubated for 2 hours at 37° C. Plates were washed and incubated with a 1:10,000 dilution of anti-mouse or rabbit IgG HRP secondary antibody (Bethyl Laboratories, Inc) for 1 hour at room temperature. The plates were washed and 100 µl/well of SureBlue TMP Substrate (KPL 5120-0077) was added to the plates. The reaction was stopped upon the addition of 100 ul/well of TMB Stop Solution (KPL 5150-0021) after a 6-minute incubation and the plates were read on a Biotek Synergy plate reader at the 450 nm wavelength.

Figure 4:
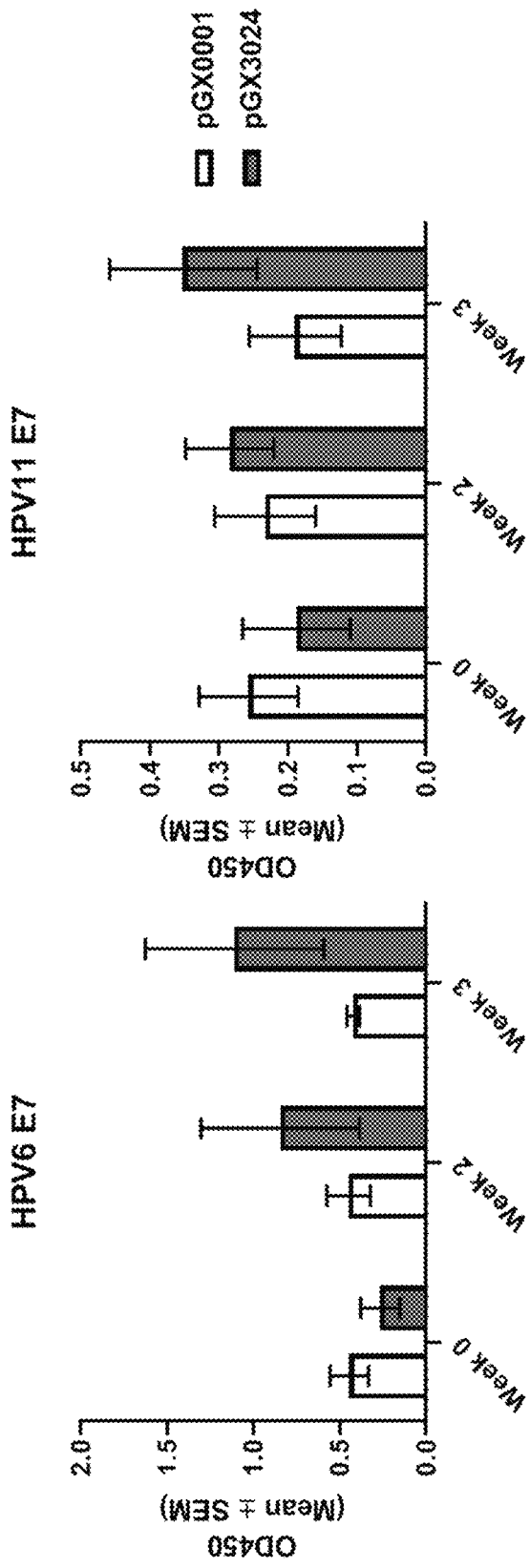
FIG. 4 shows HPV6 and HPV11 humoral responses following pGX3024 immunization of C57BL/6 mice. C57BL/6 mouse serum samples were collected at before immunization (Week 0) and after first (Week 2) and second (Week 3) immunization with either pGX3024 or negative control plasmid (pGX0001). Specific IgG binding antibodies against HPV6 E7 (left panel) or HPV11 E7 (right panel) antigens were measured by ELISA.
Figure 5:
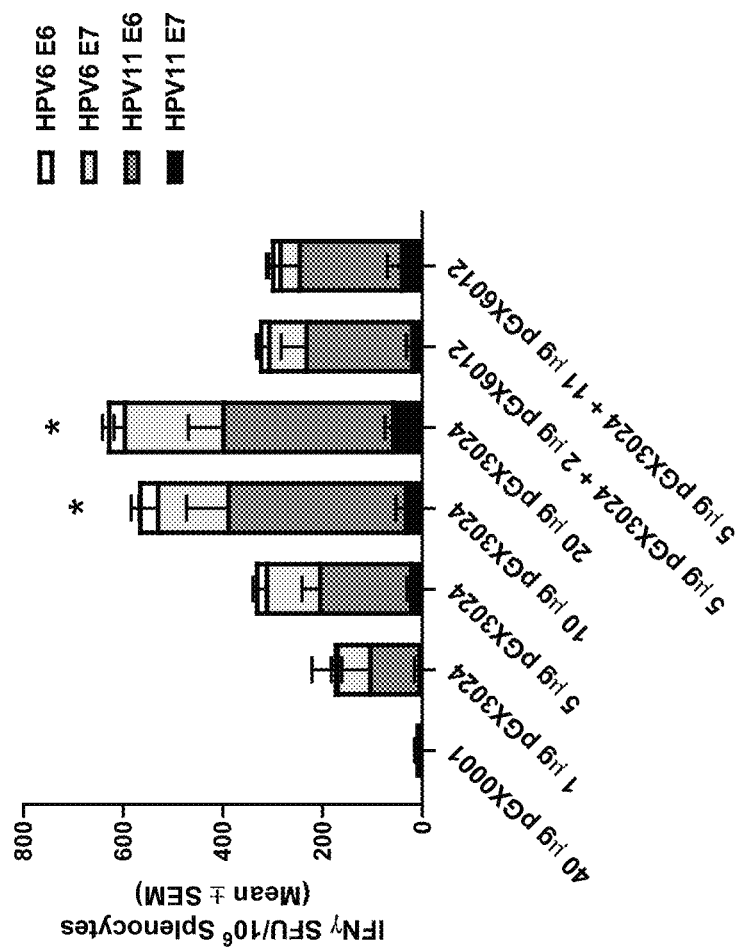
FIG. 5 illustrates HPV6- and HPV11-specific cellular responses following pGX3024 immunization of BALB/c mice. BALB/c mouse splenocytes were collected at one week post-immunization with the indicated dose of either pGX3024 alone or in combination with the indicated dose of plasmid murine IL-12 (pGX6012), or negative control plasmid (pGX0001). Specific cellular responses to HPV6 and HPV11 E6 and E7 peptides were measured by IFNγ ELISpot assay. Asterisk indicates significant difference in total cellular response as compared to pGX0001 control by one-way ANOVA Dunnett's post-test.

HPV6 E7 binding antibodies were detected in pGX3024, but not pGX0001, immunized mice after first and second immunization (FIG. 4, left panel). In general, HPV11 E7 binding antibodies were reduced compared to HPV6 E7 binding antibodies in immunized mice; however, HPV11 E7 binding antibodies were greater after two immunizations (week 3) in mice immunized with pGX3024 as compared to pGX0001 (FIG. 4, right panel).

pGX3024 immunogenicity in BALB/c mice. As previously mentioned, C57BL/6 mice have a single MHC haplotype (H2b) which may explain the lack of HPV6 E6 cellular responses in this model. pGX3024 vaccine-induced cellular responses were thus investigated in the BALB/c mouse model with a different MHC haplotype (H2d). The impact of pGX3024 dose and combination with a plasmid encoding murine IL-12 adjuvant (pGX6012) was also investigated. Female BALB/c mice (n of 6 per group) received two immunizations spaced two weeks apart by intramuscular electroporation (IM-EP) delivery of 1 µg, 5 µg, 10 µg, or 20 µg pGX3024 DNA vaccine alone, or 5 µg pGX3024 adjuvanted with either 2 µg or 11 µg pGX6012 murine IL-12 plasmid. Mice immunized with 40 µg empty pGX0001 plasmid served as negative controls. T cell responses were measured one week post second immunization by IFNγ ELISpot after splenocyte stimulation with HPV6/HPV11 E6 or E7 peptides as shown in FIG. 5. HPV6 and HPV11 specific T cell responses were detected in mice following immunization with all dose levels of pGX3024, but not pGX0001, plasmid in a dose-related manner. Total HPV6 and HPV11 cellular responses increased with increasing pGX3024 dose. Unlike the C57BL/6 model, pGX3024 immunized BALB/c mice had T cell responses against HPV6 E6 antigen as well as HPV6 E7, HPV11 E6 and HPV11 E7 antigens. There were no significant differences in T cell responses among mice immunized with 5 µg pGX3024 with or without either dose level of pGX6012 as determined by one-way ANOVA, Tukey's post-test.

Figure 6:
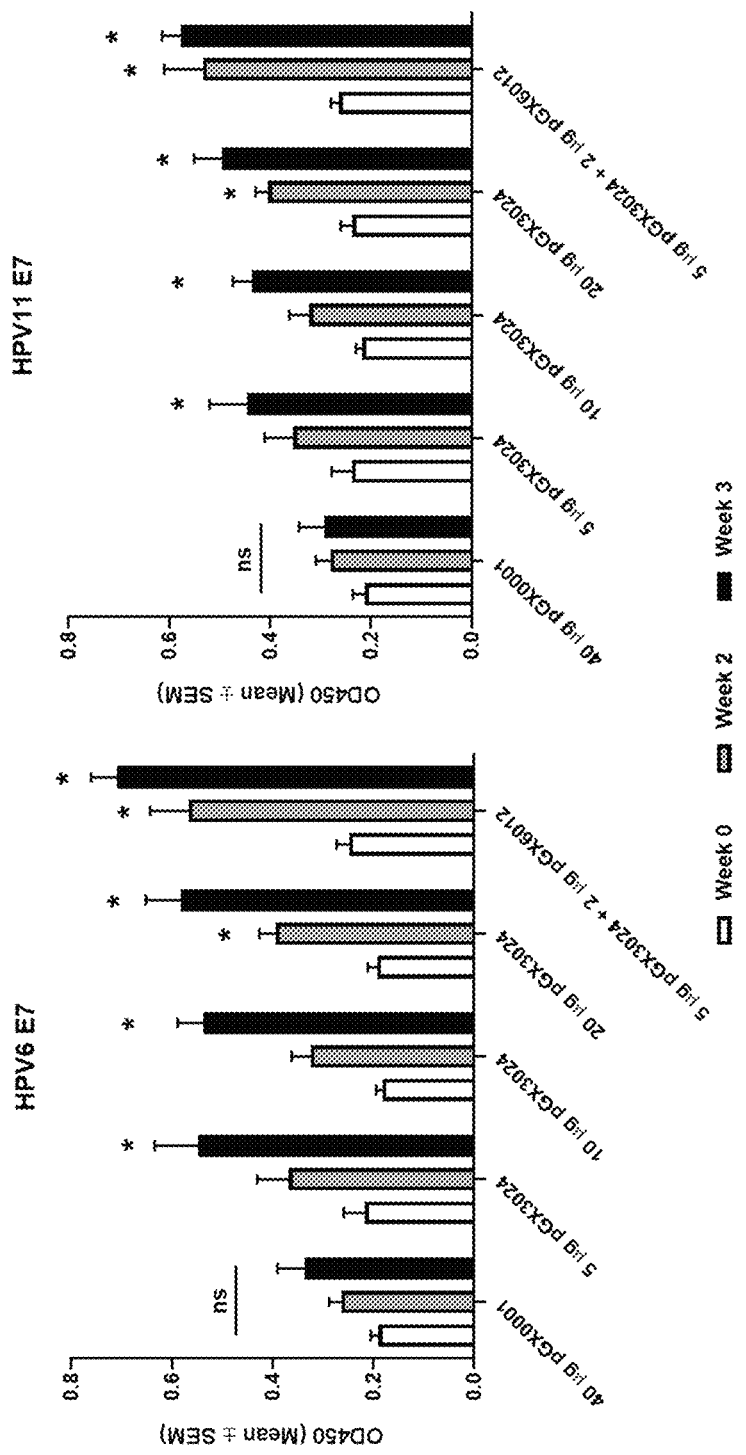
FIG. 6 illustrates HPV6 and HPV11 humoral responses following pGX3024 immunization of BALB/c mice. BALB/c mouse serum samples were collected before immunization (Week 0) and after first (Week 2) and second (Week 3) immunization with the indicated dose of either pGX3024 alone or in combination with the indicated dose of plasmid murine IL-12 (pGX6012), or negative control plasmid (pGX0001). Specific IgG binding antibodies against HPV6 E7 (left panel) or HPV11 E7 (right panel) antigens were measured by ELISA. Asterisk indicates significant and "ns" indicates no significant difference as compared to Week 0 by two-way ANOVA.

Antibodies against HPV6 and HPV11 E7 antigens were measured by binding IgG ELISA in sera samples collected before immunization (Week 0) and after first (Week 2) and second (Week 3) immunization with either 5 µg, 10 µg, or 20 µg pGX3024 DNA vaccine alone, or 5 µg pGX3024 adjuvanted with 2 µg murine IL-12 plasmid (pGX6012). Sera from mice immunized with 40 µg empty pGX0001 plasmid served as negative controls. HPV6 E7 and HPV11 E7 binding antibodies were significantly increased at Week 3 compared to Week 0 in pGX3024 immunized BALB/c mice regardless of dose or presence of IL-12 plasmid, but not in pGX0001 mice (FIG. 6). Antibody levels were also significantly increased after single immunization (Week 2) with 20 µg pGX3024, or 5 µg pGX3024 adjuvanted with 2 µg murine IL-12 plasmid. There was a trend of increased binding antibodies against both antigens with the addition of murine IL-12 to 5 µg pGX3024, particularly at the Week 2 timepoint.

Rabbit Immunogenicity Study

INO-3107 (pGX3024 with pGX6010) was evaluated for immunogenicity and safety in a rabbit model.

New Zealand White (NZW) rabbits (n of 5 per group) received four immunizations spaced three weeks apart of INO-3107 (6 mg pGX3024 and 0.25 mg pGX6010 co-formulated in 1 mL 1×SSC), or 1 mL 1×SSC (negative control) by intramuscular (IM) injection into the quadriceps followed by electroporation (EP) using the CELLECTRA® 2000 Electroporation Device. Cellular and humoral immune responses were evaluated by IFNγ ELISpot and IgG binding ELISA, respectively, before immunization (Week 0) and two weeks after each immunization (Weeks 2, 5, 8, and 11). Physiological parameters including body weights, hematology, serum chemistries, and general appearance were monitored throughout the study as indicators of vaccine safety and animal health.

Rabbit cellular responses were evaluated by IFNγ ELISpot assay following stimulation of PBMCs with HPV6/HPV11 E6 and E7 peptides. SepMate-15 ml tubes were filled with 3.5 ml of Ficoll-Paque gradient and allowed to equilibrate at room temperature. Whole blood was collected into K2EDTA tubes, followed by inversion several times to mix. The blood was diluted with Hank's Balanced Salts Solution (HBSS) and slowly layered on top of the Ficoll-Paque gradient in the SepMate tubes. The tubes were spun and the buffy coats were collected and placed into a fresh 15 ml tube. The cells were washed by diluting with R10 media (RPMI 1640 supplemented with 10% fetal bovine serum, 1% penicillin-streptomycin and 0.001% 2-mercaptoethanol). The cell pellet was resuspended in ACK lysis buffer (Lonza) to lyse red blood cells and incubated at room temperature for 4 mins. The PBMCs were washed, spun and resuspended in R10 media and counted using the Vi-cell (Beckman Coulter). Rabbit IFN-γ ELISpot kits (MabTech (MabTech #3110-4HPW-10) were used to evaluate antigen specific responses. Plates were prepared following the manufacturer's protocol and rabbit PBMCs were plated in triplicate at $2 \times 10^5$ cells per well. Overlapping 15-mer peptides for the E6 and E7 proteins of HPV6 and HPV11 were used for cell stimulation. Phorbol 12-myristate 13-acetate and ionomycin (PMA/I) (Sigma) and media containing DMSO served as a positive and negative control, respectively. The plates were incubated for a minimum of 18 hours at 37° C. 5% $CO_2$. The following day, plates were developed according to the manufacturer's protocol and once the plates were dried, the spots were counted using an automated ELISpot reader (Cellular Technology). The average spot forming unit (SFU) was adjusted to $1 \times 10^6$ splenocytes and antigen-specific responses are reported as the number of IFN-γ SFU per $1 \times 10^6$ splenocytes greater than DMSO control.

Figure 7:
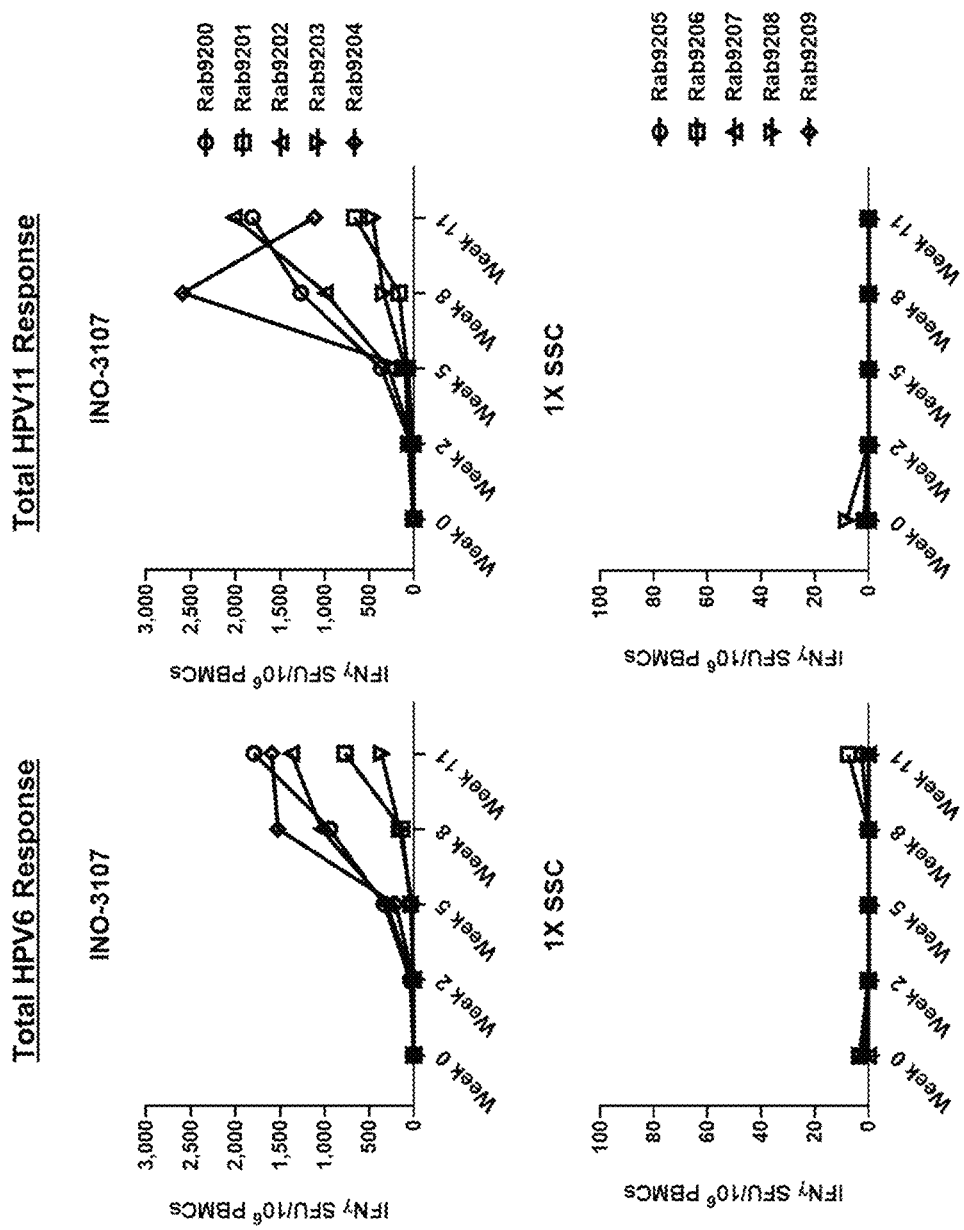
FIG. 7 illustrates the timecourse of HPV6- and HPV11-specific cellular responses following INO-3107 immunization of NZW rabbits. NZW rabbit peripheral blood mononuclear cells (PBMCs) were collected at the indicated timepoints post-immunization with either INO-3107 or 1× saline-sodium citrate buffer (SSC). Specific cellular responses to HPV6 E6 and E7 peptides and HPV11 E6 and E7 peptides were measured by IFNγ ELISpot assay. Data is depicted as the sum of HPV6 E6 and E7 (left panel) or HPV11 E6 and E7 (right panel) responses for individual animals.
Figure 8:
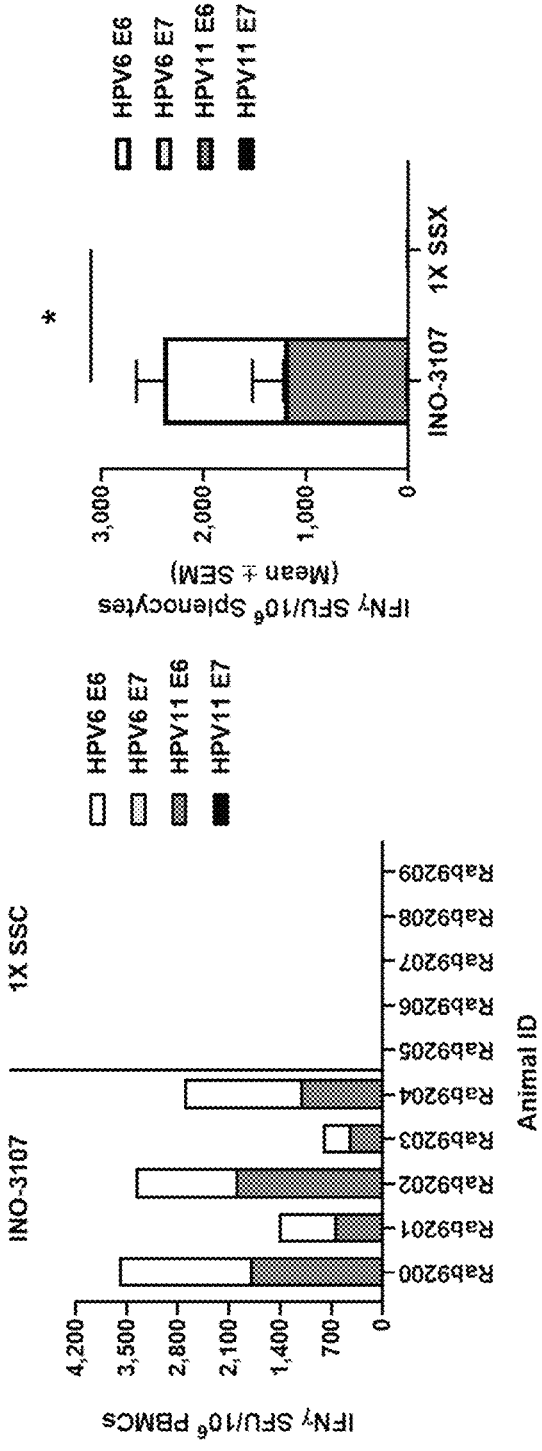
FIG. 8 illustrates HPV6- and HPV11-specific cellular responses following INO-3107 immunization of NZW rabbits. Week 11 (two weeks post fourth immunization), T cell responses against HPV6 E6, HPV6 E7, HPV11 E6, or HPV11 E7 antigens for NZW rabbits at Week 11 (two weeks post fourth immunization) with either INO-3107 or 1×SSC as described in FIG. 7. Data is depicted for individual rabbits (left panel) or the mean±SEM for each treatment group (right panel). Asterisk indicates significant difference ($p<0.05$) as determined by Mann-Whitney U-test.

HPV6 and HPV11 specific T cell responses above baseline were detected in all rabbits following immunization with INO-3107, but not in rabbits treated with 1×SSC. HPV6 and HPV11 T cell responses were boostable as they increased following each successive immunization with INO-3107 (FIG. 7). Immunization with INO-3107 induced T cell responses against HPV6 and HPV11 E6 antigens, but not HPV6 or HPV11 E7 antigens in this model (FIG. 8).

Figure 9:
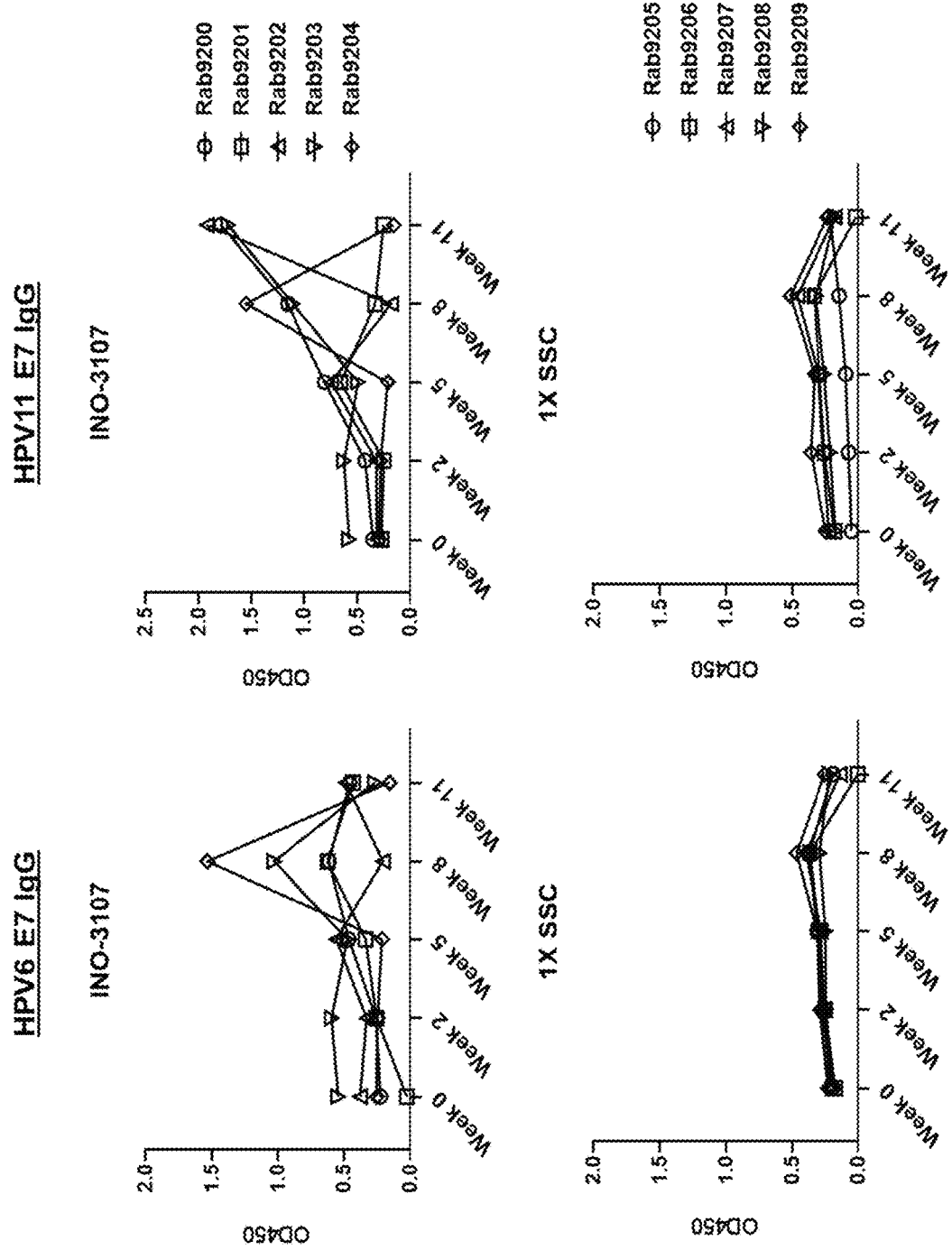
FIG. 9 shows the timecourse of HPV6 and HPV11 humoral responses following INO-3107 immunization of NZW rabbits. NZW rabbit serum samples were collected at the indicated timepoints post-immunization with either INO-3107 or 1×SSC. Specific humoral responses to HPV6 E7 (left panel) and HPV11 E7 (right panel) antigens were measured by IgG binding ELISA. Data are depicted for individual animals.

Humoral responses against HPV6 and HPV11 E7 antigens were measured by binding IgG ELISA in sera samples collected before and two weeks after each immunization. Timecourse of antibody levels are shown in FIG. 9. HPV6 or HPV11 E7 binding antibodies were detected in 4 of 5 rabbits immunized with INO-3107, but not in rabbits dosed with 1×SSC. In general, HPV6 E7 binding antibodies were reduced compared to HPV11 E7 binding antibodies in immunized rabbits. ELISpot and ELISA data taken together confirm immunogenicity of all antigens encoded by INO-3107 in the rabbit model.

Figure 10:
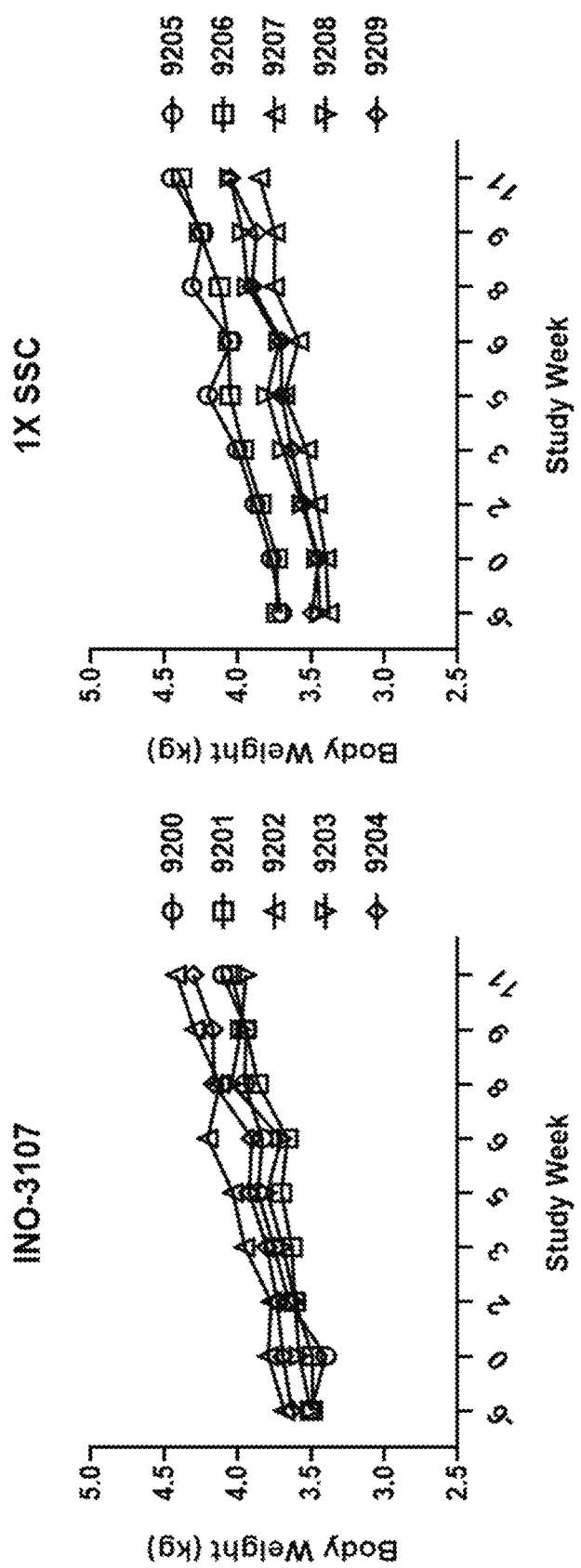
FIG. 10 shows timecourse of body weight measurements for NZW rabbits administered INO-3107 (left panel) or 1×SSC (right panel).

In addition to INO-3107-mediated immune responses, physiological parameters including body weights, hematology, serum chemistries, and general appearance were monitored throughout the study as indicators of vaccine safety and animal health. No significant differences in body weights or body weight changes over time were observed in rabbits administered INO-3107 (FIG. 10). Also, no findings were observed during monitoring of general appearance (nose, eyes, fur, movement) for either treatment groups during the study. Samples were collected for hematology and serum clinical chemistry analyses before and at Week 5, Week 8, and Week 11 after immunization and results were submitted for independent review by a clinical veterinary pathologist (IDEXX BioAnalytics). Compared to baseline values, administration of INO-3107 resulted in a mild increase in lymphocyte counts at Week 5 (but not Week 8 or Week 11) in NZW rabbits. There was no other hematologic or serum clinical chemistry finding from the administration of INO-3107 indicative of a biologically relevant effect.

Evaluation of Intradermal (ID) Delivery in Rabbit

Figure 13:
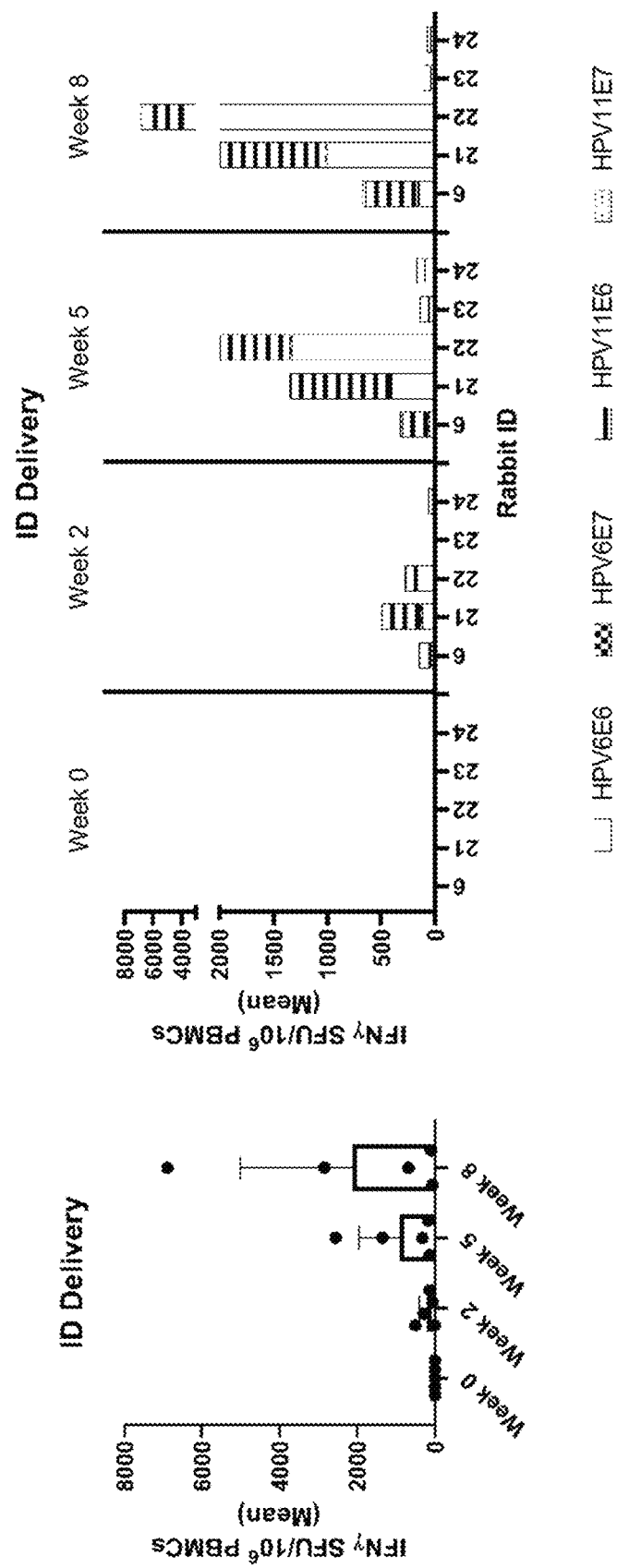
FIG. 13 shows immune responses induced following intradermal delivery of INO-3107 to NZW rabbits. Cellular immune responses were evaluated by IFNγ ELISpot before immunization (Week 0) and two weeks after each immunization (Weeks 2, 5 and 8). The combined immune response to both antigens, HPV6 and HPV11, increased following each immunization, with the T cell responses being more HPV6 E6- and HPV11 E6-specific.

An intradermal (ID) injection study was performed in NZW rabbits to assess cellular immune responses. NZW rabbits (n of 5) were immunized three times at three-week intervals with INO-3107 formulated at 1 mg pGX3024 in 0.1 mL 1×SSC, by ID delivery. Rabbit IFNγ ELISpots, previously described, were performed prior to the first vaccination and at Weeks 2, 5 and 8. The combined immune response to both antigens, HPV6 and HPV11, increased following each immunization, with the T cell responses being more HPV6 E6 and HPV11 E6 specific (FIG. 13).

Evaluation of Intradermal (ID) Delivery in Guinea Pig Model

Hartley guinea pigs (n of 5) received three immunizations spaced two weeks apart of pGX3024 (0.1 mg formulated in final 0.1 mL 1×SSC), intradermal (ID) injection followed by electroporation (EP) using the CELLECTRA® 2000 Electroporation Device. Naïve guinea pigs served as a negative control (n of 2). Cellular and humoral immune responses were evaluated by IFNγ ELISpot and IgG binding ELISA, respectively, before immunization (Week 0) and two weeks after each immunization (Weeks 2, 4, and 6).

Animal husbandry, immunizations and sample collections were performed at Acculab Life Sciences (San Diego, Calif.) under an IACUC approved protocol in compliance with the Animal Welfare Act, PHS Policy, AAALACi guidelines, USDA, and other Federal statutes and regulations relating to animals and experiments involving animals. All sample analyses were conducted at Inovio (San Diego, Calif.). pGX3024 was formulated in 1×SSC for final 0.1 mg in 0.1 mL dosing solution and stored at 2-8° C. until use. Female Hartley guinea pigs age 8 weeks were randomized into 2 groups of 5 or 2 animals in each according to Table 1. Each treatment was delivered by Mantoux intradermal (ID) injection of a 100 μL dosing solution into the skin followed by electroporation using the CELLECTRA 2000® Adaptive Constant Current Electroporation Device with a 3P array (Inovio Pharmaceuticals) according to the manufacturer's protocol.

TABLE 1

Study Design

| Group Number (n) | Plasmid | # Injection Sites (s)/ Location/ Tx | EP Device & Inj Method | Injection Volume (μl) | DNA dose/ plasmid (μg) |
|---|---|---|---|---|---|
| 1 (5) | pGX3024 | 1/ID | CELLECTRA 3P | 100 | 100 |
| 2 (2) | Naïve | — | — | — | — |

Group 1 animals received a total of three immunizations spaced two weeks apart. Sera samples were collected from all animals for humoral immunogenicity assessments at Week 0, Week 2, Week 4 and Week 6. Whole blood samples were collected from all animals for cellular immunogenicity assessments at Week 2, Week 4, and Week 6.

Guinea pig IFN-γ ELISpot. Guinea pig IFN-γ ELISpot was performed according to methods described in Schultheis, et al., *J Vis Exp.* 2019; (143):10.3791/58595. Published 2019 Jan. 20. doi:10.3791/58595. Peripheral blood was drawn from the jugular vein of each anaesthetized animal and transferred immediately into EDTA blood collection tubes. Blood was diluted 1:1 with phosphate-buffered saline. Diluted blood was layered over Ficoll-Paque Plus (GE Healthcare Life Sciences) in SepMate™ tubes (Stemcell) and centrifuged (1200 g, 10 min, 24° C.). PBMCs were resuspended at $1 \times 10^6$ cells/ml in R10 medium and plated at 100 μl/well on 96-well Millipore IP plates (Millipore) previously coated with 5 μg/ml primary anti-IFN-γ antibody V-E4 (provided by Dr. Schafer, Robert Koch Institute, Berlin, Germany) blocked with R10 media. 100 μl of HPV6 E6, HPV6 E7, HPV11 E6, or HPV11 E7 peptide pools, or phorbol 12-myristate 13-acetate (PMA)/Ionomycin stimulants were added to the cells. Samples were assayed in triplicates. After incubation in humidified 5% $CO_2$ at 37° C. for 18 hours, cells were removed by washing and 100 μl per well of 2 μg/ml biotinylated secondary anti-IFN-γ antibody N-G3 diluted in blocking buffer was added. Following a 2 hour incubation and washing, alkaline phosphatase-conjugated streptavidin (MabTech) was added at 100 μl per well for 1 hour at room temperature. Following washes, wells were incubated for 6-12 min at room temperature with 100 μl per well of nitro-blue tetrazolium/5-bromo-4-chloro-3'-indolyphosphate (BCIP/NBT) detection reagent substrate (MabTech). Interferon-gamma positive spots were imaged, analyzed and counted using a CTL-Immunospot® S6 ELISPOT Plate Reader and CTL-Immunospot® software. Antigen-specific responses were determined by subtracting the number of spots in DMSO-treated from peptide-treated wells.

Figure 11:
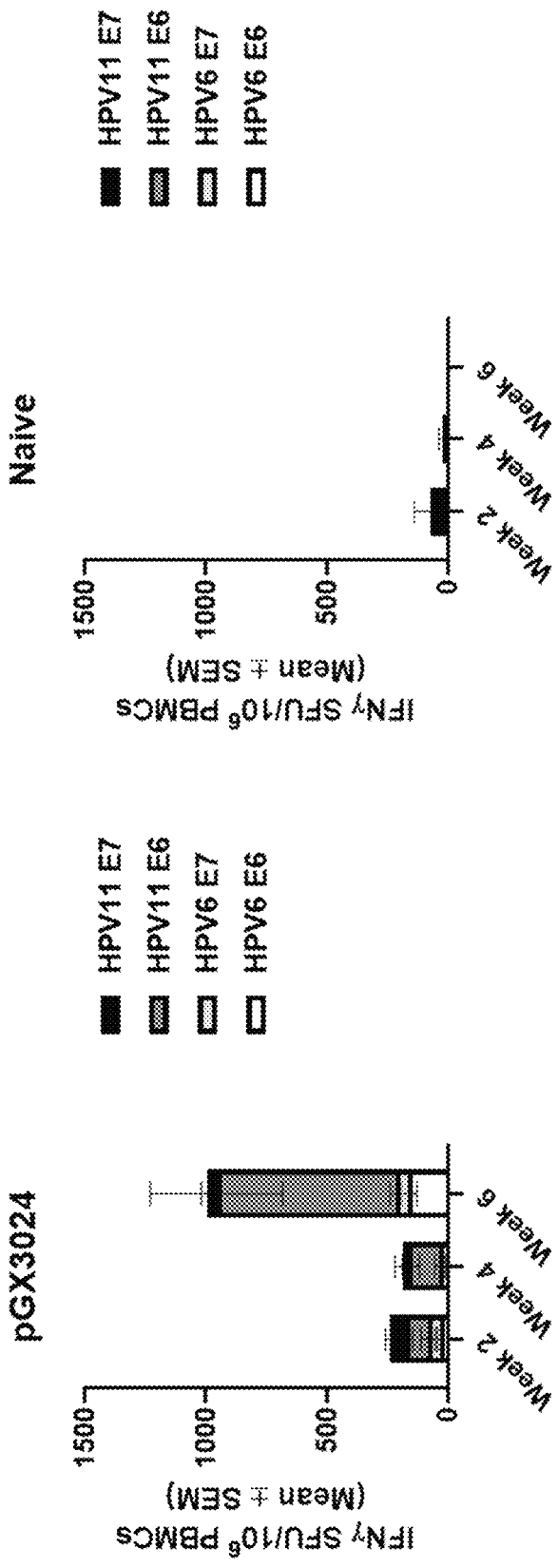
FIG. 11 illustrates the timecourse of HPV6- and HPV11-specific cellular responses following pGX3024 immunization of Hartley guinea pigs. Guinea pigs (n of 5) were immunized on Weeks 0, 2, and 4 with 100 ug pGX3024 administered by CELLECTRA intradermal electroporation. Naïve guinea pigs (n of 2) served as negative controls. Guinea pig peripheral blood mononuclear cells (PBMCs) were collected at the indicated timepoints post-immunization with pGX3024, or from naïve guinea pigs. Specific cellular responses to HPV6 E6 and E7 peptides and HPV11 E6 and E7 peptides were measured by IFNγ ELISpot assay. Data is depicted as the mean±SEM for each treatment group. of HPV6 E6 and E7.

Results are shown for individual animal spot-forming units (SFU)/$10^6$ PBMCs obtained for triplicate wells. HPV6 and HPV11 specific T cell responses above baseline were detected in guinea pigs following immunization with pGX3024, but not in naïve guinea pigs (FIG. 11). Immunization with pGX3024 induced T cell responses against HPV6 and HPV11 E6 and E7 antigens in this model (FIG. 11).

Antigen Binding ELISA. 96-well high binding Nunc™ plates (Thermo Scientific) were coated with 1 ng/ml of recombinant HPV6 E7 or HPV11 E7 proteins in 1× Dulbecco's phosphate-buffered saline (DPBS) (Thermo Scientific) overnight at 4° C. The next day, plates were washed with 1×PBS+0.05% Tween®-20 and blocked with 3% BSA in PBS+0.05% Tween®-20 for 2 hours at RT. Plates were then washed as before and serially diluted sera samples were added and the plates were incubated for 2 hours at room temperature. Plates were washed and incubated with a 1:10,000 dilution of anti-guinea pig IgG horseradish peroxidase (HRP) secondary antibody (Sigma) for 1 hour at room temperature. The plates were washed and 100 µl/well of SureBlue™ TMB Substrate (KPL 5120-0077) was added to the plates. The reaction was stopped upon the addition of 100 ul/well of TMB Stop Solution (KPL 5150-0021) after a 6 minute incubation and the plates were read on a Biotek Synergy plate reader at the 450 nm wavelength.

Figure 12:
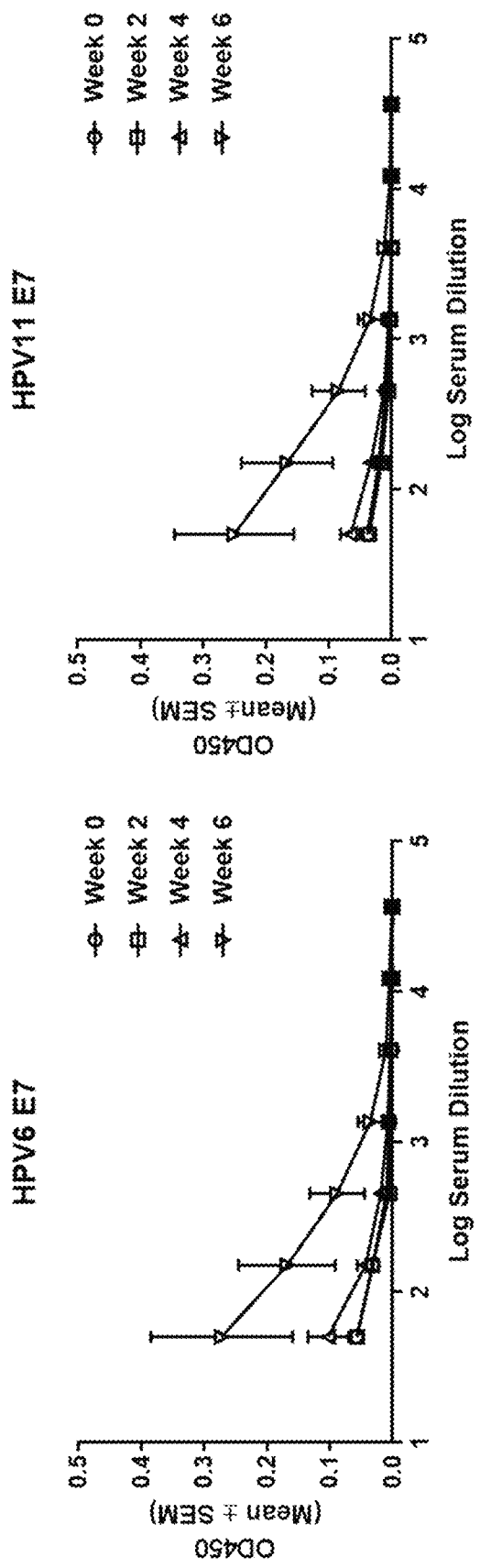
FIG. 12 shows the timecourse of HPV6- and HPV11-specific humoral responses following pGX3024 immunization of Hartley guinea pigs. Hartley guinea pigs (n of 5) were immunized on Weeks 0, 2, and 4 with 100 ug pGX3024 administered by CELLECTRA intradermal electroporation. Guinea pig serum samples were collected at the indicated timepoints post-immunization with pGX3024 for measurement of specific IgG binding antibodies against HPV6 E7 (left) or HPV11 E7 (right) antigens by ELISA. Data are depicted as the mean±SEM of five animals.

Humoral responses against HPV6 E7 and HPV11 E7 antigens were measured by binding IgG ELISA in sera samples collected before and two weeks after each immunization. Timecourse of antibody levels are shown in FIG. 12. HPV6 E7 and HPV11 E7 binding antibodies were detected in guinea pigs following immunization with pGX3024.

Phase 1/2 Clinical Trial: INO-3107 With Electroporation (EP) in Subjects With HPV-6- and/or HPV-11-associated Recurrent Respiratory Papillomatosis (RRP) [Clinical Trials.gov Identifier: NCT04398433]

This is a Phase 1/2 open-label, multi-center trial to evaluate the safety, tolerability, immunogenicity, and efficacy of INO-3107 drug product in subjects with HPV-6- and/or HPV-11-associated recurrent respiratory papillomatosis (RRP). INO-3107 drug product will be administered IM followed by EP in subjects at Day 0, Weeks 3, 6, and 9.

This study will enroll approximately 20 adults (≥18 years old) who have been diagnosed with either Juvenile-Onset RRP (J-O RRP) as defined by age at first diagnosis <12 years or with Adult-Onset RRP (A-O RRP) as defined by age at first diagnosis ≥12 years. The trial population is divided into two cohorts: Cohort A: Participants with diagnoses of Juvenile-Onset RRP as defined by age at first diagnosis of RRP<12 years. Cohort B: Participants with Adult-onset RRP as defined by age at first diagnosis of RRP≥12 years.

This study will have a safety run-in with up to six participants with a one week waiting period between each enrolled participant. Safety and tolerability will continue to be assessed throughout the study after tolerability has been established. Tolerability will be determined by the reported incidence of dose-limiting toxicity (DLT), which is defined as:

Treatment-related NCI Common Terminology Criteria for Adverse Events (CTCAE, version 5.0) Grade≥3 non-hematological toxicity that does not respond to supportive therapy and lasts for longer than 48 hours, or;

Treatment-related NCI CTCAE v5.0 Grade≥3 hematological toxicity that does not respond to supportive therapy and lasts for longer than 48 hours.

Subjects will undergo routine surgical procedure for removal of papilloma(s) during the screening period within 14 days prior to Day 0 dosing (papilloma removal and Day 0 dose may be performed same day if other eligibility criteria have been fulfilled). Biopsy tissue will be collected and evaluated for secondary and exploratory endpoints. Status of disease during the trial will be monitored.

Cohort A (participants with Juvenile-Onset RRP) will be administered one 6.25 mg injection of INO-3107 drug product intramuscular (IM) injection followed by electroporation (EP) using CELLECTRA® 2000 at Day 0, Week 3, Week 6, and Week 9. Cohort B (participants with Adult-Onset RRP) will be administered one 6.25 mg injection of INO-3107 drug product intramuscular (IM) injection followed by EP using CELLECTRA® 2000 at Day 0, Week 3, Week 6, and Week 9.

The primary objective of the study is to evaluate the safety and tolerability of INO-3107 drug product in subjects with HPV-6 and/or HPV-11-associated RRP. The primary endpoint is safety and tolerability as assessed by reported adverse events (AE) and serious adverse events (SAE). The primary outcome measure is percentage of participants with Adverse Events (AEs) and Serious Adverse Events (SAEs) [Time Frame: Screening up to Week 52 (up to approximately 1 year)]. An adverse event (AE) is any untoward medical occurrence in a participant or clinical investigation participant administered a pharmaceutical product and that does not necessarily have a causal relationship with this treatment. An AE can include any unfavorable and unintended sign (including an abnormal laboratory finding), symptom, or disease temporally associated with the use of a medicinal (investigational) product, whether or not related to the medicinal (investigational) product. A serious adverse event (SAE) is any untoward medical occurrence that at any dose: 1. Results in death. 2. A life-threatening event; however, this does not include an event that, had it occurred in a more severe form, might have caused death. 3. Requires inpatient hospitalization or prolongation of existing hospitalization. 4. Results in persistent or significant disability/incapacity. 5. Results in a congenital anomaly/birth.

Secondary objectives of the study are:

1. To evaluate the efficacy of INO-3107 drug product, as determined by the frequency of RRP surgical interventions in the year following the first dose of investigational product, compared to the frequency in the year prior to Day 0;

2. To evaluate the efficacy of INO-3107 drug product as assessed by changes in the RRP Staging Assessment over time;

3. To evaluate the cellular immune response to INO-3107 drug product when given IM, followed by EP;

4. To evaluate the immunogenicity of INO-3107 drug product as assessed by pro-inflammatory and immunosuppressive elements in resected tumor tissue at study entry and, if available, at subsequent tissue resections;

5. To evaluate any potential association of microRNA (miRNA) profile with decreased frequency of RRP surgical intervention.

Secondary endpoints are:

1. The Number of RRP Surgical Interventions in the 52 Weeks Post Day 0 Compared to the Number of RRP Surgical Interventions in the Year Prior to Day 0 Dosing [Time Frame: Screening up to Week 52 (up to approximately 1 year)]

2. Change in RRP Staging Assessment Scores Over Time [Time Frame: Screening, Day 0, Weeks 6, 11, 26, 52 (up to approximately 1 year)]. An RRP Staging Assessment score will be determined using a modified Derkay staging tool. It includes both a subjective functional assessment of clinical parameters and an anatomic assessment of disease distribution. The anatomic score can then be used in combination with the functional score to measure an individual patient's clinical course and response to the therapy over time.

3. Change from Baseline in Interferon-gamma Enzyme-Linked Immunosorbent Spot (IFN-γ ELISpot) Response Magnitude for IFN-γ Secreting Cells in Peripheral Blood Mononuclear Cells (PBMCs) [Time Frame: Baseline, Weeks 6, 9, 11, 26, 52]

4. Change from Baseline in Flow Cytometry Response Magnitude for T-cell Phenotype and Lytic Potential in PBMCs [Time Frame: Baseline, Weeks 6, 9, 11, 26, 52]

5. Change from Baseline in Resected Tumor Tissue Response Magnitude for Pro-inflammatory and Immunosuppressive Elements [Time Frame: Baseline and at subsequent tissue resections, up to Week 52 (up to approximately 1 year)]

6. Change from Baseline in MicroRNA (miRNA) Expression Related to Reduced Frequency of RRP Surgical Intervention [Time Frame: Baseline and Week 6].

Exploratory objectives of the trial are:
1. To describe the virologic clearance of HPV-6 and/or 11 in resected tissue, if available;
2. To evaluate the humoral immune response to INO-3107 drug product when given IM, followed by EP;
3. To evaluate the immunogenicity of INO-3107 drug product as assessed by pro-inflammatory and immunosuppressive elements in peripheral blood;
4. To evaluate circulating free HPV DNA (cfHPV DNA) 6/11 as a correlate of disease burden and clinical outcomes in RRP patients treated with INO-3107 drug product.

The exploratory endpoints are:
1. Clearance of HPV-6/11 in resected tissue compared to baseline;
2. Antigen-specific humoral immune responses assessed by ELISA;
3. Assessment of pro-inflammatory and immunosuppressive elements in peripheral blood; and
4. Quantity of cfHPV DNA 6/11 pre- and post-INO-3107 drug product as a correlate of disease burden and clinical outcomes in RRP patients treated with INO-3107 drug product.

Efficacy Assessment: A detailed medical history will be obtained for each subject which will include documentation of HPV-6 and/or HPV-11 RRP, a list of RRP surgeries and therapies occurring within 3 years prior to screening, and any periods of remission. Subjects must have had at least two surgical RRP interventions (including laser) in the year prior to and including Day 0, to be eligible for the study. Subjects must require RRP intervention at the time of entry into this study and will undergo surgical removal of their papilloma(s) during screening, within 14 days prior to Day 0 dosing, to maximize standardization of baseline staging across subjects. The efficacy assessment will be based upon the number of RRP surgical interventions in the 52 weeks post Day 0 compared to the number of RRP surgical interventions in the year prior to Day 0 dosing. RRP surgical interventions include laser therapies. The trial will also evaluate changes in RRP Staging Assessment over time as a secondary endpoint.

Safety Assessment: Subjects will be followed for safety from the time of signing informed consent through Week 52, or the subject's last visit. The safety of INO-3107 drug product will be measured and graded in accordance with the CTCAE v5.0. Clinically significant changes in laboratory parameters and vital signs from baseline assessments will be assessed.

An adverse event is any untoward medical occurrence in a patient or clinical investigation subject administered a pharmaceutical product and which does not necessarily have to have a causal relationship with this treatment. An AE can therefore be any unfavorable and unintended sign (including an abnormal laboratory finding, for example), symptom, or disease temporally associated with the use of a medicinal product, whether or not considered related to the medicinal product. Adverse Events (AEs) include the following: pre- or post-treatment complications that occur as a result of protocol mandated procedure during or after screening (before the administration of clinical trial drug); any pre-existing condition, with the exception of the condition under investigation in this study, that increases in severity, or changes in nature during or as a consequence of the clinical trial drug administration phase; complications of pregnancy. Adverse Events (AEs) do not include the following: medical or surgical procedures (e.g., surgery, endoscopy, tooth extraction, transfusion) performed, however, the condition that leads to the procedure is an AE; pre-existing diseases or conditions or laboratory abnormalities present or detected before the Screening Visit that do not worsen; recurrences of RRP; situations where an untoward medical occurrence has not occurred (e.g., hospitalization for elective surgery, social and/or convenience admissions); overdose without clinical sequelae; any medical condition or clinically significant laboratory abnormality with an onset date before informed consent is provided, is not an AE; uncomplicated pregnancy; an induced elective abortion to terminate a pregnancy without medical reason.

Adverse drug reactions (ADRs) include all noxious and unintended responses to a medicinal product related to any dose. This means that a causal relationship between the medicinal product and an adverse event is at least a reasonable possibility (i.e., the relationship cannot be ruled out).

A serious adverse event (SAE) is any untoward medical occurrence that at any dose: results in death; is life-threatening; requires inpatient hospitalization or prolongation of existing hospitalization; results in persistent or significant disability/incapacity; results in congenital anomaly or birth defect; and/or an important medical event.

An unexpected adverse drug reaction is an adverse reaction, the nature or severity of which is not consistent with the applicable product information. An unanticipated (serious) adverse device effect (UADE) is any serious adverse effect on health or safety or any life-threatening problem or death caused by, or associated with, a device, if that effect, problem, or death was not previously identified in nature, severity, or degree of incidence in the investigational plan or application (including a supplementary plan or application), or any other unanticipated serious problem associated with a device that relates to the rights, safety, or welfare of subjects.

Immunogenicity Assessment: The study will explore humoral and cell mediated immune responses in blood samples taken at baseline (i.e. Screening and Day 0 prior to dosing) and Weeks 6, 9, 11, 26, and 52. Tissue samples will be collected at baseline and if clinically indicated during the study. Testing may include but is not limited to ELISA, ELISpot, flow cytometry, Immunohistochemistry (IHC), Nanostring on peripheral blood samples and/or resected tissue (study entry and recurrence, if available).

Profiling of miRNA may occur using tissue obtained at Screening, Day 0, and upon relapse. Assessment of Day 0 and screening samples will explore predictive algorithms for response to treatment with INO-3107. Samples assessed from relapse will describe how changes in miRNA profiles may associate with likelihood of relapse.

Virologic Assessment: The trial will evaluate the presence of HPV-6/11 DNA in tissue samples and peripheral blood, prior to and following study treatment, as described.

Key Inclusion Criteria:

Histologically-documented HPV-6- or HPV-11-positive respiratory papilloma or documentation of low-risk positive HPV using a Sponsor approved HPV-6/11 type-specific assay;

Requirement for frequent RRP intervention to remove or resect respiratory papilloma, as defined as at least 2 RRP surgical (including laser) interventions in the year prior to and including Day 0;

Must be an appropriate candidate for upcoming surgical intervention as per Investigator judgment and RRP Staging Assessment score Adequate bone marrow, hepatic, and renal function as defined by: ANC (Absolute Neutrophil Count)≥1000 cells/mm³, platelets≥50,000/mm³, hemoglobin≥9 g/dL; concentrations of total serum bilirubin within 1.5×upper limit of normal (ULN), AST and ALT within 1.5×ULN, serum creatinine≤1.5×ULN;

Participants must meet one of the following requirements:

Be of non-child bearing potential (>12 months of non-therapy-induced amenorrhea, confirmed by follicle-stimulating hormone [FSH], if not on hormone replacement);

Be surgically sterile (vasectomy in males or absence of ovaries and/or uterus in females);

Agree to use one highly effective or combined contraceptive methods that result in a failure rate of <1% per year during the treatment period and at least through week 12 after last dose; or Agree to abstinence from intercourse.

Key Exclusion Criteria:

Recipient of therapy directed towards RRP disease (other than surgery or ablation) including but not limited to antivirals (including cidofovir), radiation, chemotherapy, anti-angiogenic therapy (including bevacizumab), prophylactic HPV vaccination (including Gardasil) as therapeutic intervention, or therapy with an experimental agent within 3 months prior to Day 0;

Ongoing or recent (within 1 year) evidence of autoimmune disease that required treatment with systemic immunosuppressive treatments, with the exception of: vitiligo, childhood asthma that has resolved, type 1 diabetes, residual hypothyroidism that requires only hormone replacement, or psoriasis that does not require systemic treatment;

Diagnosis of immunodeficiency or treatment with systemic immunosuppressive therapy within 28 days prior to the first dose of trial treatment, including systemic corticosteroids;

High risk of bleeding or require the use of anticoagulants for management of a known bleeding diathesis;

Recipient of any live virus vaccine within 4 weeks prior to the first dose of trial treatment or any non-live virus vaccine within two weeks prior to the first dose of trial treatment;

History of clinically significant, medically unstable disease which, in the judgment of the Investigator, would jeopardize the safety of the participant, interfere with trial assessment or endpoint evaluation, or otherwise impact the validity of the trial results (This may include chronic renal failure; myocardial ischemia or infarction; New York Heart Association (NYHA) class III/IV cardiac disease); any cardiac preexcitation syndromes (such as Wolff-Parkinson-White; cardiomyopathy, or clinically significant arrhythmias); current malignancy with the exception of treated basal or squamous cell skin cancers, prostate cancer, or carcinoma of the cervix in situ; HIV, which may impact the ability to mount an immune response to the study therapy; or drug or alcohol dependence);

Fewer than two acceptable sites available for IM injection considering the deltoid and anterolateral quadriceps muscles [The following are unacceptable sites: Tattoos, keloids or hypertrophic scars located within 2 cm of intended treatment site; Cardioverter-defibrillator or pacemaker (to prevent a life-threatening arrhythmia) that is located ipsilateral to the deltoid injection site (unless deemed acceptable by a cardiologist); Metal implants or implantable medical device within the intended treatment site];

Pregnant or currently breastfeeding.

Clinical Trial Treatment: INO-3107 drug product is the investigational product to be used in this study. INO-3107 drug product contains DNA plasmid for expression of the E6 and E7 proteins of HPV 11 and HPV 6 genes (pGX3024) and expression plasmid expressing human IL-12 subunits (pGX6010). The INO-3107 drug product is a clear colorless solution that contains 6.25 mg total plasmid/mL (6 mg/mL pGX3024, 0.25 mg/mL pGX6010) in 150 mM sodium chloride and 15 mM sodium citrate, pH 7. A minimum volume of 1 mL will be filled into 2-mL clear glass vials for intramuscular injection.

Subjects will be administered one 6.25 mg injection of INO-3107 drug product intramuscularly followed by EP using CELLECTRA® 2000 EP device at Day 0, Week 3, Week 6, and Week 9.

The analysis populations will be the following:

The intention to treat (ITT) population includes all subjects who are eligible.

The modified intention to treat (mITT) population includes all subjects who receive at least one dose of INO-3107 drug product.

The per-protocol (PP) population comprises subjects who receive all doses of INO-3107 drug product and have no protocol violations. Subjects excluded from the PP population will be identified and documented prior to locking of the trial database.

The safety analysis set includes all subjects who receive at least one dose of INO-3107 drug product.

Peripheral Blood Immunogenicity Assessments: Whole blood and serum samples will be obtained at baseline (screening and Day 0 prior to dosing) and at Weeks 6, 9, 11, 26 and 52. Peripheral blood mononuclear cells (PBMCs) will be isolated from whole blood samples. Assessment of cellular immune activity may occur via the application of gene expression, Interferon-γ enzyme-linked immunosorbent spot (IFN-γ ELISpot), as well as flow cytometry assays. Additional assessment of cellular immune activity may occur via the application Flow Cytometry for the purposes of performing a Lytic Granule Loading Assay. The Lytic Granule Loading assay may examine the following external cellular markers: CD3, CD4, CD8 (T cell identification), Ki67, CD137, CD38 and CD69 (T cell activation markers) as well as PD-1 (exhaustion/activation marker), Tim-3, and Lag-3. The Lytic Granule Loading assay may additionally analyze the following intracellular markers: Granzyme A, Granzyme B, Granulysin and Perforin (proteins involved in lytic degranulation and cytotoxic potential).

Profiling of miRNA will occur using plasma obtained at Screening, Day 0, and Week 6. Assessment of Day 0 and Screening samples will explore predictive algorithms for response to treatment with INO-3107. Samples assessed from Week 6 will describe how changes in miRNA profiles may associate with ultimate treatment success or failure.

A standard binding ELISA may be performed to measure the anti-HPV-6/11 antibody response induced by INO-3107 drug product.

HPV-6/11 Testing: Whole blood will be collected prior to dosing at Day 0, and at Weeks 6, 11, 26 and 52 for measurement of cfHPV DNA-6/11.

Description of Statistical Methods:

Primary Analyses: The primary analyses for this trial are safety analyses of Treatment Emergent Adverse Events (TEAE) and clinically significant changes in safety laboratory parameters from baseline. TEAEs are defined for this trial as any AEs that occur following Day 0 following administration of study drug (IM+EP), until 30 days following the last dose. All TEAEs will be summarized among the Safety Population by frequency. These frequencies will be presented overall, by system organ class and by preferred term, the percentage of subjects affected. Additional frequencies will be presented with respect to maximum severity and to strongest relationship to study treatment. Multiple occurrences of the same AE will be counted only once following a worst-case approach with respect to severity and relationship to study treatment. The main summary of safety data will be based on TEAEs. For this summary, the frequency of preferred term events will be calculated along with 95% confidence intervals, using the exact method of Clopper-Pearson. Separate summaries will be based on events occurring within 7 days of any dose and regardless of when they occurred. AEs and SAEs that are not TEAEs or serious TEAEs will be presented in listings.

For AE data, partial start dates will be imputed to the date of treatment to conservatively report the event as treatment-emergent, whenever the portion of the date is consistent with that of the study treatment. Otherwise, it will be imputed to the earliest date consistent with the partial date. A completely missing onset date will be imputed as the day of treatment. Partial stop dates will be assumed to be the latest possible day consistent with the partial date.

AE duration will be calculated as (Stop Date−Start Date)+1.

Laboratory response variables will be descriptively summarized per time point and as changes from baseline including 95% confidence intervals. Shifts from baseline according to the CTCAE will also be presented. Laboratory values considered clinically significant will be presented in listings.

All of the safety analyses will be conducted on the subjects in the safety analysis set.

Analyses will be summarized and presented by number of prior surgical interventions (≤2, 3-5, and ≥6) and overall.

Secondary Analyses:

Efficacy: The frequency of RRP surgical interventions in the year following the first dose of INO-3107 drug product, compared to the frequency in the year prior to Day 0 dosing, will be summarized descriptively using mean fold-change and a 95% t-distribution-based CI. Changes in RRP Staging Assessment scores from baseline pre-dose to each post-dose evaluation will be analyzed. Median changes and associated 95% confidence intervals will be computed.

The relationship between the efficacy endpoint versus miRNA results will be examined. Relationships will be examined by using regression models, which model the endpoint outcome versus miRNA results as regressor variables.

Intersurgical intervals will also be summarized. Analyses will be summarized and presented by number of prior surgical interventions (≤2, 3-5, and ≥6) and overall. Efficacy analysis using the mITT population will be conducted. The per-protocol population will also be used for a supportive analysis.

Immunogenicity: Increases from baseline in interferon-γ ELISpot and flow response magnitudes will be summarized. The median increases and associated 95% confidence intervals will be calculated. Changes from baseline in tumor tissue response magnitudes will be summarized. The mean increases and associated 95% t-distribution based confidence intervals will be calculated. Valid samples for statistical analysis purposes will be those collected within 7 days of the specified visit. Baseline is defined as the last measurement prior to the first treatment administration. The mITT population will be used for immunogenicity analyses. Analyses will be summarized and presented by number of prior surgical interventions (≤2, 3-5, and ≥6) and overall.

Exploratory Analyses:

Efficacy: HPV clearance will be summarized; the percentage of subjects who clear HPV-6/11 in resected tumor tissue compared to baseline will be calculated. The relationship between cfHPV DNA 6/11 pre- and post-INO-3107 drug product as a correlate of disease burden and clinical outcomes in RRP patients will be examined using regression models. Analysis will be summarized and presented by number of prior surgical interventions (≤2, 3-5, and ≥6) and overall.

Immunogenicity: Post-baseline ELISA titers will be analyzed with geometric means. Changes in gene expression from baseline in peripheral blood will be summarized. Analysis will be summarized and presented by number of prior surgical interventions (≤2, 3-5, and ≥6) and overall.

```
Sequences and Sequence Identifiers

>pGX3024 insert only amino acid sequence without IgE Leader Sequence
<SEQ ID NO: 1>
ESKDASTSATSIDQLCKTFNLSLHTLQIQCVFCRNALTTAEIYAYAYKNLKVVWRDNFPFAACACCLELQGKINQ
YRHENYAAYAPTVEEETNEDILKVLIRCYLCHKPQCEIEKLKHILGKARFIKLNNQRKGRCLHCWTTCMEDLLPR
GRKRRSGSGATNFSLLKQAGDVEENPGPHGRLVTLKDIVLDLQPPDPVGLHAYEQLEDSSEDEVDKVDKQDSQPL
TQHYQILTCCCGCDSNVRLVVECTDGDIRQLQDLLLGTLNIVCPICAPKPRGRKRRSGSGATNFSLLKQAGDVEE
NPGPESANASTSATTIDQLCKTFNLSMHTLQINCVFCKNALTTAEIYSYAYKQLKVLFRGGYPYAACACCLEFHG
KINQYRHEDYAGYATTVEEETKQDILDVLIRCYLCHKPQCEVEKVKHILTKARFIKLNCTRKGRCLHCWTTCMED
MLPRGRKRRSGSGATNFSLLKQAGDVEENPGPHGRHVTLKDIVLDLQPPDPVGLHAYEQLVDSSEDEVDEVDGQD
SQPLKQHYQIVTCCCGCDSNVRLVVQCTETDIREVQQLLLGTLNIVCPICAPKT >pGX3024_Insert Only without IgE Leader Sequence <SEQ ID NO: 2>
GAGAGCAAGGATGCCAGCACAAGCGCCACCAGCATCGACCAGCTTTGCAAGACCTTTAACCTGAGCCTGCACACA
CTTCAGATCCAGTGTGTCTTCTGCCGAAATGCTCTGACAACAGCAGAAATCTACGCCTACGCCTACAAAAACCTG
AAGGTGGTGTGGAGAGACAACTTTCCTTTCGCTGCCTGCCTTGCTGCCTGGAGCTGCAGGGCAAGATCAATCAG
TACCGGCACTTCAACTACGCTGCCTACGCCCCTACAGTGGAGGAGGAAACAAACGAAGACATCCTGAAGGTGCTG
ATCAGATGCTACCTCTGCCACAAGCCACAGTGTGAAATCGAGAAGCTGAAGCACATTCTGGGCAAGGCCAGATTT
ATCAAGCTGAACAACCAGAGAAAGGGAAGATGTCTGCACTGTTGGACAACCTGCATGGAGGACCTGCTGCCCAGA
GGCAGAAAGAAGATCTGGCAGCGGAGCTACCAACTTCTCTCTGCTGAAGCAGGCTGGAGATGTTGAGGAGAAC
CCAGGCCCTCACGGCCGGCTGGTCACCCTGAAGGATATCGTGCTGGATCTGCAGCCCCCTGATCCTGTGGGCCTT
CACGCCTACGAACAGCTGGAGGACAGCTCTGAAGACGAAGTGGACAAGGTGGACAAGCAGGACTCTCAGCCTCTG
ACACAGCACTATCAGATCCTGACCTGCTGCTGCGGCTGTGACTCTAACGTGAGACTGGTGGTGGAGTGCACCGAT
GGAGACATCAGACAGCTGCAGGACCTGCTGCTGGGTACCCTGAACATTGTGTGTCCTATCTGTGCTCCAAAGCCA
AGAGGCAGGAAAAGAAGATCCGGCAGCGGAGCCACCAATTTCTCCCTGCTGAAGCAAGCTGGAGATGTGGAGGAG
```

| Sequences and Sequence Identifiers |
|---|
| AACCCTGGCCCTGAGAGCGCCAACGCCAGCACATCCGCCACCACCATCGACCAGCTGTGCAAGACCTTCAACCTG
AGCATGCACACACTGCAGATCAACTGTGTCTTCTGCAAGAATGCCCTGACCACAGCAGAGATCTACAGCTACGCC
TACAAGCAGCTGAAGGTGCTGTTCAGAGGCGGCTACCCTTATGCTGCCTGTGCCTGCTGCCTGGAGTTCCACGGC
AAGATCAACCAGTACAGACACTTCGACTACGCTGGCTACGCCACCACAGTGGAAGAGGAAACAAAGCAGGACATC
CTGGACGTGCTGATCCGATGCTACCTGTGCCACAAGCCTCAGTGTGAAGTGGAAAAAGTGAAGCACATCCTGACC
AAGGCCAGATTCATCAAGCTGAACTGCACCAGAAAAGGCAGATGCCTGCACTGCTGGACCACCTGCATGGAAGAC
ATGCTGCCTAGAGGCAGAAAAAGAAGAAGCGGCTCTGGAGCCGACCAACTTTTCCCTGCTGAAACAAGCTGGAGAC
GTGGAGGAAAACCCTGGCCCTCACGGCAGACACGTGACACTGAAGGACATCGTGCTGGACCTGCAGCCTCCTGAC
CCTGTGGGCCTGCACGCCTACGAGCAGCTGGTGGACAGCAGCGAGGACGAAGTGGACGAAGTGGATGGCCAGGAC
AGCCAGCCTCTGAAGCAGCACTACCAGATCGTCACCTGCTGCTGTGGCTGTGATAGCAATGTGAGGCTGGTGGTG
CAGTGCACAGAAACAGACATCAGAGAAGTGCAGCAACTGCTGCTGGGCACCCTGAACATCGTGTGTCCCATCTGT
GCTCCCAAGACATGATAA >pGX3024_Full Sequence <SEQ ID NO: 3>
gctgcttcgcgatgtacgggccagatatacgcgttgacattgattattgactagttattaatagtaatcaattac
ggggtcattagttcatagcccatatatggagttccgcgttacataacttacggtaaatggcccgcctggctgacc
gcccaacgaccccgcccattgacgtcaataatgacgtatgttcccatagtaacgccaatagggactttccattg
acgtcaatgggtggagtatttacggtaaactgcccacttggcagtacatcaagtgtatcatatgccaagtacgcc
ccctattgacgtcaatgacggtaaatggcccgcctggcattatgcccagtacatgaccttatgggactttcctac
ttggcagtacatctacgtattagtcatcgctattaccatggtgatgcggttttggcagtacatcaatgggcgtgg
atagcggtttgactcacggggatttccaagtctccaccccattgacgtcaatgggagtttgttttggcaccaaaa
tcaacgggactttccaaaatgtcgtaacaactccgccccattgacgcaaatgggcggtaggcgtgtacggtggga
ggtctatataagcagagctctctggctaactagagaacccactgcttactggcttatcgaaattaatacgactca
ctatagggagacccaagctggctagcgtttaaacttaagcttggtaccgagctcggatccgccaccatggattgg
acctggattctctttctcgttgccgctgctactcgcgttcatagtgagagcaaggatgccagcacaagcgccacc
agcatcgaccagctttgcaagacctttaacctgagcctgcacacacttcagatccagtgtgtcttctgccgaaat
gctctgacaacagcagaaatctacgcctacgcctacaaaaacctgaaggtggtgtggagagacaactttcctttc
gctgcctgcgcttgctgcctggagctgcagggcaagatcaatcagtacgcttcaactacgctgcctacgcc
cctacagtggaggaggaaacaaacgaagacatcctgaaggtgctgatcagatgctacctctgccacaagccacag
tgtgaaatcgagaagctgaagcacattctgggcaaggccagatttatcaagctgaacaaccagagaaagggaaga
tgtctgcactgttggacaacctgcatggaggacctgctgcccagaggcagaaagagaagatctggcagcggagct
accaacttctctctgctgaagcaggctggagatgttgaggagaaacccaggccctcacggccggctggtcaccctg
aaggatatcgtgctggatctgcagccccctgatcctgtgggccttcacgcctacgagcagctggaggacagctct
gaagacgaagtggacaaggtggacaagcaggactctcagcctctgacacagcactatcagatcctgacctgctgc
tgcggctgtgactctaacgtgagactggtggtggagtgcaccgatggagacatcagacagctgcaggacctgctg
ctgggtaccctgaacattgtgtgtcctatctgtgctccaaagccaagaggcaggaaaagaagatccggcagcgga
gccaccaatttctccctgctgaagcaagctggagatgtggaggagaaccctggccctgagagcgccaacgccagc
acatccgccaccaccatcgaccagctgtgcaagaccttcaacctgagcatgcacacactgcagatcaactgtgtc
ttctgcaagaatgccctgaccacagcagagatctacagctacgcctacaagcagctgaaggtgctgttcagaggc
ggctacccttatgctgcctgtgcctgctgcctggagttccacggcaagatcaaccagtacagacacttcgactac
gctggctacgccaccacagtggaagaggaaacaaagcaggacatcctggacgtgctgatccgatgctacctgtgc
cacaagcctcagtgtgaagtggaaaaagtgaagcacatcctgaccaaggccagattcatcaagctgaactgcacc
agaaaaggcagatgcctgcactgctggaccacctgcatggaagacatgctgcctagaggcagaaaaagaagaagc
ggctctggagccaccaactttccctgctgaaacaagctggagacgtggaggaaaaccctggccctcacggcaga
cacgtgacactgaaggacatcgtgctggacctgcagcctcctgacctgtgggcctgcacgcctacgagcagctg
gtggacagcagcgaggacgaagtggacgaagtggatggccaggacagccagcctctgaagcagcactaccagatc
gtcacctgctgctgtggctgtgatagcaatgtgaggctggtggtgcagtgcacagaaacagacatcagagaagtg
cagcaactgctgctgggcaccctgaacatcgtgtgtcccatctgtgctcccaagacatgataactcgagtctaga
gggcccgtttaaacccgctgatcagcctcgactgtgccttctagttgccagccatctgttgtttgcccctcccc
gtgccttccttgaccctggaaggtgccactcccactgtcctttcctaataaaatgaggaaattgcatcgcattgt
ctgagtaggtgtcattctattctggggggtggggtgggcaggacagcaaggggaggattgggaagacaatagc
aggcatgctggggatgcggtgggctctatggcttctactgggcggttttatggacagcaagcgaaccggaattgc
cagctggggcgccctctggtaaggttgggaagccctgcaaagtaaactggatggctttcttgccgccaaggatct
gatggcgcagggagtcaagctctgatcaagagacaggatgaggatcgtttcgcatgattgaacaagatggattgc
acgcaggttctccggccgcttgggtggagaggctattcggctatgactgggcacaacagacaatcggctgctctg
atgccgccgtgttccggctgtcagcgcaggggcgcccggttctttttgtcaagaccgacctgtccggtgccctga
atgaactgcaagacgaggcagcgcggctatcgtggctggccacgacgggcgttccttgcgcagctgtgctcgacg
ttgtcactgaagcgggaagggactggctgctattgggcgaagtgccggggcaggatctcctgtcatctcaccttg
ctcctgccgagaaagtatccatcatggctgatgcaatgcggcggctgcatacgcttgatccggctacctgcccat
tcgaccaccaagcgaaacatcgcatcgagcgagcacgtactcggatggaagccggtcttgtcgatcaggatgatc
tggacgaagagcatcaggggctcgcgccagccgaactgttcgccaggctcaaggcgagcatgcccgacggcgagg
atctcgtcgtgacccatggcgatgcctgcttgccgaatatcatggtggaaaatggccgcttttctggattcatcg
actgtggccggctgggtgtggcggaccgctatcaggacatagcgttggctacccgtgatattgctgaagagcttg
gcggcgaatgggctgaccgcttcctcgtgctttacggtatcgccgctcccgattcgcagcgcatcgccttctatc
gccttcttgacgagttcttctgaattattaacgcttacaatttcctgatgcggtattttctccttacgcatctgt
gcggtatttcacaccgcatcaggtggcacttttcggggaaatgtgcgcggaacccctatttgtttatttttctaa
atacattcaaatatgtatccgctcatgagacaataaccctgataaatgcttcaataatagcacgtgctaaaactt
cattttatttaaaggatctaggtgaagatcctttttgataatctcatgaccaaaatcccttaacgtgagttt
tcgttccactgagcgtcagaccccgtagaaaagatcaaaggatcttcttgagatcctttttttctgcgcgtaatc
tgctgcttgcaaacaaaaaaaccaccgctaccagcggtggtttgtttgccggatcaagagctaccaactctttttt
ccgaaggtaactggcttcagcagagcgcagataccaaatactgttcttctagtgtagccgtagttaggccaccac
ttcaagaactctgtagcaccgcctacatacctcgctctgctaatcctgttaccagtggctgctgccagtggcgat
aagtcgtgtcttaccgggttggactcaagacgatagttaccggataaggcgcagcggtcgggctgaacggggggt
tcgtgcacacagcccagcttggagcgaacgacctacaccgaactgagatacctacagcgtgagctatgagaaagc
gccacgcttcccgaagggagaaaggcggacaggtatccggtaagcggcagggtcggaacaggagagcgcacgagg | gagcttccaggggaaacgcctggtatctttatagtcctgtcgggtttcgccacctctgacttgagcgtcgattt
ttgtgatgctcgtcaggggggcggagcctatggaaaaacgccagcaacgcggccttttacggttcctggccttt
tgctggccttttgctcacatgttctt SEQ ID NO: 4 pGX6010 full length sequence and annotation:

| Elements: | Base Pairs: |
|---|---|
| Kan Resistance: | 298-1059 |
| pUC Ori: | 1227-1900 |
| bGH polyA: | 2290-2528 |
| XhoI site: | 2551-2556 |
| huIL-12p35 coding sequence: | 2557-3216 (Note: p35 subunit is encoded on the opposite strand) |
| PmeI site: | 3217-3224 |
| sCMV Promoter: | 3209-3711 |
| hCMV promoter: | 4200-5024 |
| SalI site: | 5030-5035 |
| huIL-12 p40: | 5036-6022 |
| MluI site: | 6023-6028 |
| SV40 polyA: | 6024-6229 |

```
aaatggggc gctgaggtct gcctcgtgaa gaaggtgttg ctgactcata ccaggcctga   60
atcgccccat catccagcca gaaagtgagg gagccacggt tgatgagagc tttgttgtag  120
gtggaccagt tggtgatttt gaactttgc tttgccacgg aacggtctgc gttgtcggga  180
agatgcgtga tctgatcctt caactcagca aaagttcgat ttattcaaca aagccgccgt  240
cccgtcaagt cagcgtaatg ctctgccagt gttacaacca attaaccaat tctgcgttca  300
aaatggtatg cgttttgaca catccactat atatccgtgt cgttctgtcc actcctgaat  360
cccattccag aaattctcta gcgattccag aagtttctca gagtcggaaa gttgaccaga  420
cattacgaac tggcacagat ggtcataacc tgaaggaaga tctgattgct taactgcttc  480
agttaagacc gacgcgctcg tcgtataaca gatgcgatga tgcagaccaa tcaacatggc  540
acctgccatt gctacctgta cagtcaagga tggtagaaat gttgtcggtc cttgcacacg  600
aatattacgc catttgcctg catattcaaa cagctcttct acgataaggg cacaaatcgc  660
atcgtggaac gtttgggctt ctaccgattt agcagtttga tacactttct ctaagtatcc  720
acctgaatca taaatcggca aaatagagaa aaattgacca tgtgtaagcg gccaatctga  780
ttccacctga gatgcataat ctagtagaat ctcttcgcta tcaaaattca cttccacctt  840
ccactcaccg gttgtccatt catggctgaa ctctgcttcc tctgttgaca tgacacacat  900
catctcaata tccgaatacg gaccatcagt ctgacgacca agagagccat aaacaccaat  960
agccttaaca tcatccccat atttatccaa tattcgttcc ttaatttcat gaacaatctt 1020
cattctttct tctctagtca ttattattgg tccgttcata acaccccttg tattactgtt 1080
tatgtaagca gacagtttta ttgttcatga tgatatattt ttatcttgtg caatgtaaca 1140
tcagagattt tgagacacaa cgtggctttc cccggcccat gaccaaaatc ccttaacgtg 1200
agttttcgtt ccactgagcg tcagaccccg tagaaaagat caaaggatct tcttgagatc 1260
ctttttttct gcgcgtaatc tgctgcttgc aaacaaaaaa accaccgcta ccagcggtgg 1320
tttgtttgcc ggatcaagag ctaccaactc ttttttccgaa ggtaactggc ttcagcagag 1380
cgcagatacc aaatactgtt cttctagtgt agccgtagtt aggccaccac ttcaagaact 1440
ctgtagcacc gcctacatac ctcgctctgc taatcctgtt accagtggct gctgccagtg 1500
gcgataagtc gtgtcttacc gggttggact caagacgata gttaccggat aaggcgcagc 1560
ggtcgggctg aacggggggt tcgtgcacac agcccagctt ggagcgaacg acctacaccg 1620
aactgagata cctacagcgt gagctatgag aaagcgccac gcttcccgaa gggagaaagg 1680
cggacaggta tccggtaagc ggcagggtcg aacaggaga gcgcacgagg gagcttccag 1740
ggggaaacgc ctggtatctt tatagtcctg tcgggtttcg ccacctctga cttgagcgtc 1800
gattttttgtg atgctcgtca ggggggcgga gcctatggaa aaacgccagc aacgcggcct 1860
ttttacggtt cctggccttt tgctggcctt tgctcacat gttcttttcct gcgttatccc 1920
ctgattctgt ggataaccgt attaccgcct ttgagtgagc tgataccgct cgccgcagcc 1980
gaacgaccga gcgcagcgag tcagtgagcg aggaagcgga agagcgcctg atgcggtatt 2040
ttctccttac gcatctgtgc ggtatttcac accgcatatg gtgcactctc agtacaatct 2100
gctctgatgc cgcatagtta agccagtatc tgctccctgc ttgtgtgttg gaggtcgctg 2160
agtagtgcgc gagcaaaatt taagctacaa caaggcaagg cttgaccgac aattcgatga 2220
agaatctgct tagggttagg cgttttgcgc tgcttcgcga tgtacgggcc agatatagcc 2280
gcggcatcga tgataattcg gcttatttaa attccccagc atgcctgcta ttgtcttccc 2340
aatcctcccc cttgctgtcc tgccccaccc caccccccag aatagaatga cacctactca 2400
gacaatgcga tgcaatttcc tcattttatt aggaaaggac agtgggagtg gcaccttcca 2460
gggtcaagga aggcacgggg gagggggcaaa caacagatgg ctggcaacta gaaggcacag 2520
tcgaggctga tcagcgagct cggcgcgcct ctcgagttag gaagcgttca ggtatgacat 2580
gacccgatca atagtgacag cccgaatccg aaaggcatgc agcagaatgc acagcttgat 2640
ttttgtctta taaaagtcgg gttcctccag actagacttc tgtggacgg tttcgctatt 2700
gaagttcagg gcctgcatca gctcgtcaat cactgccagc atattctgat ccagaaagat 2760
ctgtcgttta gggtccatca gcagcttagc gttcatggtt ttgaattcca cctgatacat 2820
cttcagatcc tcgtagatgg agctcaggca cagtgccatc atgaagctgg tcttgcgact 2880
agccaggcaa gacccgttgg tgatgaagga agtctccctg ctattcagac atgattcgtt 2940
cttggtcagc tccagtggca ggcaggcttc gactgtggag gttttgtcct tagtaatatc 3000
ctcgtggtcg atttcctcag aagtacaagg gtaaaactcc agtgtctgtc tagctttctg 3060
cagcatattg gacacggccc gcagcaggtt ctggctatgg tgcaggcagg gaacatgcc 3120
aggatcgggg gtagcgacag gcagatttcg agccagtgac aggtgatcca gcaggaccag 3180
ggtagcgacc agcagcaggg accgagcggg gcacatgttt aaacgctcct ccgacgtccc 3240
caggcagaat ggcggttccc taaacgagca ttgcttatat agacctccca ttaggcacgc 3300
ctaccgccca tttacgtcaa tggaacgccc atttgcgtca ttgcccctcc ccattgacgt 3360
```

| Sequences and Sequence Identifiers |
|---|
| caatggggat gtacttggca gccatcgcgg gccatttacc gccattgacg tcaatgggag 3420 |
| tactgccaat gtaccctggc gtacttccaa tagtaatgta cttgccaagt tactattaat 3480 |
| agatattgat gtactgccaa gtgggccatt taccgtcatt gacgtcaata gggggcgtga 3540 |
| gaacggatat gaatgggcaa tgagccatcc cattgacgtc aatggtgggt ggtcctattg 3600 |
| acgtcaatgg gcattgagcc aggcgggcca tttaccgtaa ttgacgtcaa tgggggaggc 3660 |
| gccatatacg tcaataggac cgcccatatg acgtcaatag gaaagaccat gctaagccga 3720 |
| attatcgcgg ctatctgagg ggactagggt gtgtttaggc gaaaagcggg gcttcggttg 3780 |
| tacgcggtta ggagtcccct caggatatag tagtttcgct tttgcataggg gaggggggaaa 3840 |
| tgtagtctta tgcaatactc ttgtagtctt gcaacatggt aacgatgagt tagcaacatg 3900 |
| ccttacaagg agagaaaaag caccgtgcat gccgattggt ggaagtaagg tggtacgatc 3960 |
| gtgccttatt aggaaggcaa cagacgggtc tgacatggat tggacgaacc actgaattcc 4020 |
| gcattgcaga gatattgtat ttaagtgcct agctcgatac aataaacgcc atttgaccat 4080 |
| tcaccacatt ggtgtgcacc tccaagcttc gaccaattct catgtttgac agcttatcat 4140 |
| cgcagatccg ggcaacgttg ttgccattgc tgcaggcgca gaactggtag gtatggaaga 4200 |
| tctatacatt gaatcaatat tggcaattag ccatattagt cattggttat atagcataaa 4260 |
| tcaatattgg ctattggcca ttgcatacgt tgtatctata tcataatatg tacatttata 4320 |
| ttggctcatg tccaatatga ccgccatgtt gacattgatt attgactagt tattaatagt 4380 |
| aatcaattac ggggtcatta gttcatagcc catatatgga gttccgcgtt acataactta 4440 |
| cggtaaatgg cccgcctggc tgaccgccca acgaccccg cccattgacg tcaataatga 4500 |
| cgtatgttcc catagtaacg ccaataggga cttttccattg acgtcaatg gtggagtatt 4560 |
| tacggtaaac tgcccacttg gcagtacatc aagtgtatca tatgccaagt ccgccccta 4620 |
| ttgacgtcaa tgacggtaaa tggcccgcct ggcattatgc ccagtacatg accttacggg 4680 |
| actttcctac ttggcagtac atctacgtat tagtcatcgc tattaccatg gtgatgcggt 4740 |
| tttggcagta catcaatggg cgtggatagc ggtttgactc acggggattt ccaagtctcc 4800 |
| accccattga cgtcaatggg agtttgtttt ggcaccaaaa tcaacgggac tttccaaaat 4860 |
| gtcgtaacaa ctccgcccca ttgacgcaaa tgggcggtag gcgtgtacgg tgggaggtct 4920 |
| atataagcag agctcgttta gtgaaccgtc agatcgcctg gagacgccat ccacgctgtt 4980 |
| ttgacctcca tagaagacac cgggaccgat ccagcctccg ggcggcgcgg tcgacatgtg 5040 |
| ccatcagcag ctggtcatct cttggtttag tctggtgttt ctggcttctc cactggtcgc 5100 |
| tatctgggaa ctgaaaaagg atgtgtacgt ggtcgagctg gactggtatc cagatgcacc 5160 |
| cggagaaatg gtggtcctga cctgcgacac acccgaggaa gatggcatca cttggaccct 5220 |
| ggaccagagc tccgaggtgc tgggatctgg caagacactg actattcagg tcaaagaatt 5280 |
| cggggatgcc ggacagtaca catgtcacaa gggcggggag gtgctgagtc actcactgct 5340 |
| gctgctgcat aagaaagaag acggcatctg gtctactgac attctgaagg atcagaaaga 5400 |
| gcctaagaac aaaaccttcc tgagatgcga agctaagaat tatagtggga ggtttacctg 5460 |
| ttggtggctg accacaatct caactgacct gacctttagc gtgaaatcta gtaggggtc 5520 |
| aagcgatcca cagggagtga cctgcgagac agctacactg agcgccgagc gggtgagagg 5580 |
| agacaacaag gagtacgaat atagtgtcga gtgccaggaa gattcagcct gtcccgcagc 5640 |
| cgaggaatcc ctgcctatcg aagtgatggt ggacgctgtg cacaagctga aatacgaaaa 5700 |
| ctacacatcc tctttctta ttcgcgacat cattaagcca gatcccccta aaaacctgca 5760 |
| gctgaagccc ctgaaaaatt cccgacaggt ggaggtctct tgggaatacc ctgatacatg 5820 |
| gagcactcca cattcttatt tcagtctgac tttttgcgtg caggtccagg gcaaagcaa 5880 |
| aagggagaag aaagaccgcg tgttcaccga taagacatcc gctactgtca tctgtcgaaa 5940 |
| aaacgcaagc atttccgtgc gggcacagga taggtattat tccagcagtt ggtctgagtg 6000 |
| ggcttccgtc ccttgtagtt gaacgcgtaa aaagatccag actgataag atacattgat 6060 |
| gagtttggac aaaaccacaac tagaatgcag tgaaaaaaat gctttatttg tgaaatttgt 6120 |
| gatgctattg ctttatttgt aaccattata agctgcaata aacaagttaa caacaacaat 6180 |
| tgcattcatt ttatgtttca ggttcagggg gaggtgtggg aggtttttt     6229 |

SEQ ID NO: 5-p35 DNA sequence:
ATGTGTCCAGCGCGCAGCCTCCTCCTTGTGGCTACCCTGGTCCTCCTGGACCACCTCAGTTTGGCCAGAAACCTC
CCCGTGGCCACTCCAGACCCAGGAATGTTCCCATGCCTTCACCACTCCCAAAACCTGCTGAGGGCCGTCAGCAAC
ATGCTCCAGAAGGCCAGACAAACTCTAGAATTTTACCCTTGCACTTCTGAAGAGATTGATCATGAAGATATCACA
AAAGATAAAACCAGCACAGTGGAGGCCTGTTTACCATTGGAATTAACCAAGAATGAGAGTTGCCTAAATTCCAGA
GAGACCTCTTTCATAACTAATGGGAGTTGCCTGGCCTCCAGAAAGACCTCTTTTATGATGGCCCTGTGCCTTAGT
AGTATTTATGAAGACTTGAAGATGTACCAGGTGGAGTTCAAGACCATGAATGCAAAGCTTCTGATGGATCCTAAG
AGGCAGATCTTTCTAGATCAAAACATGCTGGCAGTTATTGATGAGCTGATGCAGGCCCTGAATTTCAACAGTGAG
ACTGTGCCACAAAAATCCTCCCTTGAAGAACCGGATTTTTATAAAACTAAAATCAAGCTCTGCATACTTCTTCAT
GCTTTCAGAATTCGGGCAGTGACTATTGATAGAGTGATGAGCTATCTGAATGCTTCCTAA SEQ ID NO: 6-p35 amino acid sequence:
MCPARSLLLVATLVLLDHLSLARNLPVATPDPGMFPCLHHSQNLLRAVSNMLQKARQTLEFYPCTSEEIDHEDIT
KDKTSTVEACLPLELTKNESCLNSRETSFITNGSCLASRKTSFMMALCLSSIYEDLKMYQVEFKTMNAKLLMDPK
RQIFLDQNMLAVIDELMQALNFNSETVPQKSSLEEPDFYKTKIKLCILLHAFRIRAVTIDRVMSYLNAS*

SEQ ID NO: 7-p40 DNA sequence:
ATGTGTCACCAGCAGTTGGTCATCTCTTGGTTTTCCCTGGTTTTTCTGGCATCTCCCCTCGTGGCCATATGGGAA
CTGAAGAAAGATGTTTATGTCGTAGAATTGGATTGGTATCCGGATGCCCCTGGAGAAATGGTGGTCCTCACCTGT
GACACCCCTGAAGAAGATGGTATCACCTGGACCTTGGACCAGAGCAGTGAGGTCTTAGGCTCTGGCAAAACCCTG
ACCATCCAAGTCAAAGAGTTTGGAGATGCTGGCCAGTACACCTGTCACAAAGGAGGCGAGGTTCAAGCCATTCG
CTCCTGCTGCTTCACAAAAAGGAAGATGGAATTTGGTCCACTGATATTTTAAAGGACCAGAAAGAACCCAAAAAT
AAGACCTTTCTAAGATGCGAGGCCAAGAATTATTCTGGACGTTTCACCTGCTGGTGGCTGACGACAATCAGTACT
GATTTGACATTCAGTGTCAAAAGCAGCAGAGGCTCTTCTGACCCCCAAGGGGTGACGTGCGGAGCTGCTACACTC
TCTGCAGAGAGAGTCAGAGGGGACAACAAGGAGTATGAGTACTCAGTGGAGTGCCAGGAGGACAGTGCCTGCCCA
GCTGCTGAGGAGAGTCTGCCCATTGAGGTCATGGTGGATGCCGTTCACAAGCTCAAGTATGAAAACTACACCAGC
AGCTTCTTCATCAGGGACATCATCAAACCTGACCCACCCAAGAACTTGCAGCTGAAGCCATTAAAGAATTCTCGG
CAGGTGGAGGTCAGCTGGGAGTACCCTGACACCTGGAGTACTCCACATTCCTACTTCTCCCTGACATTCTGCGTT

| Sequences and Sequence Identifiers |
|---|
| CAGGTCCAGGGCAAGAGCAAGAGAGAAAAGAAAGATAGAGTCTTCACGGACAAGACCTCAGCCACGGTCATCTGC<br>CGCAAAAATGCCAGCATTAGCGTGCGGGCCCAGGACCGCTACTATAGCTCATCTTGGAGCGAATGGGCATCTGTG<br>CCCTGCAGTTAG<br><br>SEQ ID NO: 8 p40 amino acid sequence:<br>MCHQQLVISWFSLVFLASPLVAIWELKKDVYVVELDWYPDAPGEMVVLTCDTPEEDGITWTLDQSSEVLGSGKTL<br>TIQVKEFGDAGQYTCHKGGEVLSHSLLLLHKKEDGIWSTDILKDQKEPKNKTFLRCEAKNYSGRFTCWWLTTIST<br>DLTFSVKSSRGSSDPQGVTCGAATLSAERVRGDNKEYEYSVECQEDSACPAAEESLPIEVMVDAVHKLKYENYTS<br>SFFIRDIIKPDPPKNLQLKPLKNSRQVEVSWEYPDTWSTPHSYFSLTFCVQVQGKSKREKKDRVFTDKTSATVIC<br>RKNASISVRAQDRYYSSSWSEWASVPCS*<br><br>SEQ ID NO: 9 IgE Leader DNA sequence<br>atggactgga cctggatcct gttcctggtg gccgctgcca cacgggtgca cagc<br><br>SEQ ID NO: 10 IgE leader protein<br>Met Asp Trp Thr Trp Ile Leu Phe Leu Val Ala Ala Ala Thr Arg Val His Ser<br><br>>pGX3024 insert amino acid sequence with IgE Leader Sequence<br><SEQ ID NO: 11><br>MDWTWILFLVAAATRVHSESKDASTSATSIDQLCKTFNLSLHTLQIQCVFCRNALTTAEIYAYAYKNLKVVWRDN<br>FPPFAACACCLELQGKINQYRHFNYAAYAPTVEEETNEDILKVLIRCYLCHKPQCEIEKLKHILGKARFIKLNNQR<br>KGRCLHCWTTCMEDLLPRGRKRRSGSGATNFSLLKQAGDVEENPGPHGRLVTLKDIVLDLQPPDPVGLHAYEQLE<br>DSSEDEVDKVDKQDSQPLTQHYQILTCCCGCDSNVRLVVECTDGDIRQLQDLLLGTLNIVCPICAPKPRGRKRRS<br>GSGATNFSLLKQAGDVEENPGPESANASTSATTIDQLCKTFNLSMHTLQINCVFCKNALTTAEIYSYAYKQLKVL<br>FRGGYPYAACACCLEFHGKINQYRHFDYAGYATTVEEETKQDILDVLIRCYLCHKPQCEVEKVKHILTKARFIKL<br>NCTRKGRCLHCWTTCMEDMLPRGRKRRSGSGATNFSLLKQAGDVEENPGPHGRHVTLKDIVLDLQPPDPVGLHAY<br>EQLVDSSEDEVDEVDGQDSQPLKQHYQIVTCCCGCDSNVRLVVQCTETDIREVQQLLLGTLNIVCPICAPKT<br><br>>pGX3024_Insert Only with IgE Leader Sequence <SEQ ID NO: 12><br>ATGGATTGGACCTGGATTCTCTTTCTCGTTGCCGCTGCTACTCGCGTTCATAGTGAGAGCAAGGATGCCAGCACA<br>AGCGCCACCAGCATCGACCAGCTTTGCAAGACCTTTAACCTGAGCCTGCACACACTTCAGATCCAGTGTGTCTTC<br>TGCCGAAATGCTCTGACAACAGCAGAAATCTACGCCTACGCCTACAAAAACCTGAAGGTGGTGTGGAGAGACAAC<br>TTTCCTTTCGCTGCCTGCGCTTGCTGCCTGGAGCTGCAGGGCAAGATCAATCAGTACCGGCACTTCAACTACGCT<br>GCCTACGCCCCTACAGTGGAGGAGGAAACAAACGAAGACATCCTGAAGGTGCTGATCAGATGCTACCTCTGCCAC<br>AAGCCACAGTGTGAAATCGAGAAGCTGAAGCACATTCTGGGCAAGGCCAGATTTATCAAGCTGAACAACCAGAGA<br>AAGGGAAGATGTCTGCACTGTTGGACAACCTGCATGGAGGACCTGCTGCCCAGAGGCAGAAAGAGAAGATCTGGC<br>AGCGGAGCTACCAACTTCTCTCTGCTGAAGCAGGCTGGAGATGTTGAGGAGAACCCAGGCCCTCACGGCCGGCTG<br>GTCACCCTGAAGGATATCGTGCTGGATCTGCAGCCCCTGATCCTGTGGGCCTTCACGCCTACGAACAGCTGGAG<br>GACAGCTCTGAAGACGAAGTGGACAAGGTGGACAAGCAGGACTCTCAGCCTCTGACACAGCACTATCAGATCCTG<br>ACCTGCTGCTGCGGCTGTGACTCTAACGTGAGACTGGTGGTGGAGTGCACCGATGGAGACATCAGACAGCTGCAG<br>GACCTGCTGCTGGGTACCCTGAACATTGTGTGTCCTATCTGTGCTCCAAAGCCAAGAGGCAGGAAAAGAAGATCC<br>GGCAGCGGAGCCACCAATTTCTCCCTGCTGAAGCAAGCTGGAGATGTGGAGGAGAACCCTGGCCCTGAGAGCGCC<br>AACGCCAGCACATCCGCCACCACCATCGACCAGCTGTGCAAGACCTTCAACCTGAGCATGCACACACTGCAGATC<br>AACTGTGTCTTCTGCAAGAATGCCCTGACCACAGCAGAGATCTACAGCTACGCCTACAAGCAGCTGAAGGTGCTG<br>TTCAGAGGCGGCTACCCTTATGCTGCCTGTGCCTGCTGCCTGGAGTTCCACGGCAAGATCAACCAGTACAGACAC<br>TTCGACTACGCTGGCTACGCCACCACAGTGGAAGAGGAAACAAAGCAGGACATCCTGGACGTGCTGATCCGATGC<br>TACCTGTGCCACAAGCCTCAGTGTGAAGTGGAAAAAGTGAAGCACATCCTGACCAAGGCCAGATTCATCAAGCTG<br>AACTGCACCAGAAAGGCAGATGCCTGCACTGCTGGACCACCTGCATGGAAGACATGCTGCCTAGAGGCAGAAAA<br>AGAAGAAGCGGCTCTGGAGCCACCAACTTTTCCCTGCTGAAACAAGCTGGAGACGTGGAGGAAAACCCTGGCCCT<br>CACGGCAGACACGTGACACTGAAGGACATCGTGCTGGACCTGCAGCCTCCTGACCCTGTGGGCCTGCACGCCTAC<br>GAGCAGCTGGTGGACAGCAGCGAGGACGAAGTGGACGAAGTGGATGGCCAGGACAGCCAGCCTCTGAAGCAGCAC<br>TACCAGATCGTCACCTGCTGCTGTGGCTGTGATAGCAATGTGAGGCTGGTGGTGCAGTGCACAGAAACAGACATC<br>AGAGAAGTGCAGCAACTGCTGCTGGGCACCCTGAACATCGTGTGTCCCATCTGTGCTCCCAAGACATGATAA |

What is claimed:

1. A nucleic acid molecule encoding a human papillomavirus (HPV) antigen, the HPV antigen comprising:
the amino acid sequence of SEQ ID NO: 1 or SEQ ID NO: 11; or
an amino acid sequence that is at least 95% homologous to SEQ ID NO: 1 or SEQ ID NO: 11.

2. The nucleic acid molecule according to claim 1, comprising:
a nucleotide sequence at least 95% homologous to SEQ ID NO: 2 or SEQ ID NO: 12;
the nucleotide sequence of SEQ ID NO: 2; or
the nucleotide sequence of SEQ ID NO 12.

3. An expression vector comprising the nucleic acid molecule according to claim 1.

4. The expression vector of claim 3 comprising a DNA plasmid.

5. The expression vector of claim 3, comprising the nucleotide sequence of SEQ ID NO: 3.

6. An immunogenic protein comprising:
the amino acid sequence of SEQ ID NO: 1 or SEQ ID NO: 11, or
an amino acid sequence that is at least 95% homologous to the amino acid sequence of SEQ ID NO: 1 or SEQ ID NO: 11.

7. A vaccine comprising the expression vector of claim 3 and a pharmaceutically acceptable excipient.

8. A pharmaceutical composition comprising the expression vector of claim 3 and a pharmaceutically acceptable excipient.

9. The pharmaceutical composition according to claim 8, comprising an adjuvant.

10. The pharmaceutical composition according to claim 9 wherein the adjuvant comprises interleukin-12 (IL12).

11. The pharmaceutical composition according to claim 9 wherein the adjuvant comprises a nucleic acid molecule encoding IL12.

12. The pharmaceutical composition according to claim 11, wherein the nucleic acid molecule encoding IL12 is an expression vector.

13. A vaccine comprising the immunogenic protein of claim 6 and a pharmaceutically acceptable excipient.

14. A pharmaceutical composition comprising the immunogenic protein of claim 6 and a pharmaceutically acceptable excipient.

15. The pharmaceutical composition according to claim 14, comprising an adjuvant.

16. The pharmaceutical composition according to claim 15 wherein the adjuvant comprises interleukin-12 (IL12).

17. The pharmaceutical composition according to claim 9, wherein the adjuvant comprises a nucleic acid molecule comprising a nucleotide sequence encoding the p35 subunit of IL-12, the p40 subunit of IL-12, or both.

18. The pharmaceutical composition according to claim 17, wherein the nucleotide sequence encoding the p35 subunit of IL12 comprises a nucleotide sequence selected from the group consisting of:
a nucleotide sequence that encodes SEQ ID NO: 6; or
a nucleotide sequence that is at least 95% homologous to a nucleotide sequence that encodes SEQ ID NO: 6.

19. The pharmaceutical composition according to claim 17, wherein the nucleotide sequence encoding the p40 subunit of IL12 comprises a nucleotide sequence selected from the group consisting of:
a nucleotide sequence that encodes SEQ ID NO: 8; or
a nucleotide sequence that is at least 95% homologous to a nucleotide sequence that encodes SEQ ID NO: 8.

20. The pharmaceutical composition according to claim 17, wherein the nucleotide sequence encoding IL12 comprises a nucleotide sequence selected from the group consisting of:

the nucleotide sequence of SEQ ID NO: 4; or a nucleotide sequence that is at least 95% homologous to the nucleotide sequence of SEQ ID NO: 4.

21. The pharmaceutical composition according to claim 17 wherein the nucleic acid molecule comprising a nucleotide sequence encoding the p35 subunit of IL-12, the p40 subunit of IL-12, or both is an expression vector.

22. The pharmaceutical composition according to claim 21 wherein the expression vector comprising the nucleic acid molecule encoding the p35 subunit of IL-12, the p40 subunit of IL-12, or both is the same expression vector or a different expression vector than the expression vector comprising the nucleic acid molecule encoding the HPV antigen.

23. The pharmaceutical composition according to claim 8 wherein the pharmaceutically acceptable excipient comprises a buffer.

24. The pharmaceutical composition of claim 23, wherein the buffer is a saline-sodium citrate buffer, and wherein the composition comprises 6 mg of the vector encoding the HPV antigen per milliliter of buffer and 0.25 mg of the vector encoding the p35 subunit of IL-12, the p40 subunit of IL-1, or both, per milliliter of buffer.

25. The pharmaceutical composition of claim 24, wherein the composition comprises 6 mg of pGX3024 per milliliter of buffer and 0.25 mg of pGX6010 per milliliter of buffer.

26. A method of inducing an immune response in a subject comprising administering to the subject an effective amount of the pharmaceutical composition according to claim 22, to thereby induce the immune response.

27. A method of prophylactically or therapeutically immunizing a subject against HPV6 and/or HPV11 comprising administering to the subject an effective amount of the pharmaceutical composition according to claim 22 to thereby induce an immune response against HPV6, HPV11, or both.

28. A method for treating or preventing recurrent respiratory papillomatosis (RRP) in a subject comprising administering to the subject an effective amount the pharmaceutical composition according to according to claim 22 to thereby treat or prevent RRP.

29. The method according to claim 28 wherein the RRP is juvenile-onset RRP or adult-onset RRP.

30. The method according to claim 26, wherein the administering comprises intradermal or intramuscular injection.

31. The method according to claim 30, wherein the administering further comprises electroporation.

32. The method according to claim 27, wherein the administering comprises intradermal or intramuscular injection.

33. The method according to claim 32, wherein the administering further comprises electroporation.

34. The method according to claim 28, wherein the administering comprises intradermal or intramuscular injection.

35. The method according to claim 34, wherein the administering further comprises electroporation.

* * * * *